US009260694B2

(12) United States Patent
Guehenneux et al.

(10) Patent No.: US 9,260,694 B2
(45) Date of Patent: Feb. 16, 2016

(54) GENERATION OF DUCK CELL LINES

(71) Applicant: Valneva, Lyons (FR)

(72) Inventors: Fabienne Guehenneux, Orvault (FR); Karine Moreau, Nantes (FR); Magali Esnault, Basse-Indre (FR); Majid Mehtali, Coueron (FR)

(73) Assignee: Valneva, Lyons (FR)

( * ) Notice: Subject to any disclaimer, the term of this patent is extended or adjusted under 35 U.S.C. 154(b) by 0 days.

(21) Appl. No.: 14/069,423

(22) Filed: Nov. 1, 2013

(65) Prior Publication Data

US 2014/0154741 A1 Jun. 5, 2014

Related U.S. Application Data

(62) Division of application No. 12/597,486, filed as application No. PCT/EP2008/054912 on Apr. 23, 2008, now abandoned.

(30) Foreign Application Priority Data

Apr. 24, 2007 (EP) .................................. 07300979

(51) Int. Cl.
| | | |
|---|---|---|
| C12N 5/00 | (2006.01) | |
| C12N 5/0735 | (2010.01) | |
| A61K 39/12 | (2006.01) | |
| A61K 39/145 | (2006.01) | |
| A61K 39/17 | (2006.01) | |
| A61K 39/285 | (2006.01) | |
| C12N 7/00 | (2006.01) | |
| A61K 39/00 | (2006.01) | |

(52) U.S. Cl.
CPC .............. *C12N 5/0606* (2013.01); *A61K 39/12* (2013.01); *A61K 39/145* (2013.01); *A61K 39/17* (2013.01); *A61K 39/285* (2013.01); *C12N 7/00* (2013.01); *A61K 2039/525* (2013.01); *C12N 2501/105* (2013.01); *C12N 2501/115* (2013.01); *C12N 2501/125* (2013.01); *C12N 2501/13* (2013.01); *C12N 2501/23* (2013.01); *C12N 2710/24134* (2013.01); *C12N 2760/16034* (2013.01); *C12N 2760/18134* (2013.01)

(58) Field of Classification Search
USPC ....................................... 800/19, 21; 435/325
See application file for complete search history.

(56) References Cited

U.S. PATENT DOCUMENTS

| | | | |
|---|---|---|---|
| 5,162,215 A | 11/1992 | Bosselman et al. | |
| 5,340,740 A | 8/1994 | Petitte et al. | |
| 5,453,357 A | 9/1995 | Hogan | |
| 5,589,458 A | 12/1996 | Jameson et al. | |
| 5,656,479 A | 8/1997 | Petitte et al. | |
| 5,830,510 A | 11/1998 | Petitte et al. | |
| 6,114,168 A | 9/2000 | Samarut et al. | |
| 6,500,668 B2 | 12/2002 | Samarut et al. | |
| 6,656,479 B2 | 12/2003 | Brake et al. | |
| 6,998,266 B2 * | 2/2006 | Samarut et al. ............... | 435/406 |
| 7,432,101 B2 | 10/2008 | Guehenneux et al. | |
| 7,771,980 B2 | 8/2010 | Guehenneux et al. | |
| 8,148,132 B2 | 4/2012 | Mehtali et al. | |
| 8,962,311 B2 | 2/2015 | Valarche et al. | |
| 2002/0192815 A1 | 12/2002 | Samarut et al. | |
| 2004/0058441 A1 | 3/2004 | Pain et al. | |
| 2004/0077086 A1 | 4/2004 | Reiter et al. | |
| 2009/0239297 A1 | 9/2009 | Pain et al. | |
| 2010/0062489 A1 | 3/2010 | Guehenneux et al. | |
| 2010/0111999 A1 | 5/2010 | Guehenneux et al. | |
| 2010/0221825 A1 | 9/2010 | Pain et al. | |
| 2010/0235937 A1 | 9/2010 | Valarche et al. | |
| 2011/0294209 A1 | 12/2011 | Pain et al. | |
| 2012/0238001 A1 | 9/2012 | Mehtali et al. | |

FOREIGN PATENT DOCUMENTS

| | | |
|---|---|---|
| CN | 1826406 | 8/2006 |
| EP | 1 149 899 A1 | 10/2001 |
| EP | 0787180 B1 | 9/2002 |
| JP | 5-227947 A | 9/1993 |
| WO | WO 90/01541 A1 | 2/1990 |
| WO | WO 93/15185 A1 | 8/1993 |
| WO | WO 93/23528 A1 | 11/1993 |
| WO | WO 94/03585 A1 | 2/1994 |
| WO | WO 98/15614 | 4/1994 |
| WO | WO 96/12793 A1 | 5/1996 |
| WO | WO 99/06533 A1 | 2/1999 |
| WO | WO 99/06534 A1 | 2/1999 |
| WO | WO 00/03000 | 1/2000 |
| WO | WO 00/47717 A1 | 8/2000 |
| WO | WO 01/26294 A1 | 4/2001 |

(Continued)

OTHER PUBLICATIONS

Pain (Development, 1996, vol. 122, No. 8, p. 2339-2348).*
Trentin (PNAS, Mar. 30, 2004, vol. 101, No. 13, p. 4495-4500).*
Horiuchi, J Biol Chem. 279(23):24514-20, 2004).*
Petitte, Mech. Dev. 2004, vol. 121, No. 9, p. 1159-1168, see p. 1161-1162.*
[No Author Listed], Bird Classifications/families. Mar. 2, 2009.
Acloque et al., Identification of a new gene family specifically expressed in chicken embryonic stem cells and early embryo. Mech Dev. May 2001;103(1-2):79-91.
Bosselman et al., Transmission of exogenous genes into the chicken. J Reprod Fertil Suppl. 1990;41:183-95.
Carsience et al., Germline chimeric chickens from dispersed donor blastodermal cells and compromised recipient embryos. Development. Feb. 1993;117(2):669-75.
Chang et al., Germ line chimera produced by transfer of cultured chick primordial germ cells. Cell Biol Int. Jul. 1995;19(7):569-76.
Chang et al., Production of germline chimeric chickens by transfer of cultured primordial germ cells. Cell Biol Int. Aug. 1997;21(8):495-9.
Chino et al., Skin reaction to yellow fever vaccine after immunization with rabies vaccine of chick embryo cell culture origin. Jpn J Infect Dis. Apr. 1999;52(2):42-4.
Crocker et al., Isolation and characterization of resident stromal macrophages and hematopoietic cell clusters from mouse bone marrow. J Exp Med. Sep. 1, 1985;162(3):993-1014.

(Continued)

*Primary Examiner* — Michael Wilson
(74) *Attorney, Agent, or Firm* — Wolf, Greenfield & Sacks, P.C.

(57) ABSTRACT

The present invention relates to the development and manufacturing of viral vaccines. In particular, the invention relates to the field of industrial production of viral vectors and vaccines, more in particular to the use of avian embryonic stem cells, preferably the EBx® cell line derived from duck embryonic stem cells, for the production of viral vectors and viruses. The invention is particularly useful for the industrial production of viral vaccines to prevent viral infection of humans and animals.

11 Claims, 15 Drawing Sheets

(56) References Cited

FOREIGN PATENT DOCUMENTS

Figure 2:
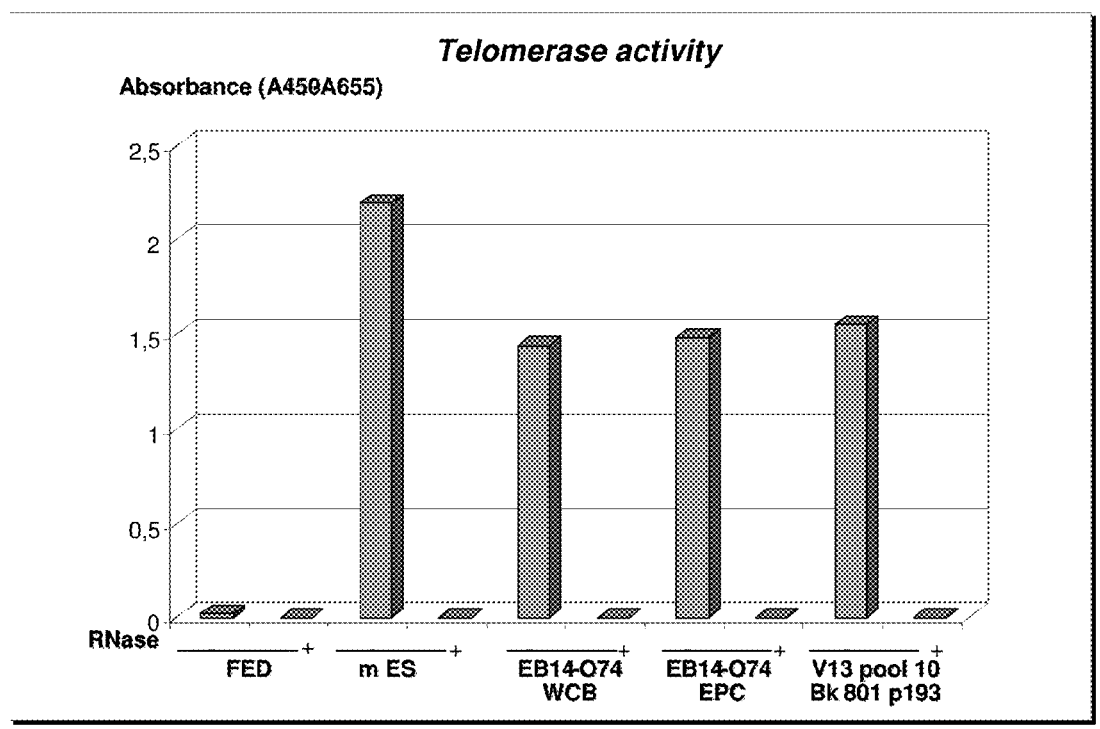

| WO | WO 03/076601 | 9/2003 |
|---|---|---|
| WO | WO 2005/007840 | 1/2005 |
| WO | WO 2006/108846 A1 | 10/2006 |
| WO | WO 2007/135133 | 11/2007 |
| WO | WO 2008/129058 | 10/2008 |

OTHER PUBLICATIONS

De Paulsen et al., Role of transforming growth factor-alpha in von Hippel—Lindau (VHL)$^{-/-}$ clear cell renal carcinoma cell proliferation: a possible mechanism coupling VHL tumor suppressor inactivation and tumorigenesis. Proc Natl Acad Sci U S A. Feb. 13, 2001;98(4):1387-92. Epub Feb. 6, 2001.

Drexler et al., Highly attenuated modified vaccinia virus Ankara replicates in baby hamster kidney cells, a potential host for virus propagation, but not in various human transformed and primary cells. J Gen Virol. Feb. 1998;79 ( Pt 2):347-52.

Etches et al., Contributions to somatic and germline lineages of chicken blastodermal cells maintained in culture. Mol Reprod Dev. Nov. 1996;45(3):291-8.

Etches et al., Manipulation of blastodermal cells. Poult Sci. Aug. 1997;76(8):1075-83.

Ettenberg et al., cbl-b inhibits epidermal growth factor receptor signaling. Oncogene. Mar. 11, 1999;18(10):1855-66.

Fayette et al., Human dendritic cells skew isotype switching of CD40-activated naive B cells towards IgA1 and IgA2. J Exp Med. Jun. 2, 1997;185(11):1909-18.

Ferlin-Bezombes et al., IFN-alpha is a survival factor for human myeloma cells and reduces dexamethasone-induced apoptosis. J Immunol. Sep. 15, 1998;161(6):2692-9.

Forster et al., Tetracycline-inducible expression systems with reduced basal activity in mammalian cells. Nucleic Acids Res. Jan. 15, 1999;27(2):708-10.

Gardner et al., Reflections on the biology of embryonic stem (ES) cells. Int J Dev Biol. Apr. 1997;41(2):235-43.

Gerner et al., Heat-inducible vectors for use in gene therapy. Int J Hyperthermia. Mar.-Apr. 2000;16(2):171-81.

Gey et al., Long-term growth of chicken fibroblasts on a collagen substrate. Exp Cell Res. Mar. 15, 1974;84(1):63-71.

Hagihara et al., Long-term functional assessment of encapsulated cells transfected with Tet-On system. Cell Transplant. Jul.-Aug. 1999;8(4):431-4.

Hahnel et al., The distribution of two cell surface determinants of mouse embryonal carcinoma and early embryonic cells. J Reprod Immunol. Feb. 1987;10(2):89-110.

Halloran et al., Laser-induced gene expression in specific cells of transgenic zebrafish. Development. May 2000;127(9):1953-60.

Huang et al., Expression of green fluorescent protein in oligodendrocytes in a time- and level-controllable fashion with a tetracycline-regulated system. Mol Med. Feb. 1999;5(2):129-37.

Kaaden et al., Establishment and characterization of chicken embryo fibroblast clone LSCC-H32. In Vitro. Oct. 1982;18(10):827-34.

Karagenç et al., Soluble factors and the emergence of chick primordial germ cells in vitro. Poult Sci. Jan. 2000;79(1):80-5.

Kawase et al., Strain difference in establishment of mouse embryonic stem (ES) cell lines. Int J Dev Biol. Jun. 1994;38(2):385-90.

Kemler et al., Reactivity of monoclonal antibodies against intermediate filament proteins during embryonic development. J Embryol Exp Morphol. Aug. 1981;64:45-60.

Kempe, Smallpox vaccination of eczema patients with attenuated live vaccinia virus. Yale J Biol Med. Aug. 1968;41(1):1-12.

Kingsley et al., Infectious laryngotracheitis virus, an alpha herpesvirus that does not interact with cell surface heparan sulfate. Virology. Apr. 10, 1999;256(2):213-9.

Linial, A line of ring-necked pheasant cells susceptible to infection by avian oncornaviruses. Virology. Sep. 1976;73(2):548-52.

Liu et al., Lac/Tet dual-inducible system functions in mammalian cell lines. Biotechniques. Apr. 1998;24(4):624-8, 630-2.

Love et al., Transgenic birds by DNA microinjection. Biotechnology (N Y). Jan. 1994;12(1):60-3.

Maruyama et al., The antigenicity of chicken embryo fibrosis cell passaged strains of Japanese encephalitis viruses. Journal of Infection and Chemotherapy, vol. 60, pp. 251-256 (1986).

Matsui et al., Derivation of pluripotential embryonic stem cells from murine primordial germ cells in culture. Cell. Sep. 4, 1992;70(5):841-7.

Mullins et al., Transgenesis in the rat and larger mammals J Clin Invest. Apr. 1, 1996;97(7):1557-60.

Nazerian, An updated list of avian cell lines and transplantable tumours. Avian Pathol. 1987;16(3):527-44.

Ogura et al., Establishment of two chick embryo fibroblastic cell lines. Gann. May 1984;75(5):410-4.

Petitte et al., Production of somatic and germline chimeras in the chicken by transfer of early blastodermal cells. Development. Jan. 1990;108(1):185-9.

Piquet-Pellorce et al., Are LIF and related cytokines functionally equivalent? Exp Cell Res. Aug. 1994;213(2):340-7.

Rang et al., The tetracycline-responsive promoter contains functional interferon-inducible response elements. Nucleic Acids Res. Mar. 1, 2000;28(5):1120-5.

Shafren et al., Pathogenesis of avian encephalomyelitis viruses. J Gen Virol. Nov. 1991;72 (Pt 11):2713-9.

Solter et al., Monoclonal antibody defining a stage-specific mouse embryonic antigen (SSEA-1). Proc Natl Acad Sci U S A. Nov. 1978;75(11):5565-9.

Thoraval et al., Germline transmission of exogenous genes in chickens using helper-free ecotropic avian leukosis virus-based vectors. Transgenic Res. Nov. 1995;4(6):369-77.

Thoraval et al., Somatic and germline chicken chimeras obtained from brown and white Leghorns by transfer of early blastodermal cells. Poult Sci. Dec. 1994;73(12):1897-905.

Tsunekawa et al., Isolation of chicken vasa homolog gene and tracing the origin of primordial germ cells. Development. Jun. 2000;127(12):2741-50.

Uchida et al., Rapid and sustained hematopoietic recovery in lethally irradiated mice transplanted with purified Thy-1.11$^{lo}$ Lin$^-$ Sca-1$^-$ hematopoietic stem cells. Blood. Jun. 15, 1994;83(12):3758-79.

Van De Lavoir et al., Germline transmission of genetically modified primordial germ cells. Nature. Jun. 8, 2006;441(7094):766-9.

Van De Lavoir et al., High-grade transgenic somatic chimeras from chicken embryonic stem cells. Mech Dev. Jan. 2006;123(1):31-41. Epub Dec. 1, 2005.

Wang et al., Progress toward the culture and transformation of chicken blastodermal cells. Stem Cells. Jul. 2006;24(7):1638-45.

Wilkinson et al., Expression pattern of the mouse T gene and its role in mesoderm formation. Nature. Feb. 15, 1990;343(6259):657-9.

Yang et al., Use of avian cytokines in mammalian embryonic stem cell culture. Poult Sci. Jul. 1994;73(7):965-74.

Zhu et al., Production of human monoclonal antibody in eggs of chimeric chickens. Nat Biotechnol. Sep. 2005;23(9):1159-69. Epub Aug. 28, 2005.

Chang et al., Proliferation of chick primordial germ cells cultured on stroma cells from the germinal ridge. Cell Biol Int. Feb. 1995;19(2):143-9.

Chang et al., Simple method for isolation of primordial germ cells from chick embryos. Cell Biol Int Rep. Sep. 1992;16(9):853-7.

Dunwiddie et al., Presence of retrovirus reverse transcriptase-related gene sequences in avian cells lacking endogenous avian leukosis viruses. Proc Natl Acad Sci U S A. Aug. 1985;82(15):5097-101.

Enami et al., High-efficiency formation of influenza virus transfectants. J Virol. May 1991;65(5):2711-3.

Enami et al., Introduction of site-specific mutations into the genome of influenza virus. Proc Natl Acad Sci U S A. May 1990;87(10):3802-5.

Eyal-Giladi et al., From cleavage to primitive streak formation: a complementary normal table and a new look at the first stages of the development of the chick. I. General morphology. Dev Biol. Apr. 1976;49(2):321-37.

Ginsburg et al., Primordial germ cells of the young chick blastoderm originate from the central zone of the area pellucida irrespective of the embryo-forming process. Development. Oct. 1987;101(2):209-19.

(56) References Cited

OTHER PUBLICATIONS

Hamburger, A serie of normal stages in the development of chick embryo. J. Morphol. vol. 88, pp. 49-92 (1951).

Horiuchi et al., Chicken leukemia inhibitory factor maintains chicken embryonic stem cells in the undifferentiated state. J Biol Chem. Jun. 4, 2004;279(23):24514-20. Epub Mar. 25, 2004.

Hussain et al., Identification and characterization of avian retroviruses in chicken embryo-derived yellow fever vaccines: investigation of transmission to vaccine recipients. J Virol. Jan. 2003;77(2):1105-11.

Johnson et al., Characterization of endogenous avian leukosis viruses in chicken embryonic fibroblast substrates used in production of measles and mumps vaccines. J Virol. Apr. 2001;75(8):3605-12.

Karagenç et al., Origin of primordial germ cells in the prestreak chick embryo. Dev Genet. 1996;19(4):290-301.

Kemble et al., Novel generations of influenza vaccines. Vaccine. May 1, 2003;21(16):1789-95.

Kempe et al., Smallpox vaccination of eczema patients with a strain of attenuated live vaccinia (CVI-78). Pediatrics. Dec. 1968;42(6):980-5.

Kyhse-Andersen, Electroblotting of multiple gels: a simple apparatus without buffer tank for rapid transfer of proteins from polyacrylamide to nitrocellulose. J Biochem Biophys Methods. Dec. 1984;10(3-4):203-9.

Laemmli, Cleavage of structural proteins during the assembly of the head of bacteriophage T4. Nature. Aug. 15, 1970;227(5259):680-5.

Lovatt et al., High throughput detection of retrovirus-associated reverse transcriptase using an improved fluorescent product enhanced reverse transcriptase assay and its comparison to conventional detection methods. J. Virol. Methods. 1999;82:185-200.

Luytjes et al., Amplification, expression, and packaging of foreign gene by influenza virus. Cell. Dec. 22, 1989;59(6):1107-13.

Naito et al., Production of germline chimeric chickens, with high transmission rate of donor-derived gametes, produced by transfer of primordial germ cells. Mol Reprod Dev. Oct. 1994;39(2):153-61.

Nieuwkoop et al., The migration of the primordial germ cells. London : Cambridge University Press, pp. 113-127 (1979).

Pain et al., Long-term in vitro culture and characterisation of avian embryonic stem cells with multiple morphogenetic potentialities. Development. Aug. 1996;122(8):2339-48.

Petitte et al., The origin of the avian germ lie and transgenesis in birds. Poultry science vol. 76, pp. 1084-1092 (1997).

Petitte J. N. et al., Avian pluripotent stem cells. Mech dev. vol. 121, pp. 1159-1168 (2004).

Reed et al., A simple method of estimating fifty percent endpoints. Am. J. Hyg. vol. 27, pp. 493-497 (1938).

Resnick et al., Phylogenetic distribution of the novel avian endogenous provirus family EAV-0. J Virol. Oct. 1990;64(10):4640-53.

Sellier et al., Comparative staging of embryo development in chicken, turkey, duck, goose, guinea Fowl, and japanese quail assessed from five hours after fertilization through seventy-two hours of incubation. J. Appl. Poult. Res. vol. 15, pp. 219-228 (2006).

Smith et al., Buffalo rat liver cells produce a diffusible activity which inhibits the differentiation of murine embryonal carcinoma and embryonic stem cells. Dev Biol. May 1987;121(1):1-9.

Sugimoto et al., Characteristics of an attenuated vaccinia virus strain, LC16m0, and its recombinant virus vaccines. Vaccine. Jun. 1994;12(8):675-81.

Tartaglia et al. NYVAC: A highly attenuated strain of vaccinia virus. Virology. May 1992;188(1):217-32.

Trentin et al., Self-renewal capacity is a widespread property of various types of neural crest precursor cells. Proc Natl Acad Sci U S A. Mar. 30, 2004;101(13):4495-500. Epub Mar. 15, 2004.

Tsang et al., Evidence of avian leukosis virus subgroup E and endogenous avian virus in measles and mumps vaccines derived from chicken cells: investigation of transmission to vaccine recipients. J Virol. Jul. 1999;73(7):5843-51.

Weissmahr et al., Reverse transcriptase activity in chicken embryo fibroblast culture supernatants is associated with particles containing endogenous avian retrovirus EAV-0 RNA. J. Virol. vol. 71, pp. 3005-3012 (1997).

Wood et al., An improved single-radial-immunodiffusion technique for the assay of influenza haemagglutinin antigen : application for potency determinations of inactivated whole virus and subunit vaccines. J. Biol. Stand. vol. 5, pp. 237-247 (1977).

Yasuda et al., A method to obtain avian germ-line chimaeras using isolated primordial germ cells. J Reprod Fertil. Nov. 1992;96(2):521-8.

Berger et al., Self renewal of embryonic stem cells in the absence of feeder cells and exogenous leukaemia inhibitory factor. Growth Factors. 1997;14(2-3):145-59.

Bradley et al., Modifying the mouse: design and desire. Biotechnology (N Y). May 1992;10(5):534-9.

Doetschman, Gene Transfer in Embryonic Stem Cells. Transgenic Animal technology: a laboratory handbook. Pinkert, C, ed., Academic Press, Inc., San Diego. 1994:134-146.

Freshney, Culture of animal cells: a manual of basic technique and specialized applications. 6th edition. 2010; Chapter 12, Subculture and cell lines, pp. 187-196.

Galli et al., Embryonic stem cells in farm animals. Zygote. Nov. 1994;2(4):385-9.

Godin et al., Effects of the steel gene product on mouse primordial germ cells in culture. Nature. Aug. 29, 1991;352(6338):807-9.

Hayman et al., Self-renewal and differentiation of normal avian erythroid progenitor cells: regulatory roles of the TGF alpha/c-ErbB and SCF/c-Kit receptors. Cell. Jul. 16, 1993;74(1):157-69.

Pain et al., Chicken embryonic stem cells and transgenic strategies. Cells Tissues Organs. 1999;165(3-4):212-9.

Sang, Transgenic chickens—methods and potential applications. Trends Biotechnol. Oct. 1994;12(10):415-20.

Seamark, Progress and emerging problems in livestock transgenesis: a summary perspective. Reprod Fertil Dev. 1994;6(5):653-7.

Simkiss, Transgenic birds. Animals with novel genes. 1994;106-137.

Slager et al., Transforming growth factor-beta in the early mouse embryo: implications for the regulation of muscle formation and implantation. Dev Genet. 1993;14(3):212-24.

Soodeen-Karamath et al., Apparent absence of oct 3/4 from the chicken genome. Mol Reprod Dev. Feb. 2001;58(2):137-48.

Tajima et al., Production of germ line chimera by transfer of primordial germ cells in the domestic chicken (*Gallus domesticus*). Theriogenology. Sep. 1993;40(3):509-19.

Terstappen et al., Analysis of bone marrow stem cell. Blood Cells. 1994;20(1):45-61; discussion 61-3.

Twal et al., Anti-retinoic acid monoclonal antibody localizes all-trans-retinoic acid in target cells and blocks normal development in early quail embryo. Dev Biol. Apr. 1995;168(2):225-34.

Wall, Transgenic livestock: Progress and prospects for the future. Theriogenology. 1996;45:57-68.

Zhou et al., Production of a hybridoma cell line secreting retinoic acid-specific monoclonal antibody. J Immunol Methods. Apr. 25, 1991;138(2):211-23.

* cited by examiner

Fig. 1A
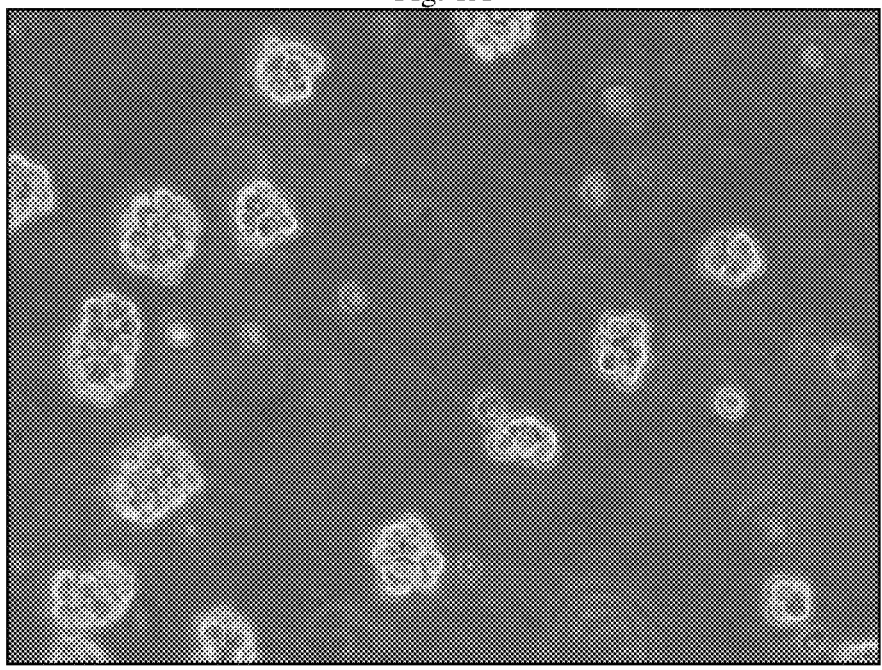
Fig. 1B
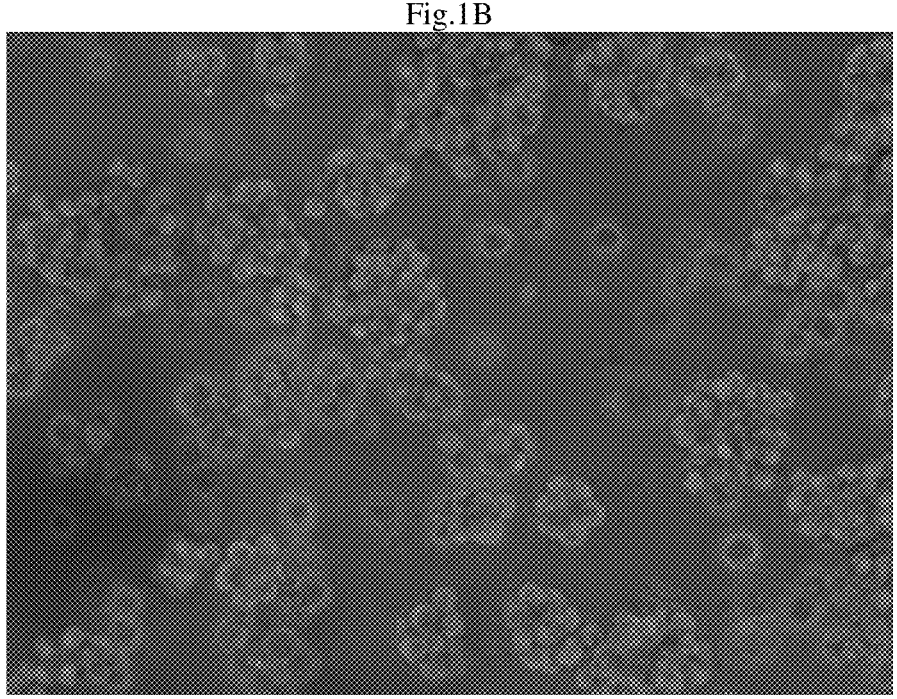
FIGURE 1

Figure 4A
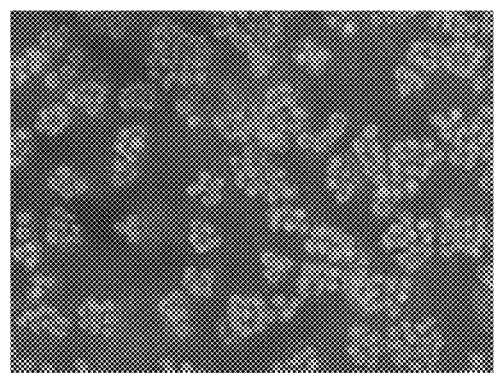
Figure 4B
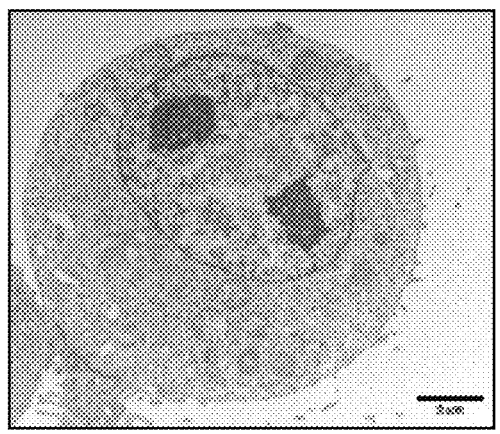
Figure 4C
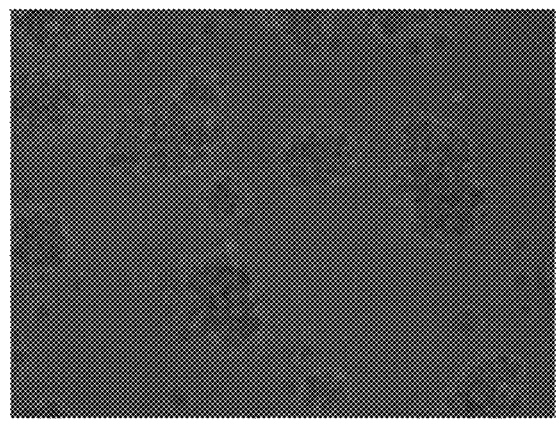
FIGURE 4

Figure 10A
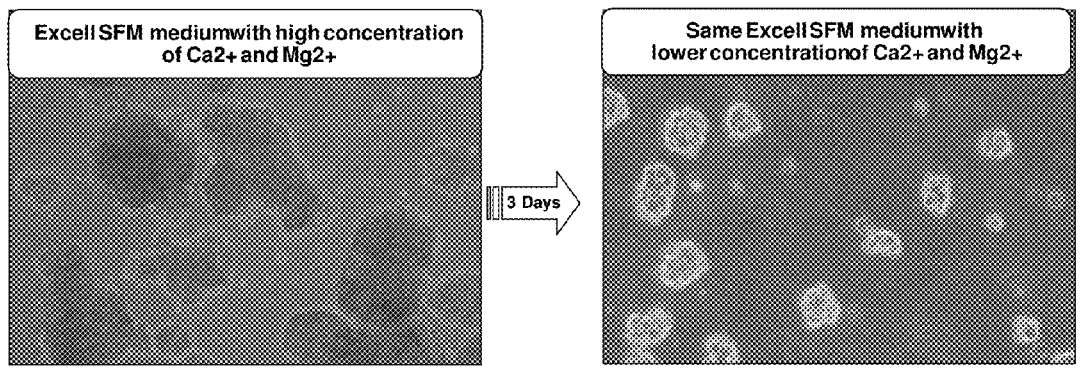
Figure 10B
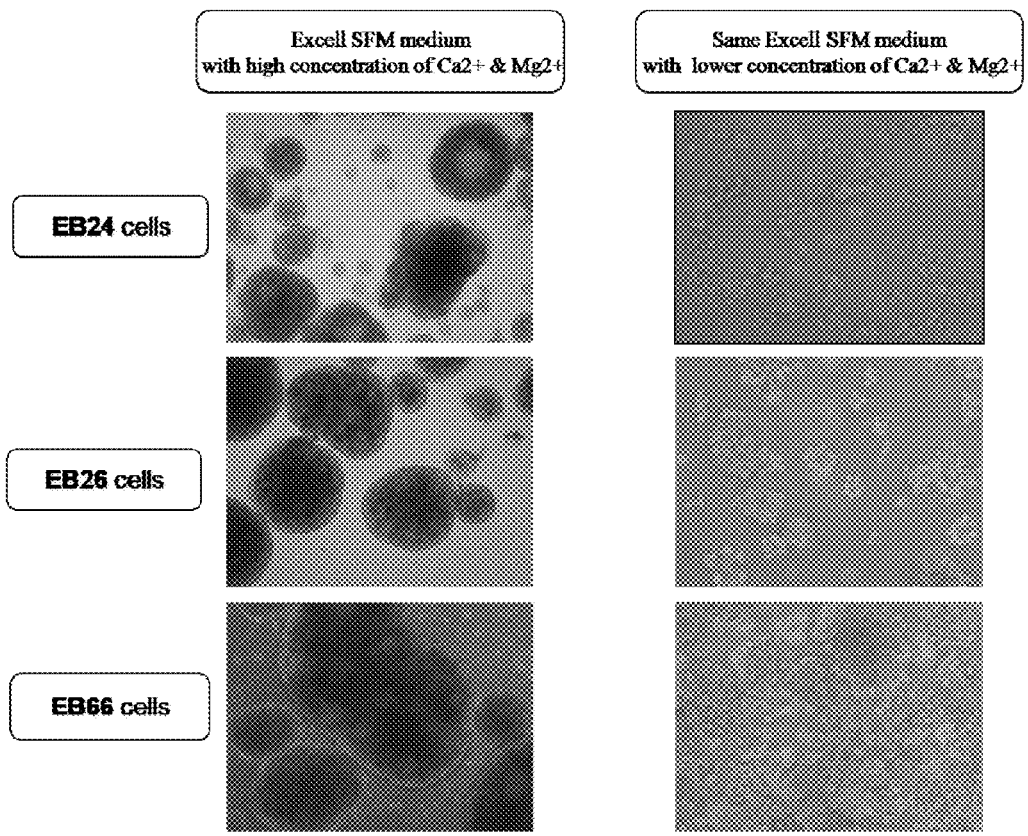
FIGURE 10

Figure 15A :
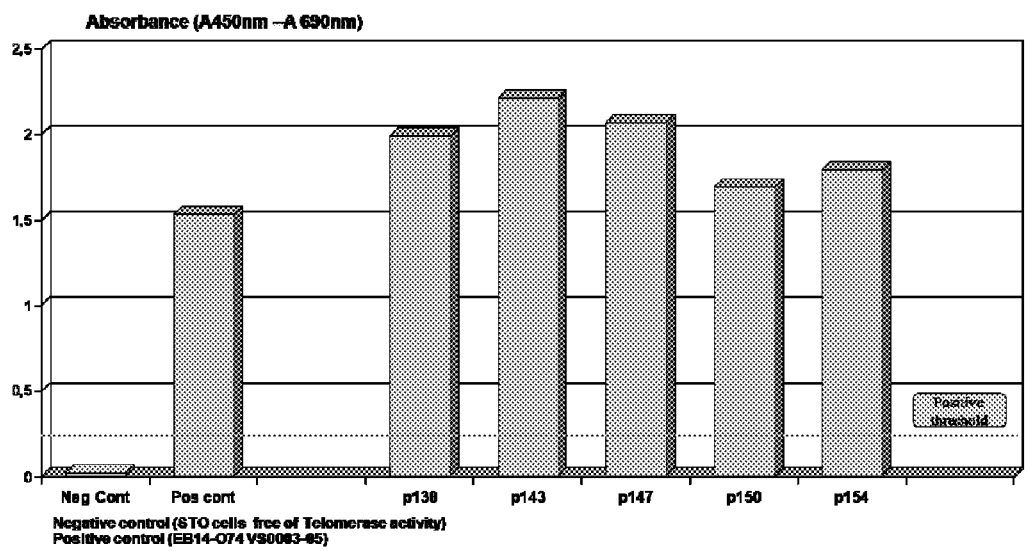
Figure 15B :
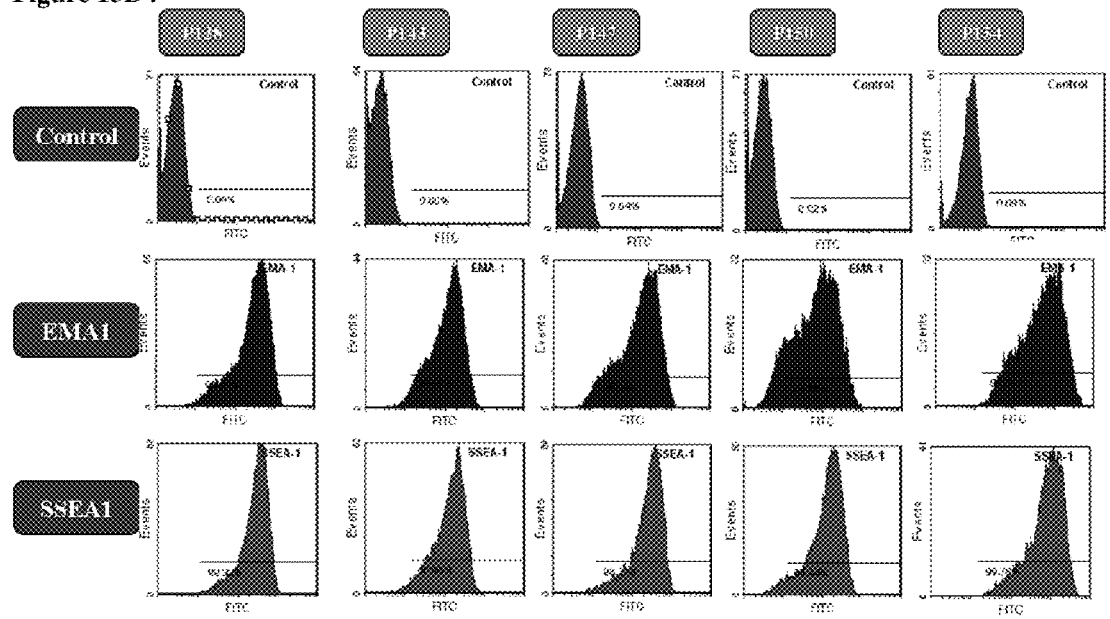
FIGURE 15

GENERATION OF DUCK CELL LINES

CROSS-REFERENCE TO RELATED APPLICATIONS

This application is a divisional of U.S. application Ser. No. 12/597,486, filed on Oct. 23, 2009, which is a national stage filing under 35 U.S.C. §371 of International Application No. PCT/EP2008/054912, filed on Apr. 23, 2008, which claims the priority of European Application No. 07300979.7, filed Apr. 24, 2007, the entire contents of which are incorporated by reference herein.

FIELD OF THE INVENTION

The present invention relates to the development and manufacturing of viral vaccines. In particular, the invention relates to the field of industrial production of viral vectors and vaccines, more specifically to the use of duck cell lines derived from embryonic stem cells that are free of avian endogenous retrovirus, for the production of viral vectors and viruses. The invention is particularly useful for the industrial production of viral vaccines to prevent viral infection of humans and animals.

BACKGROUND

Vaccines effectively reduce and prevent death and disease from many viral infections such as for example flu, measles, mumps, smallpox, yellow fever.

Many viral vaccines are currently produced on embryonated chicken eggs or on primary chicken embryo fibroblasts isolated from chicken embryos. However, vaccine production occasionally has been complicated by inadvertent contamination with adventitious agents that may have originated from avian cell substrates used to propagate vaccine strains. Indeed reverse-transcriptase (RT) activity, an indication of the presence of retroviruses, was detected in chick cell-derived live, attenuated vaccines including those produced by European and US manufacturers for yellow fever, Measles and Mumps (Hussain et al., 2003, J. Virol 77:1105-1111; Johnson et Heneine, 2001, J. Virol., 75:3605-3612). Investigations of the origin of RT activity in those vaccines found evidence of particles containing RNA from endogenous avian leucosis virus (ALV-E) and endogenous avian virus (EAV) (Johnson et Heneine, 2001, J. Virol 75:3605-3612; Tsang et al., 1999, J. Virol 73:5843-5851; Weissmahr et al., 1997, J. Virol 71:3005-3012).

Both ALV-E and EAV are members of endogenous retrovirus families present in the chicken germ line. ALV-E are expressed from ev loci, which are inheritable proviral elements. Based on their envelope sequences, ALV-E are differentiated from ALV subgroups A to D and J which are exogenously acquired infections. While exogenous ALVs cause several neoplastic diseases, such as myocarditis and osteopetrosis in infected chickens, ALV-E are not known to be pathogenic to chickens. The lack of oncogenic potential with ALV-E infections may be attributed to the absence of both a viral oncogene and enhancer activity in the endogenous long terminal repeat (LTR). More than 20 different ev loci have been identified in White Leghorn chickens (ev-1 to ev-22). Ev loci designations are assigned in the order discovered and are phenotypically categorized with regard to the gene products they express and their capacity to generate infectious particles. ALV-E phenotypes conferred by ev loci range from structurally and enzymatically complete infectious particles to structurally or enzymatically (RT-) defective to no detectable viral protein expression. Most ev loci are structurally incomplete and therefore do not encode all sequences necessary for production of infectious virus particles. Chicken strain, named ev-0, has been obtained by breeding to be resistant to ALV-E. Line-0 chickens are lacking ev loci (i.e ev-0) but EAV proviral sequences are present in the genome line 0 chickens (Dunwiddie and Far as, 1985, Proc Natl. Acad. Sci. USA, 82: 5097-5101).

Little is known about the EAV family, which is distinct from but related to ALV family. EAV elements are present in at least 50 copies per chicken genome. However, none of the known EAV sequences represents full-length and intact retroviral genomes and no infectious EAV isolates have been yet identified. However EAV have been shown to be highly expressed in embryonic cells derived from the avian genus, *gallus*. Weissmahr et al. (1997, J. Virol 71:3005-3012) have shown that particles from the EAV endogenous retrovirus family are most likely responsible for a large portion of the particles-associated RT activity found in the supernatants of cultured chick embryo fibroblasts.

The risk of inadvertent transmission is particularly high for live attenuated virus vaccine since they cannot be subjected to an inactivation procedure and most of them are injected into human, thus by-passing non-specific immune protection mechanisms. Thus, to ensure safety of vaccines for animal and human use, the cell substrates for vaccine production have now to be tested for the presence of replication-competent retroviruses that could be passed to animal or human hosts during immunization (WHO technical reports Series, 1994).

On the other hands, embryonated chicken eggs and primary chicken embryo fibroblasts production systems are associated with several serious limitations, including:
a lengthy, cumbersome and resource-consuming manufacturing process that requires the procurement and quality control of large quantities of eggs or CEFs for each individual production campaign;
the need in many cases to use costly specific pathogen free (SPF) chicken embryos;
the risks of insufficient supply of eggs in cases of epidemic infections in donor chicken flocks;
the inflationist costs associated with the use of bovine sera originating from BSE-exempt countries;
the inability to use eggs for the propagation of viruses that are highly virulent and lethal to chickens.

There is therefore an urgent need to improve on the current viral vaccines production technologies based on eggs or chicken-embryonic fibroblasts. The development of cell-culture platforms as an alternative to the eggs and CEF production systems for the manufacture of viral vaccines is likely the most rapid and promising solution to overcome current vaccines production bottlenecks and time constrains. Moreover, the use of cell lines for manufacture of viral vaccines, instead of egg or CEF platforms, would have the additional following advantages in connection with the safety of the vaccine: no antibiotic additives present in the vaccine formulation; no toxic preservatives (such as thiomersal) needed; reduced endotoxin levels, no egg allergy issue; no risk of adventitious agent/BSE by cell culture in protein and serum free media; higher purity of virus vaccine preparation.

Examples of cell lines for the production of viral vaccines are MDCK (cells derived from the kidney of Madin-Darby dog), PerC6 (cells derived from human embryonic retinal cells genetically modified by inserting the E1 genes from the human adenovirus type 5) developed by CRUCELL (Netherland)), VERO (cells derived from epithelial cells of kidney from African green monkey (*Cercopithecus aethiops*) isolate at the Chiba University in Chiba, Japan), BHK21 (Cells immortalized from baby hamster kidney cells). None of the cell lines available fulfil all the medical, regulatory and industrial requirements. For example, most of these cell lines are tumorigenic and there are important regulatory concern about the use of tumorigenic cells for the production of human vaccines; therefore, today the regulatory authorities are reluctant to approve tumorigenic cell substrates to produce mass vaccines. In addition, some of these cell lines are anchorage-dependant, which constitutes a serious hurdle for the industrial scaling-up of the vaccine production.

Therefore, there is a need to develop anchorage-independent cell lines, free of replication competent of retroviruses, that are non-tumorigenic and industrially compliant, which is susceptible to infection with a wide range of viruses. This is the purpose of the instant invention.

Thus, the inventor has taken advantage of its expertise in avian biology and in avian embryonic stem (ES) cells to undertake the development of novel stable duck cell lines that enables the efficient replication of a large group of human and veterinarian vaccines and vaccine candidates. By adapting a proprietary process (see WO 03/076601 and WO 05/007840), the inventor was able to generate a series of well characterized and documented duck cell lines (i.e the dEBx® cells) that are derived from duck ES cells, with no steps of genetic, chemical or viral immortalization and that do not produce replication-competent retroviruses in culture.

DESCRIPTION

The instant invention provides a process for obtaining continuous diploid avian cell lines, named EBx, derived from avian embryonic stem cells (ES), wherein said avian cell lines do not produce replication-competent endogenous retrovirus particles.

The cell lines of the invention are "continuous" because they have the characteristics to be cultured in vitro over an extended period of time. Advantageously, the cells of the invention are capable of proliferating for at least 50 generations, at least 75 generations, at least 100 generations, at least 125 generations, at least 150 generations, at least 175 generations, at least 200 generations, at least 250 generations. The 250 generations do not constitute a time limit because the cells obtained are still alive and can still be passaged for additional passages. Without to be bond by a theory, it is postulated that the cells of the invention can be cultured "continuously" as long as telomerase is expressed by the cells. Indeed, it is assumed that the high level of telomerase expression of avian cells of the invention is responsible for genetic stability (i.e avian cells of the invention are diploid) and the continuous cell growth.

By "passage" it is meant the transfer of transplantation of cells, with or without dilution, from one culture vessel to another. It is understood that any time cells are transferred from one vessel to another, a certain portion of the cells may be lost and therefore, dilution of cells, whether deliberate or not, may occur. This term is synonymous with the term 'sub-culture'. The passage number is the number of times the cells in the culture, that grow either in suspension or in adherence, have been sub-cultured or passed in a new vessel. This term is not synonymous with population doubling or generation which is the time needed by a cell population to replicate one time; that is to say, roughly the time for each cells of a population to replicate. For example, Avian ES cells of step a) of the invention have a population doubling time (PDT) of around >40 hours. The avian EBx cells of the invention have a PDT of around <30 hours; usually for EBx® cells, there is one passage every 3 generations.

By "diploid", it is mean that cells of the invention have two copies (2n) of each chromosome, usually one from the mother and one from the father.

The fact that avian EBx® cell lines of the invention are continuous and diploid (i.e genetically stable) constitutes a remarkable and unique feature because these terms are usually antagonist. Thus, cancer cells and/or immortalized cells obtained by chemical, physical (U.V irradiation, X-ray or g-irradiation, . . . ) or genetic modification (virus transformation, oncogenes overexpression, . . . ) are continuous cells because they are able to replicate indefinitely into culture, but they are not genetically stable because they display polyploid karyotypes. On the other hand, primary cells such as chicken embryonic fibroblasts, MRCS, WI38 which are non-transformed cells, are not continuous because they have a finite life-span after few generation, but they are genetically stable (i.e diploid) cells.

In the present invention, the terms "cell line" and "cells" will be used indistinctly.

The term "avian, "bird", "ayes" or "ava" as used herein is intended to have the same meaning, and will be used indistinctly. "Birds" refer to any species, subspecies *or* race of organism of the taxonomic class <<ava>>. In a preferred embodiment, "birds" refer to any animal of the taxonomix order:

"Anseriformes" (i.e duck, goose, swan and allies). The order Anseriformes contains about 150 species of birds in three families: the Anhimidae (the screamers), Anseranatidae (the Magpie-goose), and the Anatidae, which includes over 140 species of waterfowl, among them the ducks, geese, and swans. All species in the order are highly adapted for an aquatic existence at the water surface. All are web-footed for efficient swimming (although some have subsequently become mainly terrestrial).

"Galliformes" (i.e chicken, quails, turkey, pheasant and allies). The Galliformes is an order of birds containing the chicken, turkeys, quails and pheasants. About 256 species are found worldwide.

"Columbiformes" (i.e Pigeon and allies). The bird order Columbiformes includes the very widespread doves and pigeons.

In the instant invention, by the term "endogenous retroviral particle" or "endogenous retrovirus particle", terms that could be used indistinctively, it is meant a retroviral particle or retrovirus encoded by and/or expressed from ALV-E or EAV proviral sequences present in some avian cell genomes. In the birds, ALV-E proviral sequences are known to be present in the genome of domestic chicken (except Line-0 chicken), red jungle fowl and Ringneck Pheasant. In the birds, EAV proviral sequences are known to be present in all genus *gallus* that includes domestic chicken, Line-0 chicken, red jungle fowl, green jungle fowl, grey jungle fowl, Ceylonese jungle fowl and allies) (see Resnick et al., 1990, J. Virol., 64:4640-4653).

According to a preferred embodiment, the bird of the invention are selected among the birds that does not comprises ALV-E and EAV proviral sequences in its genome. A man skilled in the art is able to determine whether ALV-E and EAV sequences are present in a bird genome (Johnson and Heneine, 2001; Weissmahr et al., 1996). Preferably the bird is selected in the group comprising Anseriformes (i.e duck, goose, swan), turkeys, quails, Japanese quail, Guinea fowl, Pea Fowl. Therefore, cells derived from such bird do not produce replication-competent endogenous ALV-E and/or EAV particles. In a preferred embodiment, the bird of the present invention is selected among the group comprising ducks, geese, swans, turkeys, quails and Japanese quails, Guinea Fowls and Pea Fowls. According to a more preferred embodiment, the bird is a duck, more preferably a Pekin or Muscovy ducks. According to a more preferred embodiment, the bird is a Pekin duck. Therefore, the instant invention provides a process for obtaining continuous diploid duck cell lines derived from embryonic stem cells (ES), wherein said duck cell lines do not produce replication-competent endogenous retrovirus particles. According to a second preferred embodiment, the bird of the invention are selected among the birds that does not comprises complete ALV-E proviral sequences in its genome but eventually EAV proviral sequences. A man skilled in the art is able to determine whether partial or complete ALV-E and EAV sequences are present in a bird genome (Johnson and Heneine, 2001). Several chicken strains have been selected by breeding that do not contain complete ALV-E proviral sequences (i.e: ev-0 strain) and therefore do not produce infectious ALV-E retroparticles, such as:

Line 0 domestic chicken of East Lansing USDA poultry stock (ELL-0 strain). The East Lansing Line-0 chickens do not contain any endogenous viral (ev) loci related to ALV (Dunwiddie and Far as, 1985).

Lines DE and PE11 from Institut National de la Recherche Agronomique (Domaine de Magneraud, Surgères, France).

Therefore, cells derived from ev-0 birds do not produce replication-competent endogenous ALV-E particles. According to a preferred embodiment, the bird is an ev-0 domestic chicken (*Gallus Gallus* subspecies *domesticus*), preferably selected among ELL-0, DE and PE11.

Usually, ev-0 chickens still contain EAV proviral sequence but so far no infectious EAV isolates have been identified. Therefore, the instant invention provides a process for obtaining continuous diploid chicken cell lines derived from embryonic stem cells (ES) of ev-0 chicken strains, wherein said ev-0 chicken cell lines do not produce replication-competent endogenous retrovirus particles.

According to a third embodiment, the bird of the invention are selected among the birds that comprise complete and/or incomplete ALV-E and EAV proviral sequences in its genome but that are unable to produce replication competent ALV-E and EAV retroparticles. A man skilled in the art is able to determine whether ALV-E and/or EAV infectious and/or non-infectious retroparticles are produced from a bird cells (Johnson and Heneine, 2001; Weissmahr et al., 1996). Preferably the bird is selected in the group comprising specific pathogen free (SPF) chicken, preferably from Valo strain (Lohman) or Line 22 (SPAFAS).

By "replication-competent" it is meant that the endogenous retroviral particles are infectious, that is to say that such retroviral particles are able to infect and to replicate in avian cells of the invention.

The process of establishment of continuous diploid avian cell lines, named EBx®, of the invention comprises two steps:
a) isolation, culture and expansion of embryonic stem cells from birds that do not contain complete endogenous proviral sequences, or a fragment thereof, susceptible to produce replication competent endogenous retroviral particles, more specifically EAV and/or ALV-E proviral sequences or a fragment thereof, in a complete culture medium containing all the factors allowing their growth and in presence of a feeder layer and supplemented with animal serum; optionally, said complete culture medium may comprise additives, such as additional amino-acids (i.e glutamine, non essential amino acids . . . ), sodium pyruvate, beta-mercaptoethanol, vitamins, protein hydrolyzate of non-animal origin (i.e yeastolate, plant hydrolyzates (soy, wheat, . . . );
b) passage by modifying the culture medium so as to obtain a total withdrawal of said factors, said feeder layer and said serum, and optionally said additives, and further obtaining adherent or suspension avian cell lines, named EBx®, that do not produce replication-competent endogenous retrovirus particles, capable of proliferating over a long period of time, in a basal medium in the absence of exogenous growth factors, feeder layer and animal serum.

The modification of the culture medium of step b) of the process of establishment EBx® cell lines, so as to obtain progressive or total withdrawal of growth factors, serum and feeder layer, can be made simultaneously, successively or separately. The sequence of the weaning of the culture medium may be chosen among:
feeder layer/serum/growth factors;
feeder layer/growth factors/serum;
serum/growth factors/feeder layer;
serum/feeder layer/growth factors;
growth factors/serum/feeder layer;
growth factors/feeder layer/serum.

In a preferred embodiment, the sequence of the weaning is growth factors/feeder layer/serum.

In a preferred embodiment, the withdrawal of additives such as sodium pyruvate, non essential amino acids (NNEA), vitamins, yeastolate are performed after the weaning of feeder layer and before the weaning of serum. Preferably, the withdrawal of yeastolate is performed after the withdrawal of sodium pyruvate, NNEA and vitamins.

According to a preferred embodiment, the avian embryonic stem cells according to step a) of the invention are collected from avian embryo at oviposition, that is to say when the egg is laid. According to Sellier et al. (2006, J. Appl. Poult. Res., 15:219-228), oviposition corresponds to the following development stages according to Eyal-Giladi's classification (EYAL-GILADI's classification: EYAL-GILADI and KOCHAN, 1976, <<From cleavage to primitive streak formation: a complementary normal table and a new look at the first stages of the development in the chick>>. "General Morphology" Dev. Biol. 49:321-337):
Muscovy duck (also called Barbari duck): stage VII
Guinea fowl: stage VII-VIII
Turkey: stage VII-VIII
Pekin duck: stage VIII
Chicken: Stage X
Japanese Quail: stage XI
Goose: stage XI Preferably, the duck embryonic stem (ES) cells of step a) are obtained by dissociating Pekin duck embryo(s) at around stage VIII (oviposition) of Eyal-Giladi's classification. If the laid egg collected at oviposition is not enough developed to collect embryonic stem cells, the laid egg may be further incubated between several hours (overnight) to one to two days to mature the embryo. According to a second embodiment the duck embryonic stem (ES) cells of step a) is from a Muscovy duck. At oviposition, Muscovy duck is not enough mature because it is around stage VII, therefore, the egg is incubated overnight to mature the egg up to stage VIII to X of Eyal-Giladi's classification.

Preferably, the chicken embryonic stem (ES) cells, preferably from ev-0 chicken strain, of step a) is obtained by dissociating embryo(s) at around stage X (oviposition) of Eyal-Giladi's classification.

Alternatively, the avian embryonic stem cells according to step a) of the invention are collected from embryo before oviposition. The main limitations encountered before oviposition is the fact that the egg has to be surgically removed from hens and that the amount of ES cells per embryo is less important. Moreover at very early stages of avian embryo development, ES cells are not well individualized rendering difficult in vitro culture of ES cells. A man skilled in the Art will be able to define the timeframe prior egg laying that allows to collect avian ES cells.

Alternatively, the avian embryonic stem cells according to step a) of the invention may be collected from avian embryo after oviposition up to hatching. However, avian embryonic stem cells will progressively enter into differentiation to generate differentiated tissues; therefore, it is preferred to collect avian ES not to long after the lay. A man skilled in the Art will be able to define the timeframe after egg laying that allows to collect avian embryonic stem cells.

According to another embodiment, the cells of step a) are a population of embryonic stem cells enriched in primordial germ cells (PGC). More preferably, the avian ES cells of step a) are purified PGCs. In avian species, Primordial Germ Cells arise from the central region of the blastoderm (Ginsburg and Eyal-Giladi, 1987 Development 101(2):209-19; Karagenc et al, 1996 Dev Genet 19(4):290-301; Petitte et al, 1997 Poultry Sci. 76(8):1084-92). Then they move to an anterior, extra-embryonic site, the germinal crescent until collected by the vasculature between 2.5 and 5 days of embryonic development to reach the germinal ridge. They colonize the germinal ridge where they eventually differentiate into oocytes or spermatocytes (Nieuwkoop and Sutasurya, 1979. *The Migration of the primordial germ cells. In: Primordial germ cell in Chordates. London: Cambridge University Press* p 113-127). Methods for isolation of PGCs from donor avian embryos have been reported in the literature and can easily be performed by one skilled in the art (See, e.g. JP924997 published sept. 7, 1993 Pub. No 05-227947; Chang et al. 1992. Cell Biol. Int. 19(2): 143-149; Naito et al. 1994 Mol. Reprod. Dev. 39: 153-161; Yasuda et al. 1992. J. Reprod. Fert. 96: 521-528; Chang et al. 1992 Cell Biol. Int. Reporter 16(9): 853-857). According to an embodiment, PGCs are collected from embryonic blood collected from the dorsal aorta of a chicken embryo at stage 12-14 of Hamburger & Hamilton's classification (Hamburger & Hamilton 1951 A series of normal stages in the development of chick embryo. J. Morphol. 88: 49-92). In another preferred embodiment, PGCs were collected from the germinal crescent by mechanical dissection of chicken embryo or from the gonads. However, as discussed above, others methods for isolating PGCs are known and can alternatively be used.

These avian embryonic stem cells are characterized by a slow doubling time comprises between 48 to 72 hours in culture at 39° C.

Without to be bound by a theory, the defined cell culture conditions of avian ES cells followed by the progressive weaning in grow factors, feeder layer, additives and serum, allow to adapt and select cells that maintain most of the desirable feature of ES cells (stability of karyotype, indefinite proliferation, expression of ES markers) but in addition display industrial-friendly characteristics like growth in suspension up to high cell densities in serum-free medium. Telomerase constitutes one of the most important ES markers. Due to the sustained and maintained telomerase expression over the cell passages, EBx® cell are continuous (i.e immortal) but in addition are genetically stable (i.e diploid).

More specifically, the present invention provides a process for obtaining continuous diploid avian cell lines derived from ES cells, wherein said avian cell lines do not produce replication competent endogenous retroviral particles, said process comprising the following steps of:

a) isolating bird embryo(s), preferably from duck or from ev-0 chicken, at a developmental stage comprises from around stage VI of Eyal-Giladi's classification (EYAL-GILADI's classification: EYAL-GILADI and KOCHAN, 1976, <<From cleavage to primitive streak formation: a complementary normal table and a new look at the first stages of the development in the chick>>. "General Morphology" Dev. Biol., 49:321-337) and before hatching, preferably around oviposition, wherein the genome of said bird does not contain endogenous proviral sequences susceptible to produce replication competent endogenous retroviral particles;

b) suspending avian embryonic stem (ES) cells obtained by dissociating embryo(s) of step a) in a basal culture medium supplemented with:
  Insulin Growth factor 1 (IGF-1) and Ciliary Neurotrophic factor (CNTF);
  animal serum; and
  optionally, growth factors selected in the group comprising interleukin 6 (IL-6), interleukin 6 receptor (IL-6R), Stem cell Factor (SCF) and Fibroblast Growth Factor (FGF);

c) seeding the suspension of ES cells obtained in step b) on a layer of feeder cells and further culturing the ES cells for at least one passage;

d) optionally withdrawing all the growth factors selected from the group comprising IL-6, IL-6R, SCF, FGF from the culture medium over a range of several passages from 1 to around 15 passages, preferably from 3 to around 15 passages and further culturing the avian ES cells for at least one passage. Preferably, the withdrawing of all the growth factors selected from the group comprising IL-6, IL-6R, SCF, FGF from the culture medium is performed simultaneously over one passage. Usually, the withdrawing of IL-6, IL-6R, SCF, FGF is performed at around passage 10 to 15;

e) withdrawing IGF-1 and CNTF from the culture medium and further culturing the avian ES cells for at least one passage. Preferably, the withdrawing of the growth factors selected from the group comprising IGF-1 and CNTF from the culture medium is performed simultaneously, over one passage. Usually, the withdrawing of IGF-1 and CNTF is performed at around passage No 15 to No 25. Alternatively, the withdrawing of IGF-1 and CNTF is performed by progressive decreasing over several passages (at least 2 passages and approximately up to 15 passages);

f) progressively decreasing the concentration of feeder cells in the culture medium so as to obtain a total withdrawal of feeder layer after several passages, and further culturing the cells;

g) optionally, progressively decreasing the concentration of additives in the culture medium so as to obtain a total withdrawal of additives after at least one passage; and, h) optionally, progressively decreasing the concentration of animal serum in the culture medium so as to obtain a total withdrawal of animal serum after several passages; and, i) obtaining adherent avian cell lines, named EBx®, derived from ES cells capable of proliferating in a basal medium in the absence of growth factors, feeder layer optionally without animal serum and additives, and wherein said continuous diploid avian cell lines do not produce replication-competent endogenous retrovirus particles;

j) optionally, further adapting said adherent avian EBx® cell lines to suspension culture conditions. The step of adaptation of cell culture to suspension can take place all along the process of establishment of EBx® cells. For example, with duck EBx® cells derived from Muscovy embryonic stem cells, the cells were adapted to the growth in suspension prior feeder layer withdrawal. For duck EB® cells (EB24, EB26, EB66) derived from Pekin duck, the cells were adapted to the growth in suspension prior animal serum withdrawal.

k) Optionally further subcloning said avian EBx® cells, for example by limit dilution.

In a preferred embodiment, the present invention relates to a process for obtaining continuous diploid avian cell lines, named EBx®, derived from avian embryonic stem cells (ES), wherein said avian cell lines do not produce replication-competent endogenous retrovirus particles, and said process comprising the steps of:

a) isolating bird embryo(s) at a developmental stage around oviposition, wherein the genome of said bird does not contain endogenous proviral sequences susceptible to produce replication competent endogenous retroviral particles;

b) suspending avian embryonic stem (ES) cells obtained by dissociating embryo(s) of step a) in a basal culture medium supplemented with at least:
Insulin Growth factor 1 (IGF-1) and Ciliary Neurotrophic factor (CNTF); and
mammalian serum such as foetal bovine serum;

c) seeding the suspension of ES cells obtained in step b) on a layer of feeder cells and further culturing the ES cells for at least one passage;

e) withdrawing IGF-1 and CNTF from the culture medium, and further culturing the cells for at least one passage;

f) progressively decreasing the concentration of feeder cells in the culture medium so as to obtain a total withdrawal of feeder layer after several passages, and further culturing the cells;

g) progressively decreasing the concentration of said mammalian serum in the culture medium so as to obtain a total withdrawal of mammalian serum after several passages and:

h) obtaining adherent avian EBx® cell lines derived from ES cells capable of proliferating in a basal medium in the absence of growth factors, feeder layer and mammalian serum, and wherein said continuous diploid avian cell lines do not produce replication-competent endogenous retrovirus particles;

i) optionally, further adapting adherent avian EBx® cell lines to suspension culture conditions, preferably by promoting the growth as suspension, more preferably by transferring the adherent avian EBx® cell lines obtained in step h) in another support having lower attachment characteristic than the initial support (i.e. such as Ultra Low attachment support).

Step j) of adapting adherent avian EBx® cell lines to suspension culture conditions, when carried out, can be effected in another preferred embodiment before the step g) of progressively decreasing the concentration of mammalian serum in the culture medium.

In another preferred embodiment, the basal culture medium in step b) of the process for obtaining continuous diploid avian cell lines according to the present invention, is further supplemented with a growth factor selected in the group comprising interleukin 6 (IL-6), interleukin 6 receptor (IL-6R), Stem cell Factor (SCF) and Fibroblast Growth Factor (FGF), and the said process further comprises a step d) of:

d) optionally withdrawing all the growth factors selected from the group comprising IL-6, IL-6R, SCF, FGF from the culture medium and further culturing the ES cells for at least one passage.

In a more preferred embodiment, when step d) is carried out, the step e) of withdrawing IGF-1 and CNTF from the culture medium, is effected after the step d) of withdrawing all the growth factors selected from the group comprising IL-6, IL-6R, SCF, FGF from the culture medium.

According to the invention, "basal culture medium" meant a culture medium with a classical media formulation that allows, by itself, at least cells survival, and even better, cell growth. Examples of basal media are BME (basal Eagle Medium), MEM (minimum Eagle Medium), medium 199, DMEM (Dulbecco's modified Eagle Medium), GMEM (Glasgow modified Eagle medium), DMEM-HamF12, Ham-F12 and Ham-F10, Iscove's Modified Dulbecco's medium, MacCoy's 5A medium, RPMI 1640, GTM3. Basal medium comprises inorganic salts (for examples: $CaCl_2$, KCl, NaCl, $NaHCO_3$, $NaH_2PO_4$, $MgSO_4$, ... ), amino-acids, vitamins (thiamine, riboflavin, folic acid, D-Ca panthothenate, ... ) and others components such as glucose, beta-mercapto-ethanol, sodium pyruvate. Preferably basal medium is a synthetic medium. Table 1 gives the composition of DMEM/HAM F12:

TABLE 1

| DMEM-HAM F12 Formulation (mg/l) | |
|---|---|
| Inorganic Salts | |
| Calcium Chloride anhydrous | 116.60 |
| Ferric(III)-Nitrate•$9H_2O$ | 0.05 |
| Ferric(II)-Sulphate•$7H_2O$ | 0.417 |
| Potassium Chloride | 311.80 |
| Cupric(II)-Sulphate•$5H_2O$ | 0.0013 |
| Magnesium Chloride•$6H_2O$ | 61.20 |
| Magnesium Sulphate anhydrous | 48.84 |
| Sodium Chloride | 6996.00 |
| Sodium Dihydrogen Phosphate•$H_2O$ | 62.50 |
| Di-Sodium Dihydrogen Phosphate anhydrous | 71.02 |
| Zinc Sulphate•$7H_2O$ | 0.432 |
| Sodium Hydrogen Carbonate | 1200.00 |
| Amino Acids | |
| L-Alanine | 4.45 |
| L-Arginine•HCl | 147.50 |
| L-Asparagine•$H_2O$ | 7.50 |
| L-Aspartic Acid | 6.65 |
| L-Cystine•HCl•$H_2O$ | 31.29 |
| L-Cysteine•2HCl | 17.56 |
| L-Glutamic Acid | 7.35 |
| L-Glutamine in E15-813 | 365.00 |
| Glycine | 18.75 |
| L-Histidine•HCl•$H_2O$ | 31.48 |
| L-Isoleucine | 54.47 |
| L-Leucine | 59.05 |
| L-Lysine•HCl | 91.25 |
| L-Methionine | 17.24 |
| L-Phenylalanine | 35.48 |
| L-Proline | 17.25 |
| L-Serine | 26.25 |
| L-Threonine | 53.45 |
| L-Tryptophan | 9.02 |
| L-Tyrosine | 38.70 |
| L-Valine | 52.85 |
| Vitamins | |
| D(+)-Biotin | 0.0035 |
| D-Calcium Pantothenate | 2.24 |
| Choline Chloride | 8.98 |

TABLE 1-continued

| DMEM-HAM F12 Formulation (mg/l) | |
|---|---|
| Folic Acid | 2.65 |
| Myo-Inositol | 12.60 |
| Nicotinamide | 2.02 |
| Pyridoxal•HCl | 2.00 |
| Pyridoxine•HCl | 0.031 |
| Riboflavin | 0.219 |
| Thiamine•HCl | 2.17 |
| Thymidine | 0.365 |
| Vitamin B12 | 0.68 |
| Other Components | |
| D-Glucose anhydrous | 3151.00 |
| Hypoxanthine | 2.10 |
| DL-68-Lipoic Acid | 0.105 |
| Linoleic Acid | 0.042 |
| Phenol Red | 8.10 |
| Putrescine•2HCl | 0.081 |
| Sodium Pyruvate | 55.00 |

In addition, basal medium of the invention may be complemented with additives selected in the following group:
- 0.1 to 5 mM L-glutamine, preferably between 2 to 3 mM L-Glutamine;
- 0.05 to 2 mM sodium pyruvate, preferably between 0.1 mM to 1 mM sodium pyruvate;
- 0.1 to 2.5% non-essential amino-acids, preferably around 1% non-essential amino-acids;
- 0.1 to 2.5% vitamins, preferably around 1% vitamins
- 0.05 to 5 mM beta-mercapto-ethanol, preferably around 0.16 mM beta-mercapto-ethanol;
- protein hydrolyzate of non-animal origin.

For the establishment of duck EBx® cells of the invention, the basal medium is preferably complemented with protein hydrolyzate of non-animal origin. Protein hydrolyzates of non-animal origin are selected from the group consisting bacteria tryptone, yeast tryptone, plant hydrolyzates, such as soy hydrolyzates, or a mixture thereof. In a preferred embodiment, the protein hydrolyzates of non-animal origin is yeast hydrolyzate. The term "hydrolyzate" includes an enzymatic digest of soy peptone or yeast extract. The hydrolysate can be obtained from a plurality of soy peptone or yeast extract preparations, respectively, which can be further enzymatically digested (for example, by papain), and/or formed by autolysis, thermolysis and/or plasmolysis. Hydrolysates also may be obtained commercially, such as Yeastolate, Hy-Soy, Hy-Yeast 412 and Hi-Yeast 444, from sources such as SAFC BioSciences (formerly JRH) (Lenaxa, Kans.), Quest International (Norwich, N.Y.), OrganoTechnie S.A. (France) or Deutsche Hefewerke GmbH (Germany). Sources of yeast extracts also are disclosed in WO 98/15614. Sources of yeast extracts and soy hydrolysates also are disclosed in WO00/03000. The hydrolysates used in media of the invention are preferably purified from a crude fraction, because impurities which could interfere with efficient cultivation are preferably eliminated during this purification, thereby improving the consistency of the hydrolysate. Purification can be by ultrafiltration or Sephadex chromatography (for example, with Sephadex G25 or Sephadex G10 or equivalent materials), ion-exchange chromatography, affinity chromatography, size exclusion chromatography or "reversed-phase" chromatography. Preferably, purification is performed by ultrafiltration utilizing a 10 kDa cut-off filter. These processes are known in the field. Using these methods, fractions can be selected which contain soy or yeast hydrolysate of defined molecular weight. Preferably, the average molecular weights of the soy and yeast hydrolysates are preferably between about 220 and 375 daltons. Preferably, yeast hydrolyzate is present in the cell culture medium. Yeast hydrolyzate 50× (around 200 g/l) obtained for example from SAFC-BIOSCIENCES (Ref 58902C) is present in the cell culture medium at a final concentration comprises between around 0.1× to 2×, preferably around 0.5× to around 1× into the culture medium. Soy hydrolyzate may also be added to the cell culture medium. Soy hydrolyzate 50× obtained for example from SAFC-BIOSCIENCES (Ref 58903C) is added at a final concentration comprises between around 0.1× to 2×, preferably around 1× into the culture medium. Alternatively a mixture of soy hydrolyzate and yeast hydrolyzate may be added to the cell culture medium as described in US2004/0077086.

According to a preferred basal medium of the invention is DMEM-HamF12 that are complemented with 2 mM L-glutamin, 1 mM sodium pyruvate, 1% non-essential amino-acids, vitamins 1%, 0.16 mM beta-mercapto-ethanol, and optionally with 1× yeast hydrolyzate.

By "complete culture medium", it is meant a basal culture medium complemented or not, preferably a basal synthetic medium, supplemented with at least one growth factor and animal serum. Example of complete culture medium is described in WO 03/076601, WO 05/007840, EP 787180, U.S. Pat. No. 6,114,168, U.S. Pat. No. 5,340,740, U.S. Pat. No. 6,656,479, U.S. Pat. No. 5,830,510 and in Pain et al. (1996, Development 122:2339-2348). Alternatively, the complete culture medium may a conditioned medium, preferably BRL conditioned medium. By way of example, BRL conditioned media is prepared according to art-recognized techniques, such as described by Smith and Hooper (1987, Dev. Biol. 121:1-9). BRL cells are available from ATCC accession number CRL-1442. Conditioned medium may be supplemented with exogenous growth factors and animal serum as described below.

The term "growth factors" as used herein meant growth factor necessary for the survival and the growth of the undifferentiated avian ES cells in culture in a basal culture medium. It is possible to schematically distinguish two families of growth factors: the cytokines and the trophic factors. The cytokines are mainly cytokines whose action is through a receptor which is associated with the gp130 protein. Thus, leukemia inhibitory factor (LIF), interleukin 11, interleukin 6, interleukin 6 receptor, Ciliary Neurotrophic factor (CNTF), oncostatin and cardiotrophin have a similar mode of action with the recruitment at the level of the receptor of a specific chain and the combination of the latter with the gp130 protein in monomeric or sometimes hetero-dimeric form. The trophic factors are mainly Stem cell Factor (SCF), Insulin Growth factor 1 (IGF-1) and Fibroblast Growth Factor (FGF), preferably basic FGF (bFGF) or human FGF (hFGF).

The complete culture medium according to the invention comprises basal culture medium, preferably basal synthetic medium, and at least one cytokine whose action is through a receptor which is associated with the gp130 protein and/or at least one trophic factors. Preferably, the complete culture medium according to the invention comprises basal medium and at least one growth factor selected in the group consisting of Leukemia Inhibitory factor (LIF), oncostatin, cardiotrophin, Insulin Growth factor 1 (IGF-1), Ciliary Neurotrophic factor (CNTF), Interleukin 6 (IL-6), interleukin 6 receptor (IL-6R), Stem cell Factor (SCF), Fibroblast Growth Factor (FGF), interleukin 11 (IL-11). According to a first preferred embodiment, the complete culture medium is basal medium supplemented with animal serum and with at least IGF-1 and CNTF. According to a second preferred embodiment, the complete culture medium is basal medium supplemented with animal serum and at least IGF-1, CNTF, IL-6 and IL-6R.

According to a third preferred embodiment, the complete culture medium is basal medium supplemented with animal serum and at least IGF-1, CNTF, IL-6, IL-6R, SCF, FGF. According to another embodiment, the complete culture medium is a conditioned culture medium comprising growth factors (i.e expressed by BRL or STO cells for example) and optionally supplemented with at least one exogenous growth factors selected in the group comprising: LIF, IGF-1, CNTF, IL-6, IL-6R, SCF, FGF, IL-11. The concentration of growth factors IGF-1, CNTF, IL-6, IL-6R, SCF, FGF, IL-11 in the basal medium or in the conditioned culture medium is comprised between about 0.01 to 10 ng/ml, preferably, 0.1 to 5 ng/ml, and more preferably about 1 ng/ml.

The culture medium of the invention may also comprise in addition antibiotics, such as for example, gentamicine, penicilline and streptomycine, to prevent bacterial contamination. Antibiotics may be added to the culture medium at the early passages of ES cells culture. For example, gentamycin at a final concentration of 10 ng/ml, penicillin at a final concentration of 100 U/ml and streptomycin at a final concentration of 100 μg/ml may be added to the culture medium. In a preferred embodiment, no antibiotics is added to the culture medium during the late steps of process of establishment of continuous diploid avian cell lines of the invention.

During the process of establishment of avian embryonic stem cells of the invention, the cells are cultured on a layer of feeder cells. More preferably, feeder cells are animal cells or cell lines cultured for the purpose of culturing avian ES cells. Alternatively, the feeder cells can be substituted with extracellular matrix plus bound growth factors. Feeder matrix will thereafter refers to either feeder cells or extra-cellular matrix. A feeder matrix as used herein is constructed in accordance with procedures known in the art. As noted above, it is preferred that the feeder matrix be preconditioned. By the term "preconditioned" it is meant that the feeder matrix is cultured in the presence of media for a period of time prior to the depositing of cells originating from the blastoderm disk fertilized avian eggs in contact with the feeder matrix, e.g. a time sufficient to initiate and establish production of, for example, growth factors or other factors by the feeder matrix; usually a feeder matrix is preconditioned by culturing the feeder matrix by itself for one to two days prior to the depositing of cells originating from the blastoderm disk fertilized avian eggs in contact with the feeder matrix. The feeder cells preferably comprises mouse fibroblast cells. STO fibroblasts are preferred, but primary fibroblasts are also suitable. Also while the present invention has been described with respect to the use of mouse cell feeder matrices, it is contemplated that feeder matrices comprising cells from other murine species (e.g. rat); other mammalian species (e.g; ungulate, bovine, porcine species); or avian species (e.g. Gallinacea, chicken, turkey, duck, goose, quail, pheasant) may also be used. In another embodiment, feeder cells of the invention may be transfected with expression vector(s) allowing for example the constitutive expression of growth factors such as avian SCF in STO cells. Thus, this "feeder" produces the factor in a form which is soluble and/or attached in the plasma membrane of the cells. Thus, the culturing process of the present invention may optionally comprise establishing a monolayer of feeder cells. Feeder cells are mitotically inactivated using standard techniques. For example, the feeder cells may be exposed to X or gamma radiation (e.g. 4000 Rads of gamma radiation) or may be treated with Mitomycin C (e.g. 10 μg/ml for 2-3 hours). Procedures for mitotically inactivating cells are also detailed in the information typically sent with cells from the American Type Culture Collection (ATCC), 10801 University Boulevard, Manassas, Va. 20110-2209 (e.g. STO feeder cells are available under ATCC accession number 1503). Mono-layers may optionally be cultured to about 80% confluency, preferably to about 90% confluency, and more preferably about 100% confluency. While configuration of the feeder cells as a monolayer is the preferred configuration for the culture, any suitable configuration is contemplated to be within the scope of the present invention. Thus, for example, layers, mono-layers, clusters, aggregates or other associations or groupings of feeder cells are contemplated to fall within the scope of the present invention and are particularly contemplated to fall with the meaning of the term "matrix".

The culture medium of the invention is supplemented with animal serum. The animal serum preferably used is fetal animal serum. Fetal bovine serum is preferred. Also while the present invention has been described with respect to the use of fetal bovine serum, it is contemplated that animal serum comprising serum from other animal species (e.g. chicken, horse, porcine, ungulate, etc.) may also be used. The final concentration of animal serum in the culture medium is comprises between approximately 1 to 25%, preferably between 5% to 20%, more preferably between 8% and 12%. In the preferred embodiment, the final concentration of animal serum in the culture medium is approximately 10%. According to a preferred embodiment, the culture medium comprises approximately 10% of fetal calf serum.

In a first preferred embodiment, the bird of the present invention is selected in the Order of Anseriformes, and is preferably a duck, more preferably a Pekin Duck, and more preferably Pekin duck strain M14 or GL30. According to a second preferred embodiment, the bird of the present invention is a Muscovy duck. Therefore, the instant invention provides a first process for obtaining continuous diploid duck cell lines derived from embryonic stem cells (ES), wherein said duck cell lines do not produce replication-competent endogenous retrovirus particles, and said process is comprising the steps of:

a) isolating duck embryo(s) at oviposition (i.e egg laying), or slightly prior or after oviposition. Optionally, the egg may be incubated, usually overnight, to mature (i.e Muscovy duck);

b) suspending duck embryonic stem (ES) cells obtained by dissociating embryo(s) of step a) in a basal culture medium supplemented with Insulin Growth factor 1 (IGF-1), Ciliary Neurotrophic factor (CNTF), interleukin 6 (IL-6), interleukin 6 receptor (IL-6R), Stem cell Factor (SCF) and Fibroblast Growth Factor (FGF) and animal serum;

c) seeding the suspension of ES cells obtained in step b) on a layer of feeder cells and further culturing the duck ES cells for at least 1 passage;

d) withdrawing all the growth factors selected from the group comprising IGF-1, CNTF, IL-6, IL-6R, SCF, FGF from the culture medium over a range of 1 to around 15 passages, preferably simultaneously over one passage, and further culturing the duck ES cells for at least one passage;

f) progressively decreasing the concentration of feeder cells in the culture medium, from a passage to another, so as to obtain a total withdrawal of feeder layer after several passages, preferably, after around 5 to around 25 passages, and further culturing the cells;

g) optionally, progressively decreasing the concentration of animal serum in the culture medium so as to obtain a total withdrawal of animal serum after several passages; and:

h) obtaining adherent duck cell lines derived from ES cells, named duck EBx®, capable of proliferating in a basal medium in the absence of growth factors, feeder layer optionally without animal serum, and wherein said continuous diploid duck cell lines do not produce replication-competent endogenous retrovirus particles;
i) optionally, further adapting adherent duck cell lines to suspension culture conditions. Additives to basal medium are withdrawn during the process, and preferably between steps f) and g) or between steps g) and h).

The animal serum concentration at step b) is preferably of 5 to 10%. The concentration of with Insulin Growth factor 1 (IGF-1), Ciliary Neurotrophic factor (CNTF), interleukin 6 (IL-6), interleukin 6 receptor (IL-6R), Stem cell Factor (SCF) and Fibroblast Growth Factor (FGF) are preferably of about 1 ng/ml.

The instant invention also provides a second process for obtaining continuous diploid duck cell lines derived from embryonic stem cells (ES), wherein said duck cell lines do not produce replication-competent endogenous retrovirus particles, and said process is comprising the steps of:
a) isolating duck embryo(s) at oviposition (i.e egg laying), or slightly prior or after oviposition. Optionally, the egg may be incubated, usually overnight, to mature (i.e Muscovy duck);
b) suspending duck embryonic stem (ES) cells obtained by dissociating embryo(s) of step a) in a basal culture medium supplemented with IGF-1, CNTF, IL-6, IL-6R, SCF and FGF and animal serum;
c) seeding the suspension of ES cells obtained in step b) on a layer of feeder cells and further culturing the duck ES cells for at least 1 passage;
d) withdrawing all the growth factors selected from the group comprising IL-6, IL-6R, SCF, FGF from the culture medium over a range of 1 to around 15 passages, preferably simultaneously over one passage, and further culturing the duck ES cells for at least one passage;
e) withdrawing the growth factors IGF-1 and CNTF from the culture medium over a range of 1 to around 15 passages, preferably simultaneously over one passage, and further culturing the duck ES cells for at least one passage;
f) progressively decreasing the concentration of feeder cells in the culture medium so as to obtain a total withdrawal of feeder layer after several passages, preferably, after around 5 to around 25 passages, and further culturing the cells;
g) optionally, progressively decreasing the concentration of animal serum in the culture medium so as to obtain a total withdrawal of animal serum after several passages; and
h) obtaining adherent duck cell lines derived from ES cells, named duck EBx®, capable of proliferating in a basal medium in the absence of growth factors, feeder layer optionally without animal serum, and wherein said continuous diploid duck cell lines do not produce replication-competent endogenous retrovirus particles;
i) optionally, further adapting adherent duck cell lines to suspension culture conditions. Additives to basal medium are withdrawn during the process, and preferably between steps f) and g) or between steps g) and h).

The animal serum concentration at step b) is preferably of 5 to 10%. The concentration of IGF-1, CNTF, IL-6, IL-6R, SCF and FGF are preferably of about 1 ng/ml.

The instant invention also provides a third process for obtaining continuous diploid duck cell lines derived from embryonic stem cells (ES), wherein said duck cell lines do not produce replication-competent endogenous retrovirus particles, and said process is comprising the steps of:
a) isolating duck embryo(s) at oviposition (i.e egg laying), or slightly prior or after oviposition. Optionally, the egg may be incubated, usually overnight, to mature (i.e Muscovy duck);
b) suspending duck embryonic stem (ES) cells obtained by dissociating embryo(s) of step a) in a basal culture medium supplemented with Insulin Growth factor 1 (IGF-1), and Ciliary Neurotrophic factor (CNTF) and animal serum;
c) seeding the suspension of ES cells obtained in step b) on a layer of feeder cells and further culturing the duck ES cells for at least 1 passage;
d) withdrawing the growth factors IGF-1 and CNTF from the culture medium over a range of 1 to around 15 passages, preferably simultaneously over one passage, and further culturing the duck ES cells for at least one passage;
f) progressively decreasing the concentration of feeder cells in the culture medium so as to obtain a total withdrawal of feeder layer after several passages, preferably, after around 5 to around 25 passages, and further culturing the cells; Removal of additives?
g) optionally, progressively decreasing the concentration of animal serum in the culture medium so as to obtain a total withdrawal of animal serum after several passages; and,
h) obtaining adherent duck cell lines derived from ES cells, named duck EBx®, capable of proliferating in a basal medium in the absence of growth factors, feeder layer optionally without animal serum, and wherein said continuous diploid avian cell lines do not produce replication-competent endogenous retrovirus particles;
i) optionally, further adapting adherent duck EBx® cell lines to suspension culture conditions.

Additives to basal medium are withdrawn during the process, and preferably between steps f) and g) or between steps g) and h).

The animal serum concentration at step b) is preferably of 5 to 10%. The concentration of with IGF-1 and CNTF are preferably of about 1 ng/ml.

Once adherent or suspension duck cell lines have been obtained, the process of the invention may also comprises the additional step of adapting, duck EBx® cells to the growth in cell culture medium without protein hydrolyzate of non-animal origin, such as yeast hydrolyzates.

Preferably, duck EBx® cell lines of the invention do not display reverse transcriptase activity by Q-PERT analysis. Moreover, no replication-competent endogenous retrovirus particles is produced by duck EBx® cells as demonstrated by co-culture experiments of duck EBx® cells of the invention with ALV replication competent cells, such as quail QT6 cells or chicken DF1 cells. In addition, transmission electronic microscopy (TEM) analysis also demonstrate the absence of replication-competent endogenous retrovirus particles in duck EBx® cells. Preferably, the duck EBx® cell line of the invention is selected among duck EB24, duck EB26 and duck EB66 as described hereinafter.

In another preferred embodiment, the bird of the present invention is selected in the Order of Galliformes and more preferably is a chicken, preferably an ev-0 domestic chicken (*Gallus Gallus* subspecies *domesticus*). Therefore, the instant invention provides a process for obtaining continuous diploid ev-0 domestic chicken cell lines derived from embryonic stem cells (ES), wherein said ev-0 domestic chicken cell lines do not produce replication-competent endogenous ALV-E retrovirus particles, and said process is comprising the steps of:
  a) isolating ev-0 domestic chicken embryo(s) at oviposition (i.e egg laying) or slightly prior or after oviposition;
  b) suspending ev-0 domestic chicken embryonic stem (ES) cells obtained by dissociating embryo(s) of step a) in a basal culture medium supplemented with IGF-1, CNTF, IL-6, IL-6R, SCF and FGF and animal serum;
  c) seeding the suspension of ES cells obtained in step b) on a layer of feeder cells and further culturing the ev-0 domestic chicken ES cells for at least 1 passage;
  d) withdrawing all the growth factors selected from the group comprising IGF-1, CNTF, IL-6, IL-6R, SCF, FGF from the culture medium over a range of 1 to around 15 passages, preferably simultaneously over one passage, and further culturing the chicken ES cells for at least one passage;
  f) progressively decreasing the concentration of feeder cells in the culture medium so as to obtain a total withdrawal of feeder layer after several passages, preferably, after around 5 to around 25 passages, and further culturing the cells;
  g) optionally, progressively decreasing the concentration of animal serum in the culture medium so as to obtain a total withdrawal of animal serum after several passages and:
  h) obtaining adherent ev-0 domestic chicken cell lines derived from ES cells, named EBx ev-0, capable of proliferating in a basal medium in the absence of growth factors, feeder layer optionally without animal serum, and wherein said continuous diploid avian cell lines do not produce replication-competent endogenous ALV-E retrovirus particles;
  i) optionally, further adapting adherent avian cell lines EBx ev-0 to suspension culture conditions.

Additives to basal medium are withdrawn during the process, and preferably between steps f) and g) or between steps g) and h).

The animal serum concentration at step b) is preferably of 5 to 10%. The concentration of IGF-1, CNTF, IL-6, IL-6R, SCF and FGF are preferably of about 1 ng/ml.

The instant invention also provides a second process for obtaining continuous diploid ev-0 domestic chicken cell lines derived from embryonic stem cells (ES), wherein said ev-0 domestic chicken cell lines do not produce replication-competent endogenous ALV-E retrovirus particles, and said process is comprising the steps of:
  a) isolating ev-0 domestic chicken embryo(s) at oviposition (i.e egg laying) or slightly prior or after oviposition;
  b) suspending ev-0 domestic chicken embryonic stem (ES) cells obtained by dissociating embryo(s) of step a) in a basal culture medium supplemented with IGF-1, CNTF, IL-6, IL-6R, SCF and FGF and animal serum;
  c) seeding the suspension of ES cells obtained in step b) on a layer of feeder cells and further culturing the ev-0 domestic chicken ES cells for at least 1 passage;
  d) withdrawing all the growth factors selected from the group comprising IL-6, IL-6R, SCF, FGF from the culture medium over a range of 1 to around 15 passages, preferably simultaneously over one passage, and further culturing the chicken ES cells for at least one passage;
  e) withdrawing the growth factors IGF-1 and CNTF from the culture medium over a range of 1 to around 15 passages, preferably simultaneously over one passage, and further culturing the ev-0 domestic chicken ES cells for at least one passage;
  f) progressively decreasing the concentration of feeder cells in the culture medium so as to obtain a total withdrawal of feeder layer after several passages, preferably, after around 5 to around 45 passages, and further culturing the cells;
  g) optionally, progressively decreasing the concentration of animal serum in the culture medium so as to obtain a total withdrawal of animal serum after several passages and:
  h) obtaining adherent ev-O domestic chicken cell lines derived from ES cells capable of proliferating in a basal medium in the absence of growth factors, feeder layer optionally without animal serum, and wherein said continuous diploid ev-O domestic chicken cell lines, named chicken EBx®, do not produce replication-competent endogenous retrovirus particles;
  i) optionally, further adapting adherent ev-O domestic chicken cell lines to suspension culture conditions.

Additives to basal medium are withdrawn during the process, and preferably between steps f) and g) or between steps g) and h).

The animal serum concentration at step b) is preferably of 5 to 10%. The concentration of with IGF-1, CNTF, IL-6, IL-6R, SCF and FGF are preferably of about 1 ng/ml.

The instant invention also provides a third process for obtaining continuous diploid ev-0 domestic chicken cell lines derived from embryonic stem cells (ES), wherein said ev-0 domestic chicken cell lines do not produce replication-competent endogenous ALV-E retrovirus particles, and said process is comprising the steps of:
  a) isolating ev-0 domestic chicken embryo(s) at oviposition (i.e egg laying) or slightly prior or after oviposition;
  b) suspending ev-0 domestic chicken embryonic stem (ES) cells obtained by dissociating embryo(s) of step a) in a basal culture medium supplemented with IGF-1 and CNTF and animal serum;
  c) seeding the suspension of ES cells obtained in step b) on a layer of feeder cells and further culturing the ev-0 domestic chicken ES cells for at least 1 passage;
  d) withdrawing the growth factors IGF-1 and CNTF from the culture medium over a range of 1 to around 15 passages, preferably simultaneously over one passage, and further culturing the ev-0 domestic chicken ES cells for at least one passage;
  f) progressively decreasing the concentration of feeder cells in the culture medium so as to obtain a total withdrawal of feeder layer after several passages, preferably, after around 5 to around 45 passages, and further culturing the cells;
  g) optionally, progressively decreasing the concentration of animal serum in the culture medium so as to obtain a total withdrawal of animal serum after several passages; and,
  h) obtaining adherent ev-0 domestic chicken cell lines derived from ES cells, named chicken EBx® ev-0, capable of proliferating in a basal medium in the absence of growth factors, feeder layer optionally without animal serum, and wherein said continuous diploid chicken cell lines do not produce replication-competent endogenous retrovirus particles;
  i) optionally, further adapting adherent ev-0 domestic chicken cell lines to suspension culture conditions.

Additives to basal medium are withdrawn during the process, and preferably between steps f) and g) or between steps g) and h).

The animal serum concentration at step b) is preferably of 5 to 10%. The concentration of with IGF-1 and CNTF are preferably of about 1 ng/ml.

In another preferred embodiment, the bird of the present invention is a domestic chicken (*Gallus Gallus* subspecies *domesticus*) obtained from a specific-pathogen-free (SPF) flock. More preferably, the chicken strain is White-Leghorn. SPF chicken eggs has been screened for the absence of known chicken bacterial pathogens and viruses, including the reticuloendotheliosis virus (REV) and the avian exogenous leucosis virus (ALV-A, ALV-B, ALV-C, ALV-D, ALV-J). The SPF egg of the invention may VALO eggs from LOHMANN (Cuxhaven, Germany) or L22 eggs from CHARLES RIVER (Spafas). Therefore, the instant invention also provides processes for obtaining continuous diploid chicken cell lines derived from embryonic stem cells (ES) obtained from SPF chicken eggs, like described with ev-0 chicken eggs. Preferably, the chicken EBx® cell line obtained from SPF eggs is EBv13.

Chicken EBx® cell lines of the invention may display reverse transcriptase activity by Q-PERT analysis, but without producing replication-competent endogenous retrovirus particles. The absence of replication-competent endogenous retrovirus particles may be demonstrated by co-culture experiments of chicken EBx® ev-0 cells of the invention with ALV replication competent cells, such as quail QT6 cells or chicken DF1 cells. In addition, the absence of endogenous retrovirus particles in chicken EBx® ev-0 cells may be also demonstrate by TEM.

Body temperature of bird is usually around 39° C. Therefore, the processes of the invention may also comprise the additional step of decreasing the cell culture temperature to 37° C. in order to adapt the avian cell lines of the invention to grow at 37° C. Preferably, the temperature adaptation is performed after feeder depletion and prior serum depletion. Alternatively, the temperature adaptation is performed after the serum depletion step or after the step of adapting the cell lines to suspension culture.

The established lines EBx® of the invention have the characteristic to grow either as adherent cells or as suspension cells in a culture medium free of exogenous growth factors and animal serum and without feeder cells. Different techniques can be used alone or in combination to adapt cells to suspension culture, among them:

Adherent cells are seeded at high cell density, slightly above cell confluence to force the cells to go into suspension;

Adherent cells are seeded in a cell culture medium with a low animal serum concentration;

Adherent cells are seeded onto cell culture vessels made of plastic that do not allow cell adhesion or a weak cell adhesion, such as bacterial dishes and plates and ultra-low attachment plates developed by companies like Corning (tissue culture dishes & plates Ref. 3262, 3473, 3471, 3474; Flasks Ref. 3814 . . . ) or Sarstedt (Flask ref 831810502 . . . );

Adherent cells are seeded on vessel and cultured under agitation (Approx. 50 rpm).

The EBx® cells, preferably duck EBx® and chicken EBx® ev-0, can be in vitro cultured over a considerable period of time. Advantageously, the adherent or anchorage-independent (i.e "suspension) EBx® cells obtained by the process of the invention are capable to proliferate for at least 50 generation, at least 75 generation, at least 100 generation, at least 125 generation, at least 150 generation, at least 175 generation, at least 200 generation, at least 250 generation.

The expression "line" is understood to mean any population of cells capable of proliferating indefinitely in culture in vitro while retaining to a greater or lesser degree the same morphological and phenotypic characteristics. Clones may be obtained, for example by limit dilution, from EBx® cells of the invention. These clones are cells which are genetically identical to the cell from which they are derived by division.

The present invention also relates to the continuous diploid avian cell lines, named EBx®, obtainable by the process of the invention, said EBx® being small, round (i;e diameter around 10 um), individualized cells with a doubling time of around 30 hours or less at 37° C. or 39° C. The avian EBx® cells, preferably the duck EBx® or chicken EBx® ev-0, express an embryonic stem cell phenotype with the following characteristics:

a high nucleo-cytoplasmic ratio, an endogenous telomerase activity, optionally, they may express one or more additional ES markers such as alkaline phosphatase, SSEA-1, EMA-1, ENS1 markers.

A doubling time shorter than the doubling time of the avian ES cells of step a) of the process of the invention (48 h to 72 h at 39° C.), of about 30 hours or less (preferably 24 hours) at 37° C.

Said cells do not produce replication competent endogenous retrovirus particles.

The avian EBx® cell lines of the invention are capable of proliferating indefinitely in a basal medium, in particular in a medium such as SAFC Excell media, DMEM, GMEM, DMEM-HamF12 or McCoy, free of exogenous growth factors, serum and/or inactivated feeder layer, optionally complemented with various additives commonly used by persons skilled in the art. Examples of additives are non-essential amino acids, vitamins, sodium pyruvate and antibiotics. Duck EBx® cells of the invention have the remarkable feature to grow in a basal culture medium that is not complemented with glutamine.

The present invention also relates to a cell culture medium to maintain pluri- or multipotent avian embryonic stem cells, preferably pluri- or multipotent duck embryonic stem (ES) cells, into culture in an undifferentiated state. According to a preferred embodiment, the present invention relates to cell culture medium for duck embryonic stem cells comprising a basal culture medium, supplemented with animal serum and supplemented with at least IGF-1 and CNTF. According to a second preferred embodiment, the present invention relates to cell culture medium for duck embryonic stem cells comprising a basal culture medium supplemented with animal serum and supplemented with at least IGF-1, CNTF, Il-6, Il-6R. According to a third preferred embodiment, the present invention relates to a cell culture medium for duck embryonic stem cells comprising a basal culture medium supplemented with animal serum and supplemented with at least IGF-1, CNTF, Il-6, Il-6R, SCF and FGF. Said media are sufficient for the maintenance of said duck ES cells into culture for at least 7 days, preferably for at least 20 days, preferably for at least 100 days in an undifferentiated state. Said culture media of the invention may further comprise optionally at least one compound selected in the group comprising Interleukin-11, cardiotrophin, oncostatin and leukaemia inhibitory factor (LIF). Preferably, said culture media further comprise protein hydrolyzate of non-animal origin as previously described; more preferably it is yeast hydrolyzate at 1× concentration. The culture medium of avian (preferably duck) ES cells of the invention may further comprise a layer of feeder cells.

The instant invention also provide a sustained duck ES cell culture consisting essentially of undifferentiated duck ES cells expressing stem cell phenotype with the following characteristics:
   a high nucleo-cytoplasmic ratio,
   an endogenous telomerase activity,
   optionally, duck ES cells may express one or more additional ES markers such as alkaline phosphatase, SSEA-1, EMA-1, ENS1 markers.
   A doubling time of about around than 40 hours at 37° C. or 39° C.
Said undifferentiated duck cells according to the invention are capable of maintaining said stem cell phenotype when grown on feeder cells in a cell culture medium for duck embryonic stem cells as previously described. Said undifferentiated duck cells are useful to produce chimeric or transgenic ducks.

Therefore, the present invention also relates to a method of obtaining chimeric duck, said method comprising the steps of:
   a) introducing a sustained duck ES cell culture as described above into the sub-germinal cavity of a recipient duck embryo; and
   b) incubating the embryo obtained in step a) to hatch as a duckling;
   c) selecting said chimeric duckling comprising heterologous cells having colonized said duckling.

The present invention also relates to a method of obtaining genetically modified chimeric duck, comprising the steps of:
   a) introducing a genetically modified duck ES cells as described above into the sub-germinal cavity of a recipient duck embryo; and
   b) incubating the embryo obtained in step a) to hatch as a duckling;
   c) selecting said chimeric duckling comprising genetically modified heterologous cells having colonized said duckling.

The present invention also relates to a method of obtaining a progeny of said chimeric duckling wherein said method comprises the following steps:
   a) allowing the selected chimeric duckling obtained at steps c) to mature as an adult bird;
   b) breeding said adult bird having heterologous cells herein, thereby producing a bird progeny;
   c) selecting the birds of interest in the progeny.

The invention may comprise the additional step of expressing an heterologous polypeptide encoded by an expression vector comprised in said genetically modified duck ES cells. Preferably, the heterologous polypeptide is delivered into biological fluid of duck, such as blood, sperm, urine, or the white of a developing avian egg produced by a female of the genetically modified duck.

The EBx® cells of the invention have all the above mentioned characteristics and are useful for the production of biologics such as viral vaccines and recombinant peptides and proteins.

The instant invention also provide a process of replicating a virus in the continuous diploid avian EBx® cell lines of the invention. More preferably, the invention provides a process of replicating a virus in the continuous diploid avian EBx® cell lines of the invention, preferably duck or chicken EBx® cell lines, that comprise the steps of:
   infecting an avian EBx® cell culture with a virus of interest; said avian EBx® cells being preferably cultured in animal serum free medium;
   culture of infected avian EBx® cells in order to replicate said virus;
   harvest the virus in cell culture supernatant and/or inside said cells.

According to a preferred embodiment, said process comprises the steps of:
   a) proliferating said avian EBx® in a cultivation vessel, in suspension, in a serum-free medium No 1;
   b) infecting said cells with the selected virus when the cell density is of at least 1.5 million cells/ml;
   c) optionally, shortly before infection, simultaneously to infection, or shortly after infection adding to the cell culture serum-free medium No 2; and
   d) further culturing said infected cells in order to allow virus replication; and
   e) optionally, harvesting said virus.

Said process of the invention may comprise the additional step of adding proteolytic enzyme in the culture medium in conditions that allow virus propagation. The proteolytic enzyme is selected from the group consisting of trypsin, chymotrypsine, thermolysine, pepsine, pancreatine, papaïne, pronase, subtilisine A, elastase, furine and carboxypeptidase. According to a preferred embodiment, the enzyme is trypsin. Preferably, the proteolytic enzyme is a recombinant protein produced on a procaryotic host or on plants (i.e: trypzean). The proteolytic enzyme may added before, during and/or after the virus infection. Preferably, the addition of proteolytic enzyme is performed after virus infection. The addition of proteolytic enzyme in the culture medium may be performed one time per day, more than one time per day, or less than one time per day until the virus harvest.

The term "virus" as used herein includes not only naturally occurring viruses but also attenuated viruses, reassortant viruses, vaccine strains, as well as recombinant viruses and viral vectors derived thereof. The virus of the invention are preferably selected from the group comprising poxviruses, orthomyxoviruses, paramyxoviruses, herpes viruses, hepadnaviruses, adenoviruses, parvoviruses, reoviruses, circoviruses, coronaviruses, flaviviruses, togaviruses, birnaviruses and retroviruses.

In a preferred embodiment, the viruses, the related viral vectors, viral particles and viral vaccines belong to the family of poxyiridae, and more preferably to the chordopoxyiridae. In one embodiment, the virus or the related viral vectors, viral particles and viral vaccines are a poxvirus, preferably an avipoxvirus selected among fowlpox virus (i.e TROVAC), canarypox virus (i.e ALVAC), juncopox virus, mynahpox virus, pigeonpox virus, psittacinepox virus, quailpoxvirus, sparrowpoxvirus, starling poxvirus, turkeypox virus. According to another preferred embodiment, the virus is a vaccinia virus selected among Lister-Elstree vaccinia virus strain, modified vaccinia virus such as Modified Vaccinia virus Ankara (MVA) which can be obtained from ATCC (ATCC Number VR-1508), NYVAC (Tartaglia et al., 1992, Virology, 188:217-232), LC16 m8 (Sugimoto et Yamanouchi, 1994, Vaccine, 12:675-681), CVI78 (Kempe et al., 1968, Pediatrics 42:980-985) and other recombinant or non-recombinant vaccinia virus.

In another preferred embodiment, the viruses, the related viral vectors, the viral particles and vaccines belong to the family of ortho-myxoviridae, in particular influenza virus. The influenza virus is selected from the group consisting of human influenza virus, avian influenza virus, equine influenza virus, swine influenza virus, feline influenza virus. Influenza virus is preferably selected in strains A, B and C. Among strains A, one can recite viruses with different subtypes of haemagglutinin and neuraminidase, such as without limitation H1N1, H2N2, H3N2, H4N2, H4N6, H5N1, H5N2, H7N7 et H9N2. Among H1N1 strains, one can recite A/Porto Rico/8/34, A/New Caledonia/20/99, A/Beijing/262/95, A/Johannesburg/282/96, A/Texas/36/91, A/Singapore, A/Solomon Islands/03/2006. Among strains H3N2, one can recite A/Panama/2007/99, A/Moscow/10/99, A/Johannesburg/33/94, A/Wisconsin/10/04. Among B strains, one can recite without limitation B/Porto Rico/8/34, B/Johannesburg/5/99, BNienna/1/99, B/Ann Arbor/1/86, B/Memphis/1/93, B/Harbin/7/94, N/Shandong/7/97, B/Hong Kong/330/01, B/Yamanashi/166/98, B/Jiangsu/10/03, B/Malaysia. The influenza Virus of the invention is selected among wild type virus, primary viral isolate obtained from infected individual, recombinant virus, attenuated virus, temperature sensitive virus, low-temperature adapted virus, reassortant virus, reverse genetic engineered virus. When the virus of the invention is influenza virus, the process of the invention comprises the additional step of adding proteolytic enzyme in the culture medium in conditions that allow virus propagation. According to a preferred embodiment, the enzyme is trypsin. The final concentration of trypsin in cell culture medium is comprises between around 0.01 µg/ml up to 10 µg/ml. More preferably, the final concentration of trypsin in cell culture medium is comprised between 0.01 to 10 usp/ml (usp: US pharmacopea unit) preferably around between 0.05 to 2 usp/ml, more preferably around between 0.3 to 1 usp/ml and more preferably around 0.75 usp/ml.

In another preferred embodiment, the viruses, the related viral vectors, the viral particles and vaccines belong to the family of paramyxoviridae. Preferably the virus is a naturally occurring paramyxovirus or a recombinant paramyxovirus selected in the group comprising measles virus, mumps virus, rubella virus, Sendai virus, Respiratory Syncythial virus (RSV), human para-influenza types I and III, Rinderpest virus, canine distemper virus, Newcastle disease virus, duck para-influenza virus. According to preferred embodiment, the virus is measles virus or a recombinant measles virus. According to another preferred embodiment, the virus is Newcastle Disease virus (NDV) or a recombinant NDV. Example of NDV strain is LaSota strain. When the virus of the invention is NDV, the process of the invention comprises preferably the additional step of adding proteolytic enzyme in the culture medium in conditions that allow virus propagation. According to a preferred embodiment, the enzyme is trypsin. The final concentration of trypsin in cell culture medium is comprises between around 0.01 µg/ml up to 10 µg/ml. More preferably, the final concentration of trypsin in cell culture medium is comprised between 0.01 to 10 usp/ml (usp: US pharmacopea unit) preferably around between 0.3 to 1 usp/ml, more preferably around between 0.4 to 0.75 usp/ml. Interestingly, the EBx® cell lines of the invention that may grow in adherence are useful to perform virus titration, and preferably NDV titration, on a plaque assay. Indeed, unlike CEFs and chicken DF1 fibroblasts for which is was not possible to observe any cytopathic effects, virus growth in EBx® cells leads to the formation of characteristic giant cells. In addition, NDV viral particles may be determined by haemagglutination assay. Therefore, the invention also pertain to the use of EBx® cells of the invention for the titration of virus, such as NDV virus.

In another preferred embodiment, the viruses, the related viral vectors, the viral particles and vaccines belong to the family of togaviridae. Preferably the virus is a naturally occurring alphavirus or a recombinant alphavirus selected in the group comprising Sinbis virus, Semliki forest virus, O'nyong'nyong virus, Chikungunya virus, Mayaro virus, Ross river virus, Eastern equine encephalitis virus, Western Equine encephalitis virus, Venezuelan Equine encephalitis virus.

In another preferred embodiment, the viruses, the related viral vectors, the viral particles and vaccines belong to the family of herpesviridae. Preferably the virus is a naturally occurring Marek Disease virus or a recombinant Marek Disease virus. The Marek Disease virus (MDV) is preferably selected among the license vaccine strains of MDV such as: FC126 (HTV), SB-1, 301B/1, CVI988 Clone C, CVI988/C/R6, CVI988/Rispens, R2/23 (Md11/75).

In another preferred embodiment, the viruses, the related viral vectors, the viral particles and vaccines belong to the family of hepadnaviridae. Preferably the virus is a naturally occurring naturally occurring hepadnavirus or a recombinant hepadnavirus, preferably selected among avian and human hepadnavirus. The avian hepadnavirus is preferably selected among the group consisting of duck hepatitis B virus (DHBV), heron hepatitis B virus (HHBV) and snow goose (SGHBV).

In another preferred embodiment, the viruses, the related viral vectors, the viral particles and vaccines belong to the family of birnaviridae, in particular Infectious Bursal Disease virus.

In another preferred embodiment, the viruses, the related viral vectors, the viral particles and vaccines belong to the family of flaviviridae, in particular Dengue virus, Japanese encephalitis virus and West Nile virus.

In another preferred embodiment, the viruses, the related viral vectors, the viral particles and vaccines belong to the family of coronaviridae, in particular Infectious Bronchitis virus.

In another preferred embodiment, the viruses, the related viral vectors, the viral particles and vaccines belong to the family of circoviridae, in particular Chicken Anemia virus.

In another preferred embodiment, the viruses, the related viral vectors, the viral particles and vaccines belong to the family of retroviridae. Preferably the virus is a naturally occurring retrovirus selected among reticulo-endotheliosis virus, duck infectious anemia virus, suck spleen necrosis virus, or a recombinant retrovirus thereof.

In another preferred embodiment, the viruses, the related viral vectors, the viral particles and vaccines belong to the family of parvoviridae. Preferably the virus is a naturally occurring parvovirus such as duck parvovirus or a recombinant parvovirus thereof.

In another preferred embodiment, the viruses, the related viral vectors, the viral particles and vaccines belong to the family of adenoviridae. Preferably the virus is a naturally occurring adenovirus preferably selected among fowl adenovirus, goose adenovirus, duck adenovirus and pigeon adenovirus or a recombinant adenovirus thereof. Examples of Fowl adenovirus are Fowl adenovirus 1 (CELO), Fowl adenovirus 5 (340), Fowl adenovirus 4 (KR95), Fowl adenovirus 10 (CFA20), Fowl adenovirus 2 (P7-A), Fowl adenovirus 3 (75), Fowl adenovirus 9 (A2-A), Fowl adenovirus 11 (380), Fowl adenovirus 6 (CR119), Fowl adenovirus 7 (YR36), Fowl adenovirus 8a (TR59) Fowl adenovirus 8b (764) and Egg Drop Syndrome virus. Examples of Goose adenovirus are Goose adenovirus 1, Goose adenovirus 2, Goose adenovirus 3. Example of Duck adenovirus is Duck adenovirus 2. Example of Pigeon adenovirus is Pigeon adenovirus 1.

Recombinant viruses include but are not limited to viral vectors comprising a heterologous gene. In some embodiments, a helper function(s) for replication of the viruses is provided by the host cell EBx®, a helper virus, or a helper plasmid. Representative vectors include but are not limited to those that will infect avian or mammalian cells.

The instant invention also relates to the use of EBx® cells of the invention to replicate intracellular bacteria such as *Chlamydia, Rickettsia* or *Coxiella*.

The EBx® cells of the invention may also be used to produce recombinant proteins and peptides. The invention also relates to a method of production of recombinant proteins and peptides, that include the steps of: (i) genetically modifying the EBx® cells of the invention by transient or stable transfection of an expression vector; (ii) optionally, selecting EBx® cells expressing said recombinant proteins or peptides; (iii) and purification of said peptides or proteins. Peptides and proteins produced in EBx® cells are also included in the present invention.

The cultivation vessel of the invention is more preferably selected among continuous stirred tank bioreactor, Wave™ Bioreactor, Bello™ bioreactor, spinner flask, flask and a cell factory. Typically, cells are scaled-up from a master or working cell bank vial through various sizes of T-flasks, roller bottles or Wave™ Bioreactor and, preferably, finally to bioreactors. The resulting cell suspension is then typically fed into a seed production bioreactor (typically 20-30 L volume) for further cultivation, and in some embodiments, to a larger production bioreactor (typically 150-180 L volume and above). The ratio of volume of the second (larger) bioreactor to the seed bioreactor depends upon the degree to which the cell line is propagated in the first bioreactor, but is typically from 3:1 to 10:1, e.g., in the range of (6-8):1. According to a preferred embodiment, the cultivation vessel is a continuous stirred tank bioreactor that allows control of temperature, aeration, pH and other controlled conditions and which is equipped with appropriate inlets for introducing the cells, sterile oxygen, various media for cultivation and outlets for removing cells and media and means for agitating the culture medium in the bioreactor.

According to the present invention, "serum-free medium" (SFM) meant a cell culture medium ready to use, that is to say that it does not required animal serum addition allowing cells survival and cell growth. This medium is not necessary chemically defined, and may contained hydrolyzates of various origin, from plant or yeast for instance. Preferably, said SFM are "non animal origin" qualified, that is to say that it does not contain components of animal or human origin (FAO status: "free of animal origin"). In SFM, the native serum proteins are replaced by recombinant proteins. Alternatively SFM medium according to the invention does not contain protein (PF medium: "protein free medium") and/or are chemically defined (CDM medium: "chemically defined medium"). SFM media present several advantages: (i) the first of all being the regulatory compliance of such media (indeed there is no risk of contamination by adventitious agents such as BSE, viruses); (ii) the optimization of the purification process; (iii) the better reproducibility in the process because of the better defined medium. Examples of commercially available SFM media are: VP SFM (InVitrogen Ref 11681-020, catalogue 2003), Opti Pro (InVitrogen Ref 12309-019, catalogue 2003), Episerf (InVitrogen Ref 10732-022, catalogue 2003), Pro 293 S-CDM (Cambrex ref 12765Q, catalogue 2003), LC17 (Cambrex Ref BESP302Q), Pro CHO 5-CDM (Cambrex ref12-766Q, catalogue 2003), HyQ SFM4-CHO (Hyclone Ref SH30515-02), HyQ SFM4-CHO-Utility (Hyclone Ref SH30516.02), HyQ PF293 (Hyclone ref SH30356.02), HyQ PF Vero (Hyclone Ref SH30352.02), Excell 293 medium (SAFC Biosciences ref 14570-1000M), Excell 325 PF CHO Protein free medium (SAFC Biosciences ref 14335-1000M), Excell VPRO medium (SAFC Biosciences ref 14560-1000M), Excell 302 serum free medium (SAFC Biosciences ref 14312-1000M), Excell 65319, Excell 65421, Excell 65625, Excell 65626, Excell 65627, Excell 65628, Excell 65629 (JRH Biosciences), Excell MDCK SFM (SAFC-Biosciences Ref. 14581C), Excell MDCK Prod (Ref. M3678), Gene Therapy Medium 3 (animal component free) (SIGMA-Aldrich, ref. G-9916 or Excell GTM-3) (hereinafter named G9916 medium), HYQ CDM4 HEK-293 (Hyclone Ref. SH30859), HYQ SFM4 HEK-293 (HYCLONE Ref. SH30521), AEM (InVitrogen). According to the first preferred embodiment, the serum-free medium No 1 and the serum-free medium No 2 are the same medium. According to a second preferred embodiment the serum-free medium No 1 and the serum-free medium No 2 have a different composition.

The process of the invention encompasses the removal of the whole or a part of serum-free medium 1, followed by its replacement by serum-free medium No 2. However, it is more convenient to remove a substantial fraction (e.g., up to about 50%) of the serum-free medium 1 and then replenish it with the serum-free medium No 2 while still removing medium 1, e.g., through the spinfilter. According to a preferred embodiment, serum-free medium No 2 is directly added to serum-free medium No 1 without removal of a part of serum-free medium No 1. Between 0.25 to 10 volumes of serum-free medium No 2 is added to 1 volume of serum-free medium No 1. In a preferred embodiment, between around 0.5 to 8 volumes of serum-free medium No 2 is added to 1 volume of serum-free medium No 1. In a more preferred embodiment, between around 3 to 6 volumes of serum-free medium No 2 is added to 1 volume of serum-free medium No 1.

The serum-free medium No 1 and/or the serum-free medium No 2 may be supplemented with at least one ingredient selected from the group consisting of amino-acids, lipids, fatty acids, cholesterol, vitamins, carbohydrates, protein hydrolyzates of non-animal origin, and a mixture thereof.

Alternatively, the process of replicating a virus of the invention is a fed-batch process that comprises the additional step of feeding the cells with at least one ingredient selected from the group consisting of amino-acids, lipids, vitamins, carbohydrates, protein hydrolyzates of non-animal origin, surfactant and a mixture thereof. According to a first preferred embodiment, the feeding occurs during steps a) to d) of the process of the invention of replicating a virus, alternatively only during the steps b) to d), or alternatively only during the steps d). The feeding may occur either on a daily basis or on a continuous basis. When the feeding is discontinuous, the feeding may occur one time per day, more than one time per day, or less than one time per day.

The SFM media of the invention comprise a number of ingredients, including amino acids, vitamins, organic and inorganic salts, sources of carbohydrate, each ingredient being present in an amount which supports the cultivation of a cell in vitro. However, in order to improve cell growth or viral productivity, additional ingredients are added to SFM media.

The choice of amino-acid(s) to add to the cell culture may be determined be an analysis of amino-acids consumption by the cells in the culture; such consumption varies according to cell species. According to a preferred embodiment, the amino-acids added to the medium may be selected from the group consisting of asparagine and glutamine, or a mixture thereof. In a more preferred embodiment, glutamine is added for chicken EBx cell culture and the feeding of glutamine is performed during step a) to d) to maintain the glutamine concentration in the medium between around 0.5 mM to around 5 mM, preferably between around 1 mM to around 3 mM, and most preferably around 2 mM. In a preferred embodiment, the feeding of glutamine occur on a continuous basis. Interestingly, duck EBx® cells do not consume much glutamine, because duck cells have the ability to synthesize glutamine. Therefore, glutamine may or may not be added for duck EBx cell culture.

According to a preferred embodiment, the carbohydrates added to the medium are selected from the group consisting of D-glucose, D-sucrose and D-galactose or a mixture thereof. According to a more preferred embodiment, the carbohydrate added is D-glucose. The feeding of D-glucose is performed during step a) to d), more preferably between b) to d) to maintain the D-glucose concentration in the medium between around 0.5 g/l to 25 g/l of D-glucose, preferably between around 1 g/l to 10 g/l of D-glucose, preferably around 2 to 3 g/l of D-glucose. In a preferred embodiment, the feeding of D-glucose occur on a continuous basis.

According to a preferred embodiment, the lipids are selected from the group consisting of cholesterol, steroids, and fatty acids such as palmitic acid, palmitoleic acid, stearic acid, oleic acid, linoleic acid, linolenic acid, and their derivatives, or a mixture thereof. More preferably the fatty acids are from SIGMA-ALDRICH (Ref. F7050) and around 0.35 it/ml of fatty acids solution is added to the culture medium.

The medium may contain auxiliary substances, such as buffer substances like sodium bicarbonate, oxidation stabilizers, stabilizers to counteract mechanical stress, or protease inhibitors. If required, a non-ionic surfactant, such as polypropylene glycol (PLURONIC F-61, PLURONIC F-68, SYNPERONIC F-68, PLURONIC F-71 or PLURONIC F-108) can be added to the medium as a de-foaming agent. These agents are generally used to protect cells from the negative effects of aeration since, without an addition of a surfactant, the ascending and bursting air bubbles can lead to damage of those cells that are located on the surface of these air bubbles ("sparging"). The quantity of nonionic surfactant is preferably between about 0.05 and about 10 g/L, typically between about 0.1 and about 5 g/L. According to another embodiment of the invention, the concentration of surfactant in cell culture medium may be modified to adapt (i.e increase or decrease) the size of the cell clumps.

According to an embodiment of the process of replicating a virus of the invention, the addition of serum-free medium No 2 to the cell culture, is performed after infection step b), preferably between around 0.5 to 4 hour after step b), and more preferably around 1 hour after step b). According to another embodiment of the invention, the addition of serum-free medium No 2 to the cell culture, is performed before infection step b), preferably between around 0.5 to 4 hour after step b), and more preferably around 1 hour before step b). According to another embodiment of the invention, the addition of serum-free medium No 2 to the cell culture, is performed simultaneously to infection step b. The viral infection of step b) is carried out at an m.o.i (multiplicity of infection) of about 10 to $10^{-8}$, preferably $10^{-1}$ to $10^{-6}$, more preferably about $10^{-2}$ to $10^{-6}$, and more preferably about $10^{-4}$. The man skilled in the art will determine the optimal m.o.i according to the virus type. In step c), the infected cells are preferably cultured during at least 24 h, at least 48 h, at least 72 h, at least 96 h, at least 120 h, at least 144 h. When the virus is a poxvirus, the infected cells are cultured at least 144 h.

In the process of the invention, the cell culture of step a) is carried out by batch culture, repeated batch culture, fed-batch culture or perfusion culture. More preferably, the cell culture of step a) is performed by fed-batch culture. The infection in step b) is performed when the cell density is at least around 4 million, preferably 6 million cells/ml, more preferably 8 million cells/ml in batch or fed-batch process. When a perfusion process is used, the infection in step b) is performed when the cell density is of at least at least 8 million cells/ml, preferably around 9 to 10 million cells/ml, or even higher.

The pH of the serum-free culture medium in steps a), b), c) and d) is preferably monitored by the bioreactor. The pH shall be in a range from 6.5 to 7.8, preferably around 6.8 to 7.5, and more preferably around 7.2.

In the process of the invention, step d) lasts for 1 to 10 days before the harvest. According to a preferred embodiment, step d) lasts for 2 to 5 days before the harvest. The time of harvest (step e) is defined according to the cell density in the cultivation vessel. The inventor have now found that the optimal time for harvest the viruses is two days after the density of viable cells have reached its optimal level and have started to decrease because of viral infection.

The cell culture is performed at a temperature comprises between 32° C. to 39° C. depending of the virus type. For influenza virus and poxvirus production, cell culture infection is preferably performed at 33° C.

EBx® cells have the ability to grow in suspension culture with cells clumped in loose aggregates of few cells, up to more than hundred(s) of cells. Without to be bind by a theory, the size of the clumps may vary according to the composition of cell culture medium. For example, presence of surfactant such as polypropylene glycol (PLURONIC F-61, PLURONIC F-68, SYNPERONIC F-68, PLURONIC F-71 or PLURONIC F-108), the stirring, the concentration of divalent ions, such as Mg2+ and Ca2+, may have an effect on the clumps size. The inventor has now found that the viral yield may be increased by allowing the EBx® cells of the invention to aggregate to each others to form clumps during at least step a) of the process. During the scaling-up from the master and working cell bank vial through the various sizes of T-flasks or roller-bottles to bioreactors, the suspension cells are generally passaged to a larger vessel, either by dilution into fresh medium or by centrifugation followed by a re-suspension of cell pellet into a fresh medium. The inventor has found that during the cells passages, it is recommended to keep large cell clumps into the culture. To do so, it is better not to disrupt cells clumps in order to improve the replication of virus in EBx® cells. For example, during the initial phases of culture of step a) in T-flasks or roller-bottles, it is recommended to dilute the cell culture to passage the cells into larger vessel(s), and it is not recommended to centrifuge, nor to disrupt the cells clumps by pipetting or stirring. However, too large clumps may be suboptimal for a high viral production. Consequently, the man skilled in the art will define whether a partial disruption of the clumps, by pipetting or stirring, during initial cell passages of step a) may improve viral yield. According to a preferred embodiment, poxviruses, and preferably MVA, ALVAC and Fowlpox viruses are obtained by a process of the invention that include the step a) of proliferating clumped EBx® in loose aggregates of few cells, up to more than at least one hundred of cells, at least two hundred of cells, at least five hundred of cells, at least thousand(s) of cells.

The inventors have found that size of EBx® cells clumps, preferably duck EBx® cells clumps, may be dependent of Mg2+ and/or Ca2+ ions concentration in anchorage-independent cell culture medium. Since too large clumps may be suboptimal for a high viral production, the size of clumps may be monitored by adjusting Mg2+ and Ca2+ concentration in cell culture medium. For duck EBx® cells, the cell culture medium preferably contain Mg2+ concentration comprises between 0.5 mM and 2.5 mM, preferably around 1.6 mM, and Ca2+ concentration comprises between 0.01 mM and 0.5 mM, preferably around 0.1 mM.

The invention also relate to the virus obtainable by a process of the invention. The instant invention also relates to the vaccine containing the virus of the invention. The process of manufacturing a viral vaccine comprises the process of replicating a virus according to the invention wherein the step e) of virus harvest is comprising at least one step selected among filtering, concentrating, freezing and stabilizing by addition of stabilizing agent. The virus harvest is performed according to technologies well-known to the man skilled in the art. According to a preferred embodiment, the step of harvesting said virus comprises collecting cell culture supernatant obtained from centrifugation of cell culture, then filtering, concentrating, freezing and stabilizing virus preparation by addition of stabilizing agent. For example, for influenza virus see Furminger, In Nicholson, Webster and Hay (Eds) Textbook of influenza, chapter 24 pp 324-332.

The process of manufacturing a viral vaccine according to the invention may also comprise the additional step of inactivation of harvested virus. Inactivation is preferably performed by treatment with formaldehyde, beta-propiolactone, ether, ether and detergent (i.e such as Tween 80™), cetyl-trimethyl ammonium bromide (CTAB) and Triton N102, sodium deoxycholate and tri(N-butyl)phosphate.

According to another embodiment, the invention also relates to a process of preparation of viral antigenic proteins from the virus obtainable by a process of the invention, said process comprises the additional steps of:
a) optionally, incubating cell culture supernatant comprising whole virus with a desoxyribonucleic acid restriction enzyme, preferably DNAses (see EC3.1.21 and EC3.1.22 classification) and nucleases (see EC3.1.30 and EC3.1.31 classification). Preferably, DNA digestion enzyme is benzonase (Benzon nuclease) or DNase I;
b) adjunction of cationic detergent. Examples of cationic detergent are; without limitation: cetyl-trimethyl ammonium salt such as CTAB, myristyl-trimethyl ammonium salt, lipofectine, DOTMA and Tween™;
c) isolation of antigenic proteins. This latter step may be realized by centrifugation or ultrafiltration.

The virus in the vaccine may be present either as intact virus particles, or as disintegrated virus particles. According to an embodiment, the vaccine is a killed or inactivated vaccine. According to another embodiment, the vaccine is a live attenuated vaccine wherein said vaccines mainly comprises EBx cell culture supernatant obtainable by the process of the invention, preferably without serum, optionally filtered and/or concentrated and comprising said virus. According to a third embodiment, the vaccine is comprising viral antigenic proteins obtainable from a virus prepared according to the process of the invention.

The invention also pertain to provide a vaccine comprising an infected cell line EBx®, preferably duck or ev-O chicken EBx®, obtainable by the process of the invention, and wherein infected cell line EBx®, preferably duck or ev-O chicken EBx®, are harvested in step d).

The vaccine of the invention may comprise the virus of the invention in combination with pharmaceutically acceptable substances which increase the immune response. Non limiting examples of substances which increase the immune response comprises incomplete Freund adjuvant, saponine, aluminium hydroxide salts, lysolecithin, plutonic polyols, polyanions, peptides, bacilli Calmette-Guerin (BCG) and corynebacterium parvum. Example of synthetic adjuvant is QS-21. In addition, immuno-stimulating proteins (interleukins Il1, Il2, IL3, IL4, IL12, IL13, granulocyte-macrophage-colony-stimulating factor, . . . ) may be used to enhance the vaccine immune response.

The vaccine of the invention is preferably a liquid formulation, a frozen preparation, a dehydrated and frozen preparation, optionally adapted to intra-nasal route of administration.

The vaccine of the invention is use for the prophylactic and/or therapeutic treatment of a human or an animal infected by a virus previously listed. Preferably, the viral vaccine of the invention is preferably use for the prophylactic and/or therapeutic treatment of a human infected by a virus selected among smallpox, influenza, measles, mumps, rubella viruses, RSV. Alternatively, the vaccine of the invention is preferably use for the prophylactic and/or therapeutic treatment of a animal infected by a virus selected among influenza, Newcastle Disease Virus, Egg Drop Syndrome Virus, Infectious Bursal Disease, Infectious Bronchitis Virus, Canine Distemper virus, Chicken Anemia Virus. The recombinant viral vaccine of the invention may also be used for the prophylactic and/or therapeutic treatment of chronic diseases such as cancer and infectious diseases such as AIDS.

The EBx® cell lines of the invention are useful to generate and produce re-assorted virus. The virus with a segmented genome, such as influenza virus may be re-assorted. When infecting simultaneously EBx® cells of the invention with at least two different strains of influenza virus, a mix of segmented genome from two different strains is present in the same host cell. During virus assembly, all combination of genomic segments can theoretically be generated. Specific reassorted virus may thus be isolated by selecting or eliminating, with an antibody for example, virus with a desired traits (See Kilnourne E. D in Plotkin S A and Mortimer E. A. Eds, Vaccines 1994). The EBx® cell lines of the invention are also useful to generate and produce influenza virus by reverse genetics (See Enami, Proc. Natl. Acad. Sci. USA, 87:3802-3805 (1990); Enami et Palese, J. Virol. 65:2511-2513 (1991); Luytjes, Cell 59:1107-1113 (1989)).

The present invention also relates to the use of EBx® cell lines of the invention as a cell substrate to perform virus titration. EBx® cells will efficiently in replace current cell system, such as embryonated eggs, CEFs, DF1 cells and others, used to determine the titer of a viral solution. Preferable the viral titration is performed by TCID50 method (Reed L, Muench H, 1938. A simple method of estimating fifty percent endpoints. *Am. J. Hyg.* 27, 493-97).

The present invention also relates to the use of EBx® cell lines of the invention as a cell substrate to perform sanitary testing.

The invention also relates to the diagnostic composition containing viruses of the invention or constituents thereof.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. For the remainder of the description, reference will be made to the legend to the figures below.

FIGURES

FIG. 1: Anchorage-independent chicken EBx cells

FIG. 1A: Anchorage-independent chicken Valo EBv13 cells in serum free-medium.

EBv13 cells were cultured at 37° C. in suspension serum-free medium Excell 65319 (SAFC). EBv13 cells have an homogeneous size and grow in loose clumps into culture. The population doubling time is about 16-18 Hours and the cell density reached in agitated flask vessels were about 4-5 millions cells/ml.

FIG. 1B: Anchorage-independent chicken EB Line 0 cells in serum free-medium

EB Line 0 cells were cultured at 39° C. in suspension serum-free medium Excell 66444 (SAFC). EB Line 0 cells have an homogeneous size and grow in loose clumps.

FIG. 2: Chicken Valo EBv13 cells express high level of Telomerase

EBv13 cells at passage p193 do express high level of telomerase in the same order of magnitude that chicken EB14-074 cells (see WO03/076601) at passage p164 (Master cell Bank: MCB) or at passage p184 (Workin Cell bank: WCB). Murine embryonic stem cells (mES) were used as a positive control and mouse fibroblast (FED) were used as a negative control.

Figure 3A:
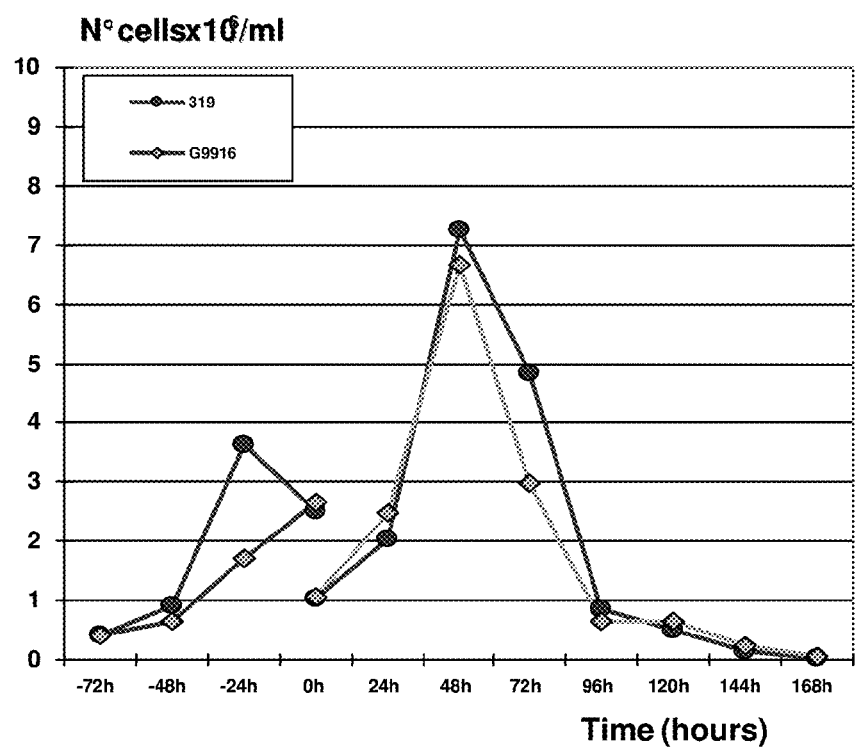
Figure 3B:
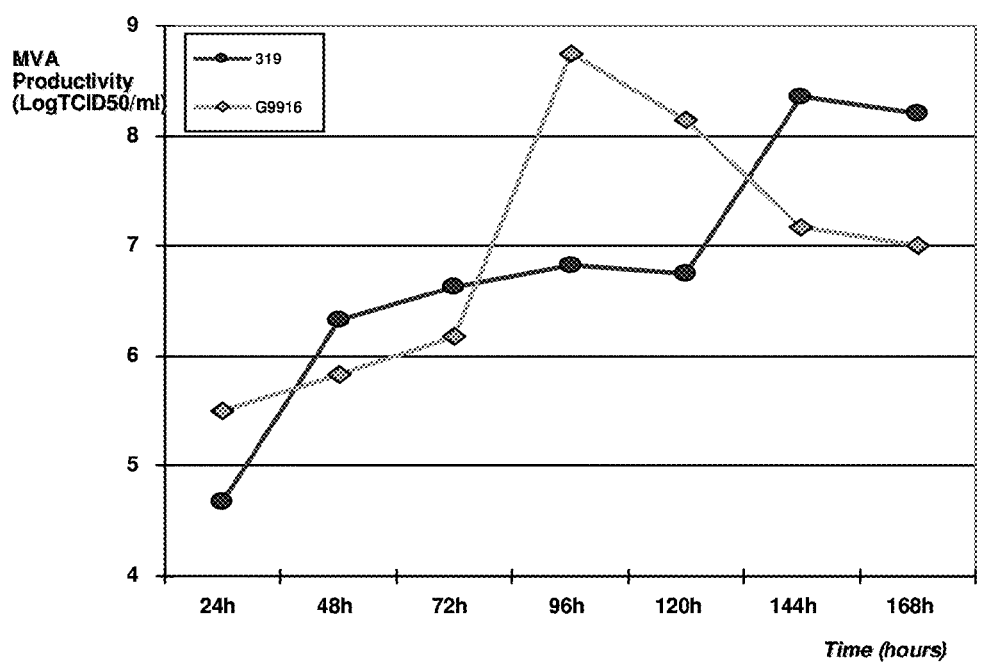

FIGS. 3A and 3B: Susceptibility of Chicken Valo EBv13 to poxvirus

EBv13 (passage 188) were seeded at 0.4×106 cells/ml in 100 mL F175 flasks either in 40 ml of SFM Excell Medium 65319 or G9916 SFM Medium (SAFC) supplemented with 4 mM Glutamine. The cell growth and infection with MVA-GFP (MOI $10^{-2}$ TCID50/cell) were performed at 37° C. One hour post infection, 60 ml of fresh medium were added.

FIG. 3A: cell density kinetics in SFM Excell Medium 65319 or G9916 SFM Medium (SAFC).

FIG. 3B: MVA productivity expressed in TCID50/ml in SFM Excell Medium 65319 or G9916 SFM Medium (SAFC).

FIGS. 4A, 4B and 4C: Transmission Electronic Microscopy analysis of duck EBx cells FIG. 4A: Micrograph of anchorage-independent duck EBx cells.

FIG. 4B: Transmission Electronic Microscopy analysis of dEBx cells were performed by Dr. A Rivoire (Lyon, France). Duck EBx cells display a typical embryonic stem cells morphology (i.e high nucleo-cytoplasmic ratio) that resemble the phenotype of murine embryonic stem cells and VIVALIS EB14 cells described in WO2006/108846. Duck EBx cells are small round cells with a large nucleus and nucleolus, with short pseudopodia extending from the plasma membrane. They are highly metabolic active with a ribosome and mitochondria rich cytoplasm.

FIG. 4C: Micrograph of duck EBx cells able to grow in suspension, isolated during feeder deprivation, and adapted to grow without additives and serum.

Figure 5A:
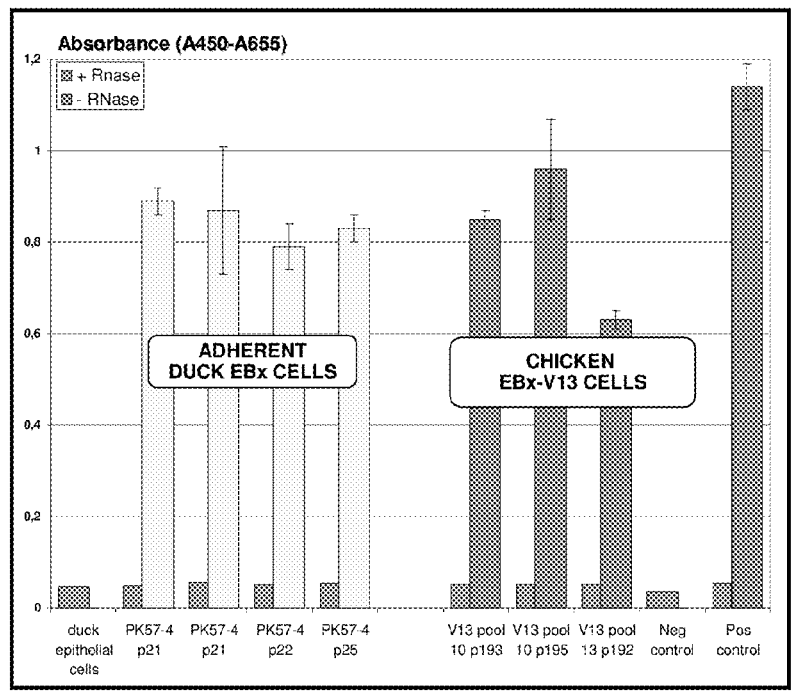
Figure 5B:
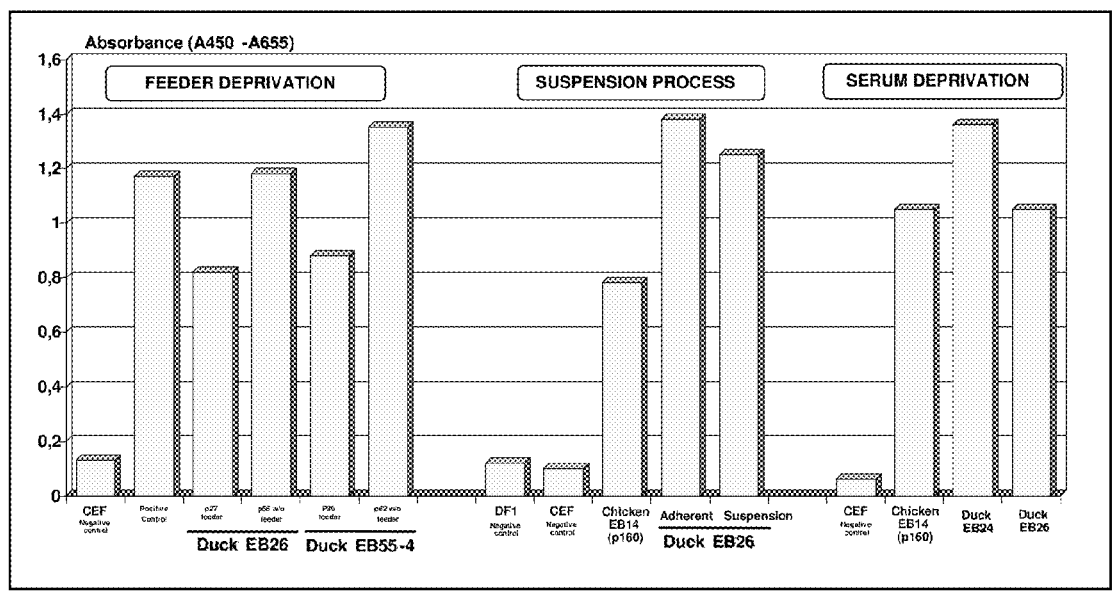

FIGS. 5A and 5B: Telomerase expression in duck EBx cell lines

Telomerase expression during different stages of establishment of duck EBx cells was investigated by using Roche telomerase detection kit (Telomerase OCR ELISA).

FIG. 5A: Telomerase is found to be highly expressed in different adherent duck EBx cell lines just like in chicken EBv13 cells. Duck epithelial cells used as a negative control do not express telomerase.

FIG. 5B: During the process of establishment of suspension duck EBx cells, high level of telomerase expression is maintained. High level of telomerase were investigated in duck EBx cells during feeder deprivation (with or without feeder cells), during the process of adapting duck EB26 cells to suspension and after serum deprivation of dEB24 et dEB26.

Duck EBx cells, such as EB24 and EB26, express high level of telomerase just like chicken EB14 cells. Duck EB66 also express high level of telomerase (Data not shown).

Figure 6A:
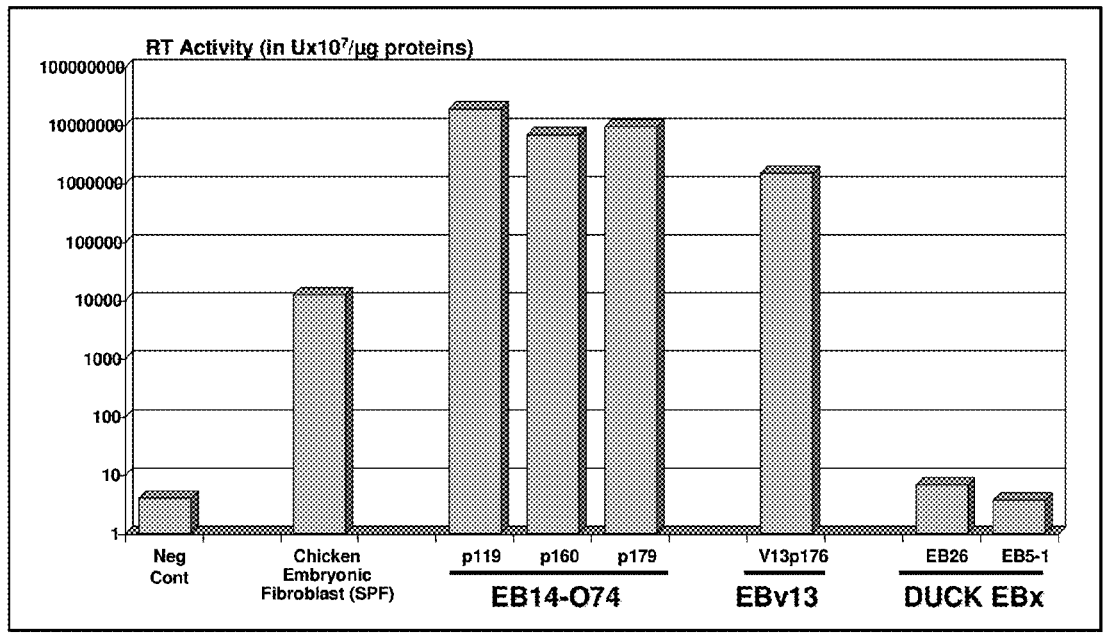
Figure 6B:
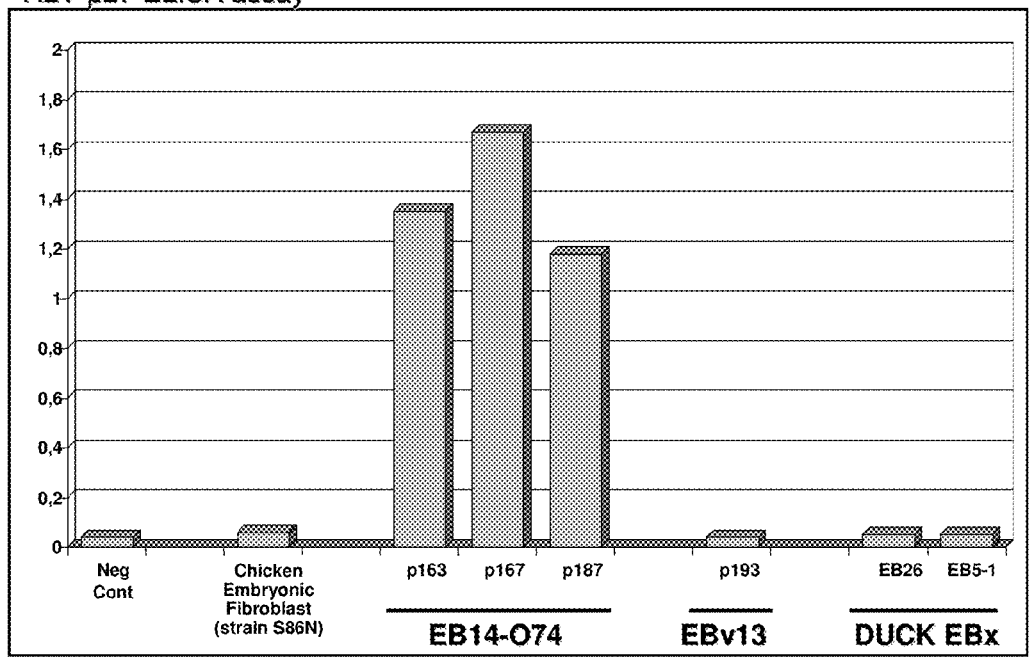

FIGS. 6A and 6B: Duck EBx® cells display no endogenous reverse transcriptase activity FIG. 6A: Endogenous reverse transcriptase expression was investigated by direct F-PERT analysis (Lovatt et al., 1999, J. Virol. Methods, 82:185-200) in Clean Cells (FRANCE). Duck EBx® cell lines, EB26 and EB5-1, display no endogenous Reverse Transcriptase (RT) activity. High level of RT activity were detected in chicken EB14 and EBv13 cells culture (at different passages) as well as, to a lesser extend, in chicken embryonic fibroblast (CEF) derived from Specific Pathogen Free (SPF) chicken strain. CEM cells, which are RTase negative, were used as a negative control to set the detection limit of the assay.

FIG. 6B: Presence of endogenous retroviral particles, either replicative (i.e replication competent) or non-replicative, in the cell culture supernatant of duck and chicken EBx cells were investigated by an ELISA assay detecting the avian leukosis major capsid antigen P27. Duck EBx cell lines, EB26 and EB5-1, as well as chicken EBv13 do not secrete ALV p27 antigen. In the opposite, chicken EB14 cells do express ALV P27 antigen.

Figure 7A:
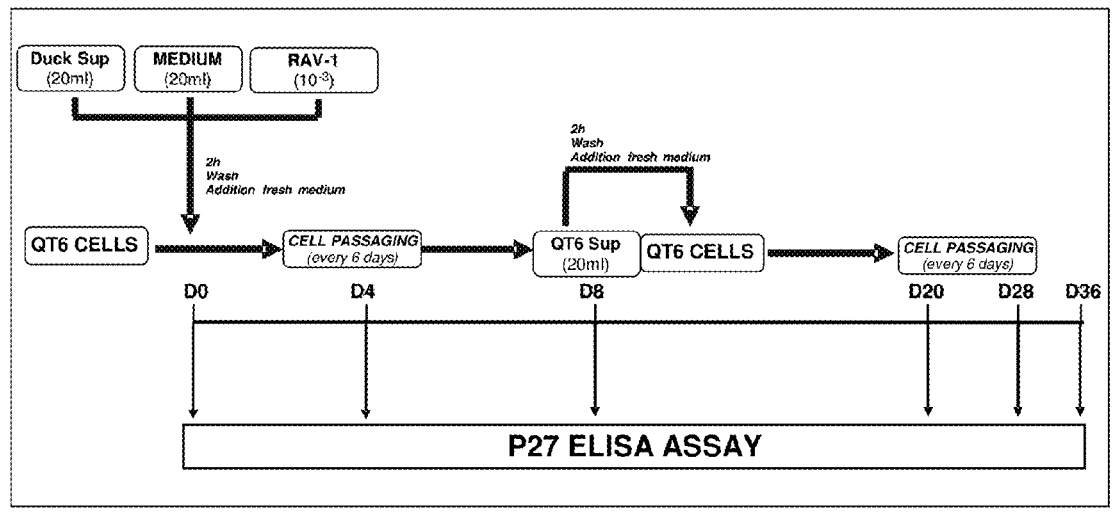
Figure 7B:
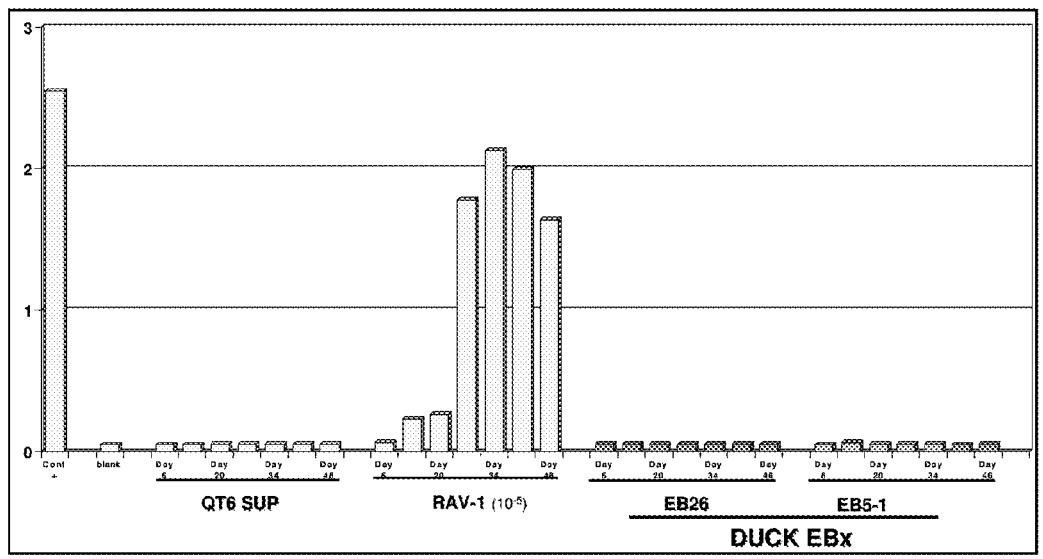

FIGS. 7A and 7B: Duck EBx cells do not secrete replicative avian leucosis virus (ALV) Co-cultivation assay of duck EBx cells with quail QT6 cell line, known to be sensitive to endogenous and exogenous ALVs, were performed in Bioreliance (UK) to detect the presence of endogenous replicative duck viruses.

FIG. 7A: described the principle of QT6 co-culture.

FIG. 7B: The presence of replicative virus is detected by an ELISA assay detecting the avian leukosis major capsid antigen P27.

The assay demonstrates that none of duck EBx® cells tested (dEB26 and dEB51) secrete replicative ALV. RAV-1 virus, which is known to replicate in QT6, were used as a positive control.

Figure 8:
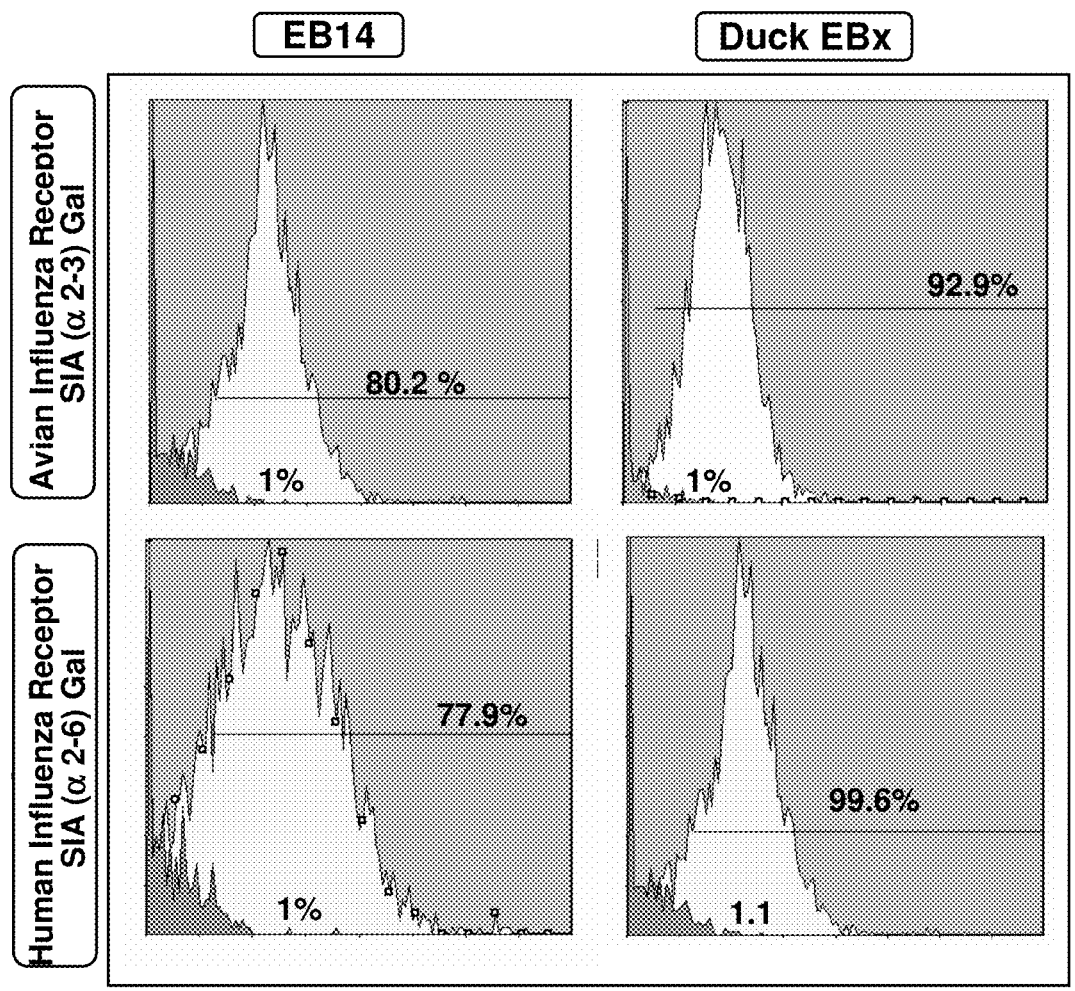

FIG. 8: Cell surface expression of receptors SAα2-3 and SAα2-6 in duck EBx and chicken EB14 cell lines Cells are incubated with digoxygenin labelled lectins: *Sambuca nigra* agglutinin lectin specifically binds to Sia2-6Gal, while *Maackia amurensis* agglutinin lectin specifically binds to Sia2-3Gal. Lectins that bind to cells are revealed with anti-digoxygenin antibody FITC-labelled according to well-known techniques by the man skilled in the art. FITC-labelled cells are numbered with a fluorescent cell sorter (FACS). SAα2-3 and SAα2-6 molecules are been described to be the receptors for the avian and human influenza viruses, respectively. Almost all duck EBx cells highly express cell surface receptors SAα2-3 and SAα2-6.

Figure 9A:
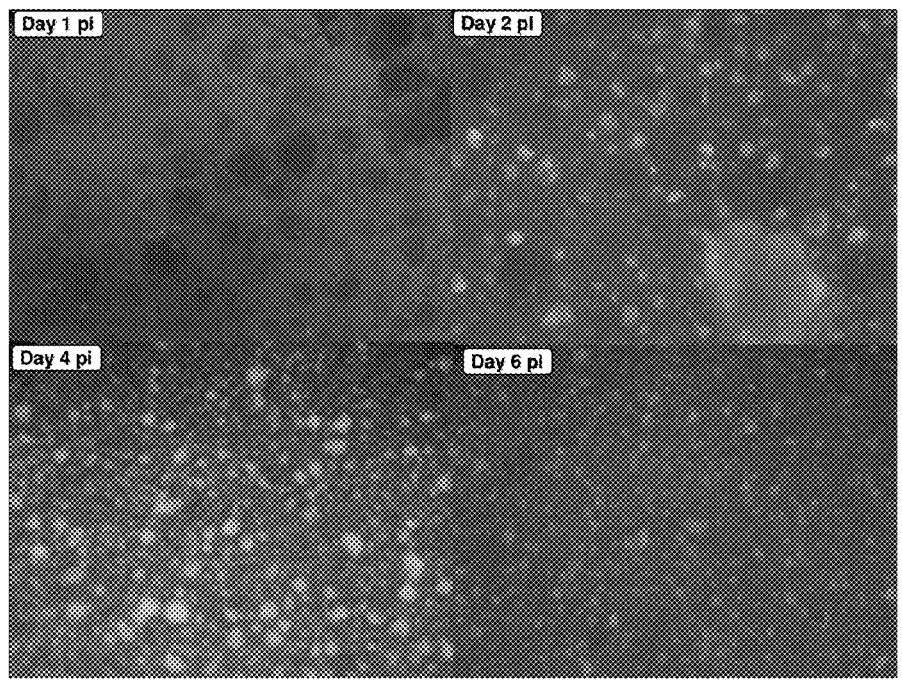
Figure 9B:
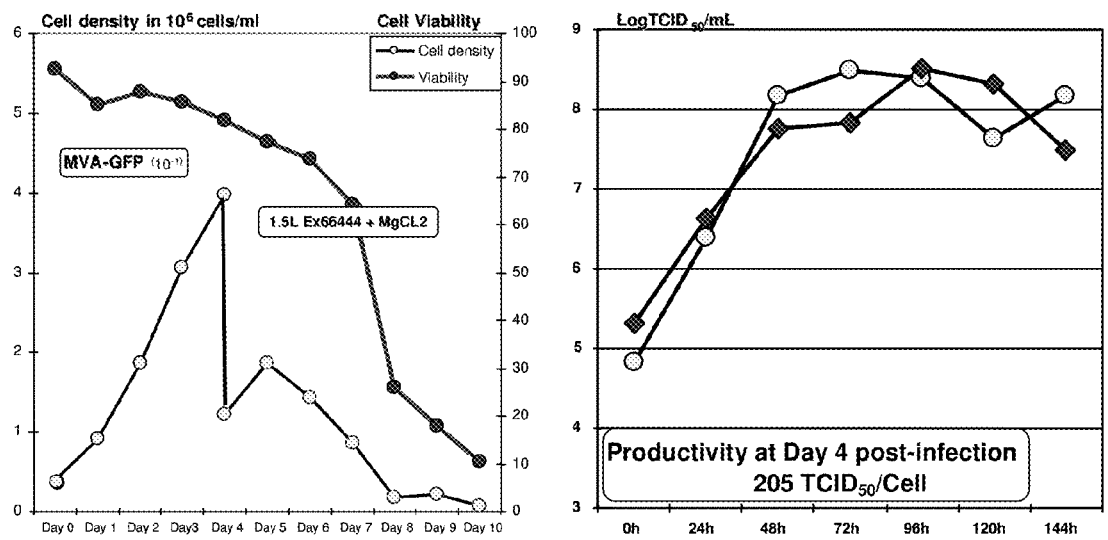

FIGS. 9A and 9B: MVA-GFP virus propagation in infected duck EBx cells

FIG. 9A: Duck EBx® were allowed to form small clumps in T175 stirred tank flasks during cell proliferation in a cell growth SFM medium. Clumps were then infected with $10^{-2}$ $TCID_{50}$/cell of MVA-GFP virus and the mixture was diluted in production SFM media. During a 6 days virus propagation period at 37° C., pictures of UV-exposed infected cells were taken daily. The pick of MVA infection was reached at day 4 post-infection (pi). At day 6 pi, the infected cells start to die.

FIG. 9B: MVA-GFP virus titration propagated in duck EBx® cells in a 3 L fed-batch bioreactor. (Left Panel) Duck EBx-derived biomass was allowed to accumulate during cell proliferation phase in Excell growth medium (SAFC). At day 4, cell density reached 4 million cells/ml. Cells were then infected with $10^{-1}$ TCID$_{50}$/cell of MVA-GFP virus and the mixture was diluted in 1.5 L Excell medium. During a 6 days virus propagation period at 37° C., samples were collected daily and TCID$_{50}$ titration (Right Panel) was performed at the end of the kinetic. A yield of 8.5 log TCID50/ml were reached at 4 p.i. corresponding to a yield of 205 TCID$_{50}$/Cell.

FIGS. 10A and 10B: Influence of Calcium and Magnesium concentration in SFM medium on the size of EBx® cells clumps FIG. 10A: Chicken EBv13 cells were first cultured in the SFM medium from SAFC Biosciences that comprise a high concentration of calcium (Ca2+) (Approx. 0.79 mM) and magnesium (Mg2+) ions; in this medium, cells produce large aggregates in culture. Three days after having changed the cell culture medium with the same SFM medium that comprises a lower concentration of Ca2+ (0.03 mM final) and Mg2+ (1.6 mM final), the cells form smaller aggregates.

FIG. 10B: Duck EB24, EB26 and EB66 cells were first cultured in the SFM medium from SAFC Biosciences that comprise a high concentration of calcium (Ca2+) (Approx. 0.79 mM) and magnesium (Mg2+) ions; in this medium, cells produce large aggregates in culture. Three days after having changed the cell culture medium with the same SFM medium that comprises a lower concentration of Ca2+ (0.03 mM final) and Mg2+ (1.6 mM final), the cells form smaller aggregates.

Figure 11A:
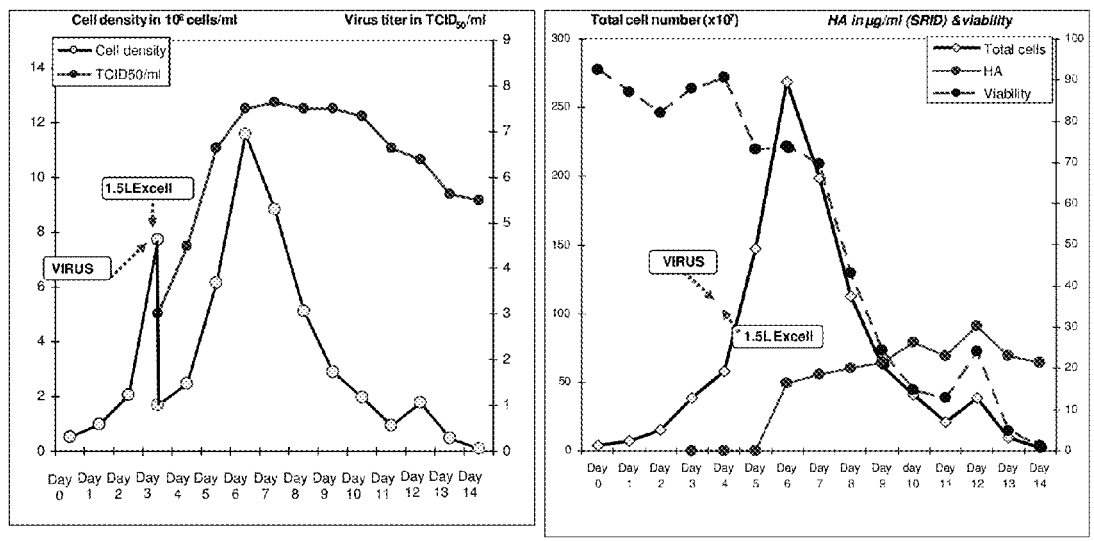
Figure 11B:
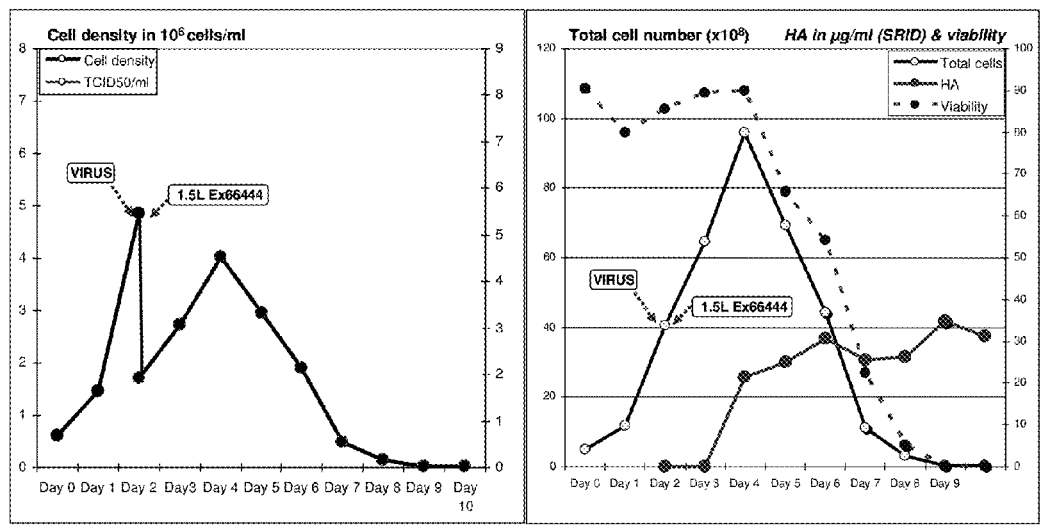

FIGS. 11A and 11B: Production of influenza virus strains A in duck EBx cells in 3 L-bioreactors Duck EBx® biomass was allowed to accumulate at 37° C. during cell proliferation phase in a cell growth medium. Cells were then infected with $10^{-4}$ TCID$_{50}$/cell of A/H1N1/Beijing/262/95 or A/H3N2/New York/55/2004 influenza virus, the mixture was diluted in 1.5 L Excell production medium supplemented with 0.75 USP/mL of trypsin and temperature was lowered to 33° C. During a 14 days virus propagation period, samples were collected daily and stored at −80° C.

FIG. 11A: Growth kinetic of duck EBx cells infected with A/H1N1/Beijing/262/95 influenza virus strain Left panel: Cell density (rhombus, ×10$^6$ cells·ml) and viral titer in log TCID$_{50}$/ml.

Right panel: Total number of cells (square), viability (black circles, %) and haemagglutinin concentration in ug/ml (red circles, %).

The viral yield reached 20 ug of Hemagglutinin per ml of culture supernatant.

FIG. 11B: Growth kinetic of duck EBx cells infected with A/H3N2/New York/55/2004 influenza virus strain Left panel: Cell density (rhombus, ×10$^6$ cells·ml$^{-1}$)

Right panel: Total number of cells (square), viability (black circles, %) and haemagglutinin concentration in ug/ml (red circles, %).

The viral yield reached 30 ug of Hemagglutinin per ml of culture supernatant.

Figure 12:
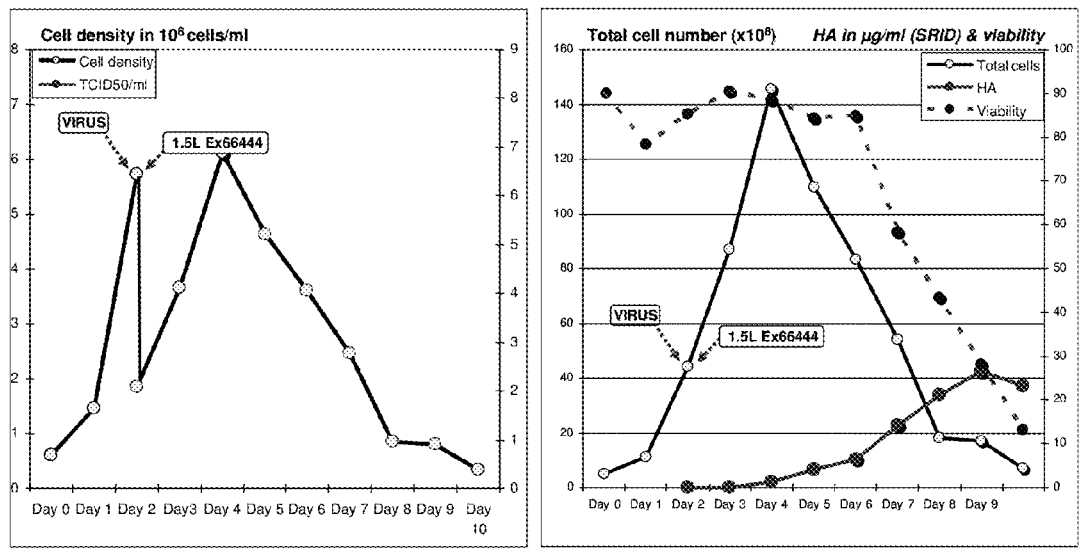

FIG. 12: Production of influenza virus strain B in duck EBx® cells

Duck EBx® biomass was allowed to accumulate at 37° C. during cell proliferation phase in a cell growth medium. Cells were then infected with $10^{-3}$ TCID$_{50}$/cell of B/Jiangsu/10/2003 influenza virus, the mixture was diluted in 1.5 L Excell production medium supplemented with 0.75 USP/mL of trypsin and temperature was lowered to 33° C. During a 14 days virus propagation period, samples were collected daily and stored at −80° C.

Left panel: Cell density (rhombus, ×10$^6$ cells·ml$^{-1}$)

Right panel: Total number of cells (square), viability (black circles, %) and haemagglutinin concentration in ug/ml (red circles, %).

The viral yield reached 25 ug of Hemagglutinin per ml of culture supernatant.

Figure 13:
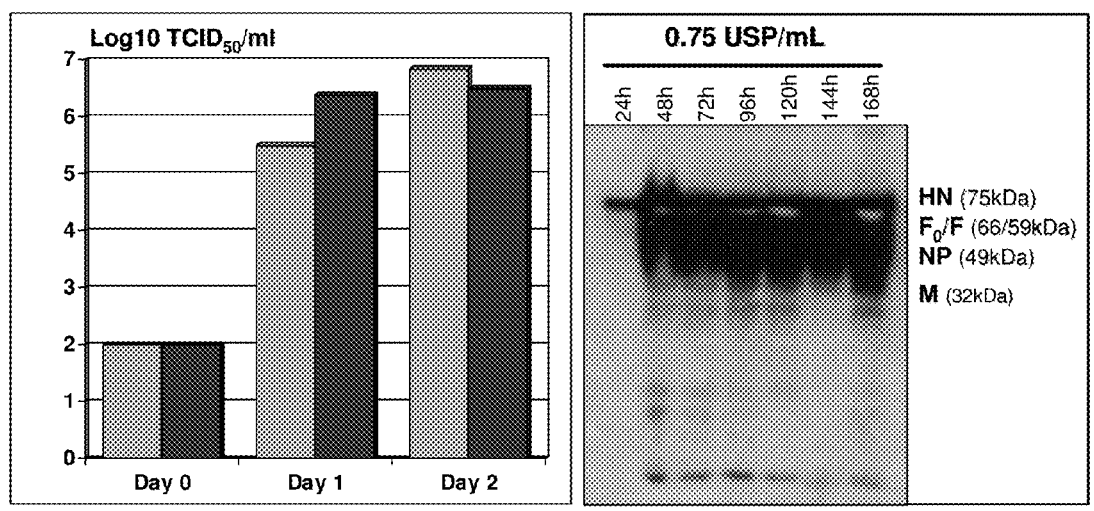

FIG. 13: Analysis of NDV productivity and viral protein expression in suspension duck EB66 cells (MOI $10^{-3}$, 0.75 USP/mL trypsin)

Duck and chicken EBx cells are sensitive to and replicate NDV La Sota strain. Titers (in TCID50/ml) of NDV produced in duck EB66 cells increase from day 0 to day 2 pi to reach an average of $10^{6.83}$ $_{TCID50}$/ML (FIG. 13 Left Panel).

Western blot analysis (FIG. 13 right Panel) showed NDV viral proteins (HN, Fo/F, NP & M) expression. The viral proteins composition of NDV virus produced in duck EB66 cells are similar to the one obtained with NDV virus produced in chicken EB14 cells. In addition, the kinetic of release for viruses produced in chicken and Duck EBx cells are similar.

Figure 14:
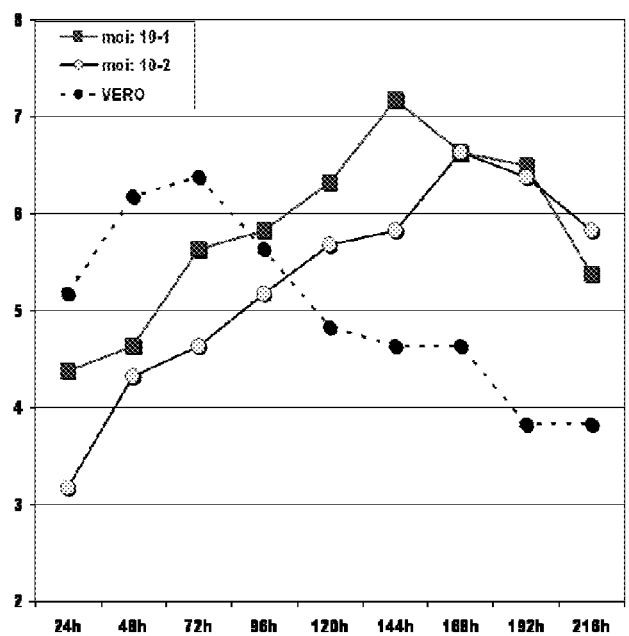

FIG. 14: Analysis of recombinant Measles virus replication in suspension duck EB66 cells (MOI $10^{-1}$ or $10^{-2}$) in tissue-culture flasks in serum free medium. Duck EB66 cells are at least as sensitive as VERO cells to infection by Measles Virus. Titers (in TCID50/ml) of recombinant Measles virus expressing Green Fluorescent Protein (GFP) produced in duck EB66 cells reach $10^7$ TCID50/mL at day 6 post-infection.

FIGS. 15A and 15B: SSEA-1, EMA-1 & Telomerase expression in duck EB66 cells Telomerase expression at different passages of duck EB66 cultured in roller bottles was investigated by using Roche telomerase detection kit (Telomerase OCR ELISA). SSEA-1 and EMA-1 at different passages of duck EB66 cultured in roller bottles was investigated by FACS analysis.

FIG. 15A: Telomerase is found to be highly expressed in suspension duck EB66 cell line at different passages (138, 144, 147, 150, 154).

FIG. 15B: SSEA-1 and EMA-1 cell surface markers was found to be highly expressed in suspension duck EB66 cell line at different passages (138, 144, 147, 150, 154).

Figure 16:
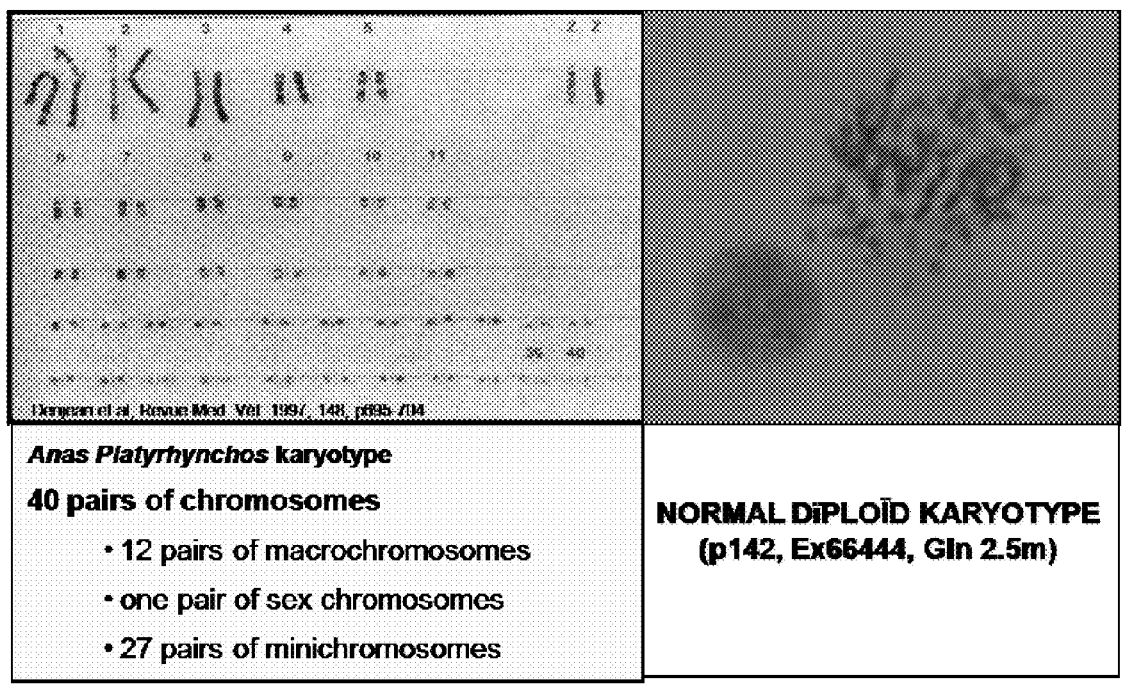

FIG. 16: Karyotype analysis of duck EB66 cells

Duck EB66 cells karyotype was performed by Pr. Franck, ENVL, Lyon. EB66 cells are diploid cells.

EXAMPLES

Example 1

Chicken EBv13 Cell Line from SPF Chicken Strain VALO 1.1—Raw Material

Eggs

Specific Pathogen Free (SPF) strain called Valo. The valo strain is a white Leghorn strain produced and delivered by Lohmann from Germany. Those SPF chicken eggs, supplied with a certificate of analysis, are tested for: CAV, Avian adenoviruses (group 1, serotypes 1-12 and group 3), EDS, Avian Encephalomyelitis Virus, Avian Leukosis Viruses/RSV (including Serotype ALV-J), Avian Nephritis Virus, Avian Reoviruses, Fowlpox Virus, Infectious Bronchitis Virus, Infectious Bursitis Virus (IBDV), Infectious Laryngo Tracheitis Virus, Influenzavirus Typ A, Marek's Disease Virus, Mycoplasmosis (Mg+Ms), *Mycobacterium avium*, Newcastle Disease Virus, Reticuloendotheliosis Virus, *Salmonella pullorum*, Other *Salmonella* Infections, Avian Rhinotracheitis Virus (ART), *Hemophilus paragallinarum*. Valo chicken eggs were only submitted to a disinfection with the decontaminant to avoid any risk of contamination linked to the manipulation of eggs during the transport.

Feeder Cells

In the first step of the process of establishment of EBv13, cells from murine origin (STO cells) were used as feeder layer to maintain the pluripotency of chicken stem cells. Those feeder cells are mitotically inactivated by gamma irradiation (45 to 55 Grays) before seeding on plastic. This dose of irradiation is a sub-lethal dose that induces a definitive arrest of the cell cycle but still permits the production of growth factors and extracellular matrix, necessary for the promotion of the cell growth of non differentiated cells.

The STO cell line was derived by A. Bernstein, Ontario Cancer Institute, Toronto, Canada from a continuous line of SIM (Sandos Inbred Mice) mouse embryonic fibroblasts and it was supplied by the American Type Culture Collection (ATCC) (STO Product number: CRL-1503, Batch number 1198713). Fresh feeder layers were prepared twice a week, in general on monday and thursday. Exponentially cells were dissociated and counted. A part of cells were seeded for maintenance of viable cultures and another part was irradiated. For irradiation, we prepared a cell suspension at $10\times10^6$ cells/mL in tubes. Cells were exposed to a 45 to 55 grey dose and were seeded on plastic. After seeding, dishes or plates coated with inactivated feeder cells were used during a maximum of 5 days Medium
    DMEM-HamF12 (Cambrex, Cat no BE04-687)
    Optipro medium (Invitrogen, Cat no 12309)
    EX-CELL™ 65195, 60947 and 65319 (SAFC, customized medium)

Additives
    Glutamine (Cambrex, Cat no BE17-605E)
    Pencillin/streptomycin (Cambrex, Cat no BE17-602E))
    Non essential Amino Acids (Cambrex, Cat no BE13-114E)
    Sodium pyruvate (Cambrex, Cat no BE13-115)
    Vitamines (Cambrex, Cat no 13-607C)
    Beta Mercapto Ethanol (Sigma, Cat no M7522)

Buffer and Fixators
    PBS 1× (Cambrex, Cat no BE17-516F)
    Paraformaldehyde 4% (Sigma, Cat no P6148)
    KCl 5.6% (Sigma, Cat no P9333)
    Methanol/Acetic acid (3/1): Methanol (Merck, Cat no K34497209; Acetic acid Sigma Cat no A6283)
    Colcemid, Karyomax (Gibco, Cat no 15212-046)

Cryoprotective Agent
    Dimethyl Sulfoxyde (DMSO) (Sigma, Cat no D2650)

Factors
    Two different recombinant factors were used:
    Recombinant Human Ciliary Neurotrophic Factor (CNTF) (Peprotech Inc, Cat no 450-13)
    Recombinant Human Insulin Like Factor I (IGF1) (Peprotech Inc, Cat no 100-11)
    The two factors were produced in *E. Coli* bacteria.

Fetal Bovine Serum
    Non Irradiated Fetal Bovin Serum (FBS) (JRH, Cat No 12103)

The non irradiated serum used in the program was collected and produced in United States. Animals used for collection were USDA inspected and acceptable for slaughter. It was added in the medium during avian stem cells culture. This batch was not submitted to irradiation to avoid the destruction of critical proteins or components identified as essential for the maintenance of stem cells in culture.

Irradiated Serum (JRH, Cat No 12107)

The irradiated batch used in this program was also collected in United States. This irradiated batch was added as supplement in the DMEM medium used for the culture of STO or FED cells (feeder cells). Those cells do not require as stem cells a specific quality of serum for growth and maintenance in culture. To minimize high concentration of serum in the medium we have adapted the STO cells to grow in presence of 4% of FBS only.

Dissociating Agents:
    Pronase (Roche, Cat No 165 921)

Pronase is a recombinant protease manufactured by Roche Diagnostics, Germany, used for the dissociation of adherent avian stem cells.

Trypsine EDTA (Cambrex, Cat No BE17-161E)

Trypsine is used for the dissociation of STO or FED cells and at late passages for the dissociation of avian cells adapted to Serum Free Medium. This enzyme of porcine origin is manufactured aseptically according to cGMP referential conditions by a validated sterile filtration method and tested according to current E.P. The raw material, irradiated prior to formulation, is tested for porcine parvovirus in strict compliance with 9/CFR 113.53.

Non Enzymatic Cell Dissociation Solution (Sigma, Cat No C5914)

This agent of dissociation is a ready to use formulation used to gently detach cells from the growing surface of the culture vessel. The formula contains no protein, and allows dislodging of cells without use of enzymes. Cellular proteins are preserved making possible immunochemical studies that are dependent upon the recognition of cell surface proteins. This enzyme was used to detach cell before FACS analysis of biological markers like EMA-1 (Epithelial Membrane Antigen 1) and SSEA1 (Stage Specific Embryonic antigen-1).

1.2—Process of Establishment of EBv13 Cell Line

Eggs are opened, the yolk were separated from the albumen during the opening. The embryos were removed from the yolk either directly with the aid of a Pasteur pipette, or with the aid of a small absorbent filter paper (Whatmann 3M paper), cut out beforehand in the form of a perforated ring with the aid of a punch. The diameter of the perforation were about 5 mm. These small rings were sterilized using dry heat for about 30 minutes in an oven. This small paper ring is deposited on the surface of the yolk and centered on the embryo which is thus surrounded by the paper ring. The latter is then cut out with the aid of small pairs of scissors and the whole removed is placed in a Petri dish, filled with PBS or with a physiological saline. The embryo thus carried away by the ring were cleaned of the excess yolk in the medium and the embryonic disk, thus free of the excess vitellin, is collected with a Pasteur pipette.

The chicken Valo embryos were placed in a tube containing physiological medium (1×PBS, Tris Glucose, medium, and the like). The Valo embryos were then mechanically dissociated and inoculated on a layer of feeder STO cells into complete culture medium at 39° C. The feeder cells were seeded in flask at around $2.7\times10^4$ cell/cm$^2$. The complete culture medium is composed of basal commercial medium DMEM-Ham F12 supplemented with 10% fetal calf serum, with IGF1 and CNTF at a final concentration of 1 ng/ml, and with 1% non-essential amino acids, with 1% of mixture of vitamins of commercial origin, with sodium pyruvate at a final concentration of 1 mM, with beta-mercapto-ethanol at a final concentration of 0.2 mM, glutamine at a final concentration of 2.9 mM, with an initial mixture of antibiotics containing penicillin at a final concentration of 100 U/ml and streptomycin at a final concentration of 100 µg/ml. Rapidly after the first passages of the cells, the mixture of antibiotics is no longer added to the medium. The expression rapidly is understood to mean after the first 3 to 5 passages in general.

When the avian ES cells from chicken Valo embryos is passaged from a culture dish to another, the seeding of culture dishes was performed with around between $7 \times 10^4/cm^2$ to $8 \times 10^4/cm^2$ of avian ES cells in the complete culture medium. Preferably, the seeding is made with around $7.3 \times 10^4/cm^2$ ($4 \times 10^6$ cells/55 $cm^2$ or $4 \times 10^6$ cells/100 mm dish). The avian cells, preferably the avian embryonic cells of step a) are cultured during several passages in the complete medium. At passage 15, the complete medium was depleted in growth factors IGF1 and CNTF. The depletion is made directly in one step, from one passage to another. The embryonic stem cells, preferably the avian embryonic cells are cultured during several passages in the complete medium without IGF1 and CNTF growth factors.

Then depletion of feeder cells were performed after the depletion of growth factors IGF1 and CNTF by a progressive decreasing of feeder cells concentration over several passages. Practically, the same concentration of the feeder cells were used for 2 to 4 passages, then a lower concentration of the feeder cells were used for an additional 2 to 4 passages, and so on. The flask were originally seeded with around $2.7 \times 10^4$ feeder cells/$cm^2$, then around $2.2 \times 10^4$ feeder cells/$cm^2$, then around $1.8 \times 10^4$ feeder cells/$cm^2$, then around $1.4 \times 10^4$ feeder cells/$cm^2$, then around $1.1 \times 10^4$ feeder cells/$cm^2$, then around $0.9 \times 10^4$ feeder cells/$cm^2$, then around $0.5 \times 10^4$ feeder cells/$cm^2$. Then the flask were seeded with $6.5 \times 10^4$ avian cells/$cm^2$ to $7.5 \times 10^4$ avian cells/$cm^2$ and without feeder cells. The depletion of feeder cells started at around passage 21 and ended at around passage 65. During the depletion of feeder cells, the chicken Valo ES cells were seeded in culture flask at a lower concentration than in step a), about around $4 \times 10^4$ cell/$cm^2$ to $5 \times 10^4$ cell/$cm^2$. In the hypothesis that Valo ES cells were not in good shape following a decrease of feeder cells concentration in the flask, then the avian cells are cultured for additional passages with the same feeder cells concentration before to pursue the feeder cells depletion.

The serum depletion were performed after the growth factor and the feeder cells depletion. At the beginning of serum depletion, the culture medium were composed of basal commercial medium DMEM-HamF12 supplemented with 10% fetal calf serum and with 1% non-essential amino acids, with 1% of mixture of vitamins of commercial origin, with sodium pyruvate at a final concentration of 1 mM, with beta-mercaptoethanol at a final concentration of 0.2 mM, glutamine at a final concentration of 2.9 mM. The chicken Valo cells were adapted to the growth in a serum free medium culture in a two steps process: first, the chicken Valo cells were rapidly adapted to a culture medium composed of commercial serum free medium (SFM), preferably ExCell 60947 (SAFC Biosciences) supplemented with 10% fetal calf serum and with 1% non-essential amino acids, with 1% of mixture of vitamins of commercial origin, with sodium pyruvate at a final concentration of 1 mM, with beta-mercaptoethanol at a final concentration of 0.2 mM, glutamine at a final concentration of 2.9 mM. Once this rapid adaptation to a new medium (DMEM-HamF12 to Excell 60947) was performed, a second step is performed consisting of a slow adaptation to decreasing concentration of animal serum in the SFM medium were initiated. Serum depletion was performed by a progressive decreasing starting from 10% serum, then 7.5%, then 5%, then 2.5%, then 1.25%, then 0.75% of serum concentration in SFM cell culture medium to finally reach 0% serum in SFM cell culture medium. Serum depletion started at passage 103 and ended at passage 135.

At the end of the process of deprivation of serum when the remaining concentration of serum in SFM medium was either 0.75% or 0%, the adaptation of anchorage-dependent EBv13 cells to suspension culture started. Among the several attempts performed to isolate anchorage-independent EBv13 isolates, 62.5% of the attempts were successful and allow to get different isolates of suspension EBv13 cells. One isolate of EBv13 cells were selected according to the population doubling time (around 18 h), the optimal cell concentration into flask culture (around 4 million cell/ml), the cell viability, the cell culture homogeneity (presence and size of cells clumps) and the easiness to manipulate the cells (FIG. 1).

At the end of serum depletion, anchorage dependent chicken Valo cells, named EBv13 were able to grow in absence of grow factors, in absence of feeder cells, in serum free medium. EBv13 Cells were then adapted to growth at 37° C., by progressively decreasing cell culture temperature of 0.5° C./day.

Example 2

Chicken EB Line 0 Cell Line from SPF Chicken Strain ELL-0

2.1—Raw Material
Eggs:

Chicken Specific Pathogen Free (SPF) strain called ELL-0 (East Lansing Line 0) was provided by the Avian Disease and Oncology Laboratory (USDA-ARS-MWA, USA). Those SPF chicken eggs, are produced from a flock tested intensively to various poultry pathogens. Disease tested include: *Salmonella pullorum, Salmonella gallinarum, mycoplasma gallisepticum, mycoplasma synoviae*, Avian Leukosis virus A-D and J, Marek's disease virus, Reticuloendotheliosis virus, Avian adenovirus, Infectious bronchitis, Infectious bursal disease, Avian Influenza, Newcastle disease, Avian encephalomyelitis and Avian Reovirus. Line 0 chicken eggs were only submitted to a desinfection with the decontaminant to avoid any risk of contamination linked to the manipulation of eggs during transportation.

Feeder Cells

In the first step of the process of establishment of EB Line 0, cells from murine origin (STO cells) were used as feeder layer to maintain the pluripotency of chicken stem cells. Those feeder cells are mitotically inactivated by gamma irradiation (45 to 55 Grays) before seeding on plastic. This dose of irradiation is a sub-lethal dose that induces a definitive arrest of the cell cycle but still permits the production of growth factors and extracellular matrix, necessary for the promotion of the cell growth of non differentiated cells.

The STO cell line was derived by A. Bernstein, Ontario Cancer Institute, Toronto, Canada from a continuous line of SIM (Sandos Inbred Mice) mouse embryonic fibroblasts and it was supplied by the American Type Culture Collection (ATCC) (STO Product number: CRL-1503, Batch number 1198713). Fresh feeder layers were prepared twice a week. Exponentially cells were dissociated and counted. A part of cells were seeded for maintenance of viable cultures and another part was irradiated. For irradiation, we prepared a cell suspension at $10 \times 10^6$ cells/mL in tubes. Cells were exposed to a 45 to 55 grey dose and were seeded on plastic. After seeding, dishes or plates coated with inactivated feeder cells were used during a maximum of 5 days.

Media
DMEM-HamF12 (Cambrex, Cat no BE04-687)
Medium GTM-3 (Sigma, Cat no G9916)

Medium EX-CELL™ 66522, 65788 and 66444 (SAFC, customized medium)

Additives
  Glutamine (Cambrex, Cat no BE17-605E)
  Pencillin/streptomycin (Cambrex, Cat no BE17-602E))
  Non essential Amino Acids (Cambrex, Cat no BE13-114E)
  Sodium pyruvate (Cambrex, Cat n'BE13-115)
  Vitamines (Cambrex, Cat no 13-607C)
  Beta Mercapto Ethanol (Sigma, Cat no M7522)
  Yeastolate (SAFC, Cat no 58902C)

Buffer and Fixators
  PBS 1× (Cambrex, Cat no BE17-516F)

Cryoprotective Agent
  Dimethyl Sulfoxyde (DMSO) (Sigma, Cat no D2650))

Factors
  Six different recombinant factors were used:
  Recombinant Human Ciliary Neurotrophic Factor (CNTF) (Peprotech Inc, Cat no 450-13)
  Recombinant Human Insulin Like Factor I (IGF1) (Peprotech Inc, Cat no 100-11)
  Recombinant Human Interleukin 6 (IL6) (Peprotech Inc, Cat no 200-06)
  Recombinant Human soluble Interleukin 6 receptor (sIL6r) (Peprotech Inc, Cat no 200-06 R)
  Recombinant Human Stem Cell Factor (SCF) (Peprotech Inc, Cat no 300-07)
  Recombinant Human basic Fibroblast Growth Factor (bFGF) (Peprotech Inc, Cat no 100-18B)

All those factors, excepted IL6r, are produced in *E. Coli* bacteria. Soluble IL6r is expressed in transfected HEK293 cells.

Fetal Bovine Serum
  Non Irradiated Fetal Bovin Serum (FBS) (SAFC, Cat No 12003)

The non irradiated serum used in the program was collected and produced in Australia. Animals used for collection were USDA inspected and acceptable for slaughter. It was added in the medium during avian stem cells culture. This batch was not submitted to irradiation to avoid the destruction of critical proteins or components identified as essential for the maintenance of stem cells in culture.

Irradiated Serum (JRH, Cat No 12007)

The irradiated batch used in this program was collected in Australia. This irradiated batch was added as supplement in the DMEM medium used for the culture of STO or FED cells (feeder cells). Those cells do not require as stem cells a specific quality of serum for growth and maintenance in culture. To minimize high concentration of serum in the medium we have adapted the STO cells to grow in presence of 4% of FBS only.

Dissociating Agents:
  Trypzean ((Sigma, Cat No T3449)

2.2—Process of Establishment of the Line 0 Cell Line

Embryos from 13 eggs from Line 0 chicken were collected according to the process described in Example 1.2. Then, the Line 0 embryos were placed in a tube containing PBS 1×. Embryos were then mechanically dissociated and inoculated on a layer of feeder STO cells into complete culture medium at 39° C. The feeder cells were seeded in dishes at around $2.7 \times 10^4$ cell/cm$^2$.

The complete culture medium is composed of basal commercial medium DMEM-Ham F12 supplemented with 10% fetal calf serum, with IGF1, CNTF, bFGF, IL6, IL6r and SCF at a final concentration of 1 ng/ml, and with 1% non-essential amino acids, with 1% of mixture of vitamins of commercial origin, with sodium pyruvate at a final concentration of 1 mM, with beta-mercapto-ethanol at a final concentration of 0.2 mM, glutamine at a final concentration of 2.9 mM, with yeastolate 1× and with an initial mixture of antibiotics containing penicillin at a final concentration of 100 U/ml and streptomycin at a final concentration of 100 µg/ml. After 7 passages, the mixture of antibiotics is no longer added to the medium.

When the avian ES cells from chicken Line 0 embryos are transferred from a culture dish to another, the seeding of culture dishes was performed with around between $7 \times 10^4$/cm$^2$ to $8 \times 10^4$/cm$^2$ of avian ES cells in the complete culture medium. Preferably, the seeding is made with around $7.3 \times 10^4$/cm$^2$ ($4 \times 10^6$ cells/55 cm$^2$ or $4 \times 10^6$ cells/100 mm dish). The avian cells, preferably the avian embryonic cells of step a) are cultured during several passages in the complete medium supplemented with 10 or 15% of FBS. At passage 7, the complete medium was depleted in growth factors bFGF, IL6, IL6r and SCF. The depletion was made directly in one step, from one passage to another. The embryonic stem cells, preferably the avian embryonic cells, were cultured during several passages in the complete medium without those 4 growth factors. At passage 12, the 2 last factors IGF1 and CNTF were removed from the medium and cells were amplified without factor.

To promote cell growth 3 base medium were used successively: DMEM Ham F12 from passage 1 to passage 18, Exell GTM-3 from passage 18 to passage 26 and a mixture of Excell 66788 and Excell 66522 after passage 26.

After passage 30, depletion of feeder cells was performed by a progressive decreasing of feeder cells concentration over several passages following the step by step process previously described. During this phase of feeder deprivation, some cells able to grow in suspension were isolated using Excell 66444 as growth medium and serum deprivation was initiated (FIG. 1B).

Example 3

Duck EBx Cell Line EB66

3.1—Raw Material

Duck Eggs

Duck eggs from Peking strains GL30 were obtained from GRIMAUD FRERES SELECTION (La Corbière, Roussay France). The parent ducks were vaccinated against *Escherichia Coli* (Autogenous vaccine Coli 01 & 02), *Pasteurella multocida* (Landavax), Duck viral hepatitis (Hepatovax), *Erysipelothrix rhusiopathiae* (Ruvax), Avian metapneumovirus (Nemovac), *Salmonella typhimurium* & *Enteridis* (Autogenous vaccine), *Riemerella antipestifer* (Autovaccine *Riemerella*), Avian metapneumovirus (Nobilis RTV inactive) and *Erysipelothrix rhusiopathiae* (Ruvax). After receipt, fertilized Peking duck eggs were submitted to a disinfection in an hypochloryde bath followed by a decontamination with Fermacidal (Thermo) to avoid any risk of contamination linked to dusts attached on the shell.

Feeder Cells

In the first step of the process, cells from murine origin (STO cells) were used as feeder layer to maintain the pluripotency of duck stem cells. Those feeder cells are mitotically inactivated by gamma irradiation (45 to 55 Grays) before seeding on plastic. This dose of irradiation is a sub-lethal dose that induces a definitive arrest of the cell cycle but still permits the production of growth factors and extracellular matrix, necessary for the promotion of the cell growth of non differentiated cells. The STO cell line was derived by A. Bernstein, Ontario Cancer Institute, Toronto, Canada from a continuous line of SIM (Sandos Inbred Mice) mouse embryonic fibroblasts and it was supplied by the American Type Culture Collection (ATCC) (STO Product number: CRL-1503, Batch number 1198713). Fresh feeder layers were prepared twice a week. Exponentially cells were dissociated and counted. A part of cells were seeded for maintenance of viable cultures and another part was irradiated. For irradiation, we prepared a cell suspension at $10\times10^6$ cells/mL in tubes. Cells were exposed to a 45 to 55 grey dose and were seeded on plastic. After seeding, dishes or plates coated with inactivated feeder cells were used during a maximum of 5 days.

Medium
  Medium EX-CELL™ 65788, 65319, 63066 and 66444 (SAFC, customized medium)
  Medium GTM-3 (Sigma, Cat no G9916)
  DMEM-HamF12 (Cambrex, Cat no BE04-687)
  DMEM (Cambrex, Cat no BE 12-614F)
Additives
  Glutamine (Cambrex, Cat no BE17-605E)
  Pencillin/streptomycin (Cambrex, Cat no BE17-602E))
  Non essential Amino Acids (Cambrex, Cat no BE13-114E)
  Sodium pyruvate (Cambrex, Cat no BE13-115)
  Vitamines (Cambrex, Cat no 13-607C)
  Beta Mercapto Ethanol (Sigma, Cat no M7522)
  Yeastolate (SAFC, Cat no 58902C)
Buffer and Fixators
  PBS 1× (Cambrex, Cat no BE17-516F)
Cryoprotective Agent
  Dimethyl Sulfoxyde (DMSO) (Sigma, Cat no D2650)
Factors
  Two different recombinant factors were used:
  Recombinant Human Ciliary Neurotrophic Factor (CNTF) (Peprotech Inc, Cat no 450-13)
  Recombinant Human Insulin Like Factor I (IGF1) (Peprotech Inc, Cat no 100-11)
  Those 2 factors are produced in *E. Coli* bacteria.
Fetal Bovine Serum
Non irradiated Fetal Bovin Serum (FBS) (JRH, Cat no 12003)

The non irradiated serum used in the program was collected and produced in Australia. Animals used for collection were USDA inspected and acceptable for slaughter. It was added in the medium during avian stem cells culture. This batch was not submitted to irradiation to avoid the destruction of critical proteins or components identified as essential for the maintenance of stem cells in culture.

Irradiated Serum (JRH, Cat No 12107)

The irradiated batch used in this program was collected in United States. This irradiated batch was added as supplement in the DMEM medium used for the culture of STO cells (feeder cells). Those cells do not require as stem cells a specific quality of serum for growth and maintenance in culture. To minimize high concentration of serum in the medium we have adapted the STO cells to grow in presence of 4% of FBS only.

Dissociating Agents:
  Pronase (Roche, Cat No 165 921)
  Pronase is a recombinant protease manufactured by Roche Diagnostics, Germany, used for the dissociation of adherent avian stem cells.
  Trypsine EDTA (Cambrex, Cat No BE17-161E)
  Trypsine is used for the dissociation of STO cells and at late passages for the dissociation of avian cells adapted to Serum Free Medium. This enzyme of porcine origin is manufactured aseptically according to cGMP referential conditions by a validated sterile filtration method and tested according to current E.P. The raw material, irradiated prior to formulation, is tested for porcine parvovirus in strict compliance with 9/CFR 113.53.

Trypzean (Sigma, Cat No T3449)
  Trypzean solution is formulated with a recombinant bovine trypsin, expressed in corn and manufactured by Sigma Aldrich utilizing ProdiGene's proprietary transgenic plant protein expression system. This product is optimized for cell dissociation in both serum free and serum-supplemented adherent cell cultures.

Non Enzymatic Cell Dissociation Solution (Sigma, Cat No C5914)
  This agent of dissociation is a ready to use formulation used to gently detach cells from the growing surface of the culture vessel. The formula contains no protein, and allows dislodging of cells without use of enzymes. Cellular proteins are preserved making possible immunochemical studies that are dependent upon the recognition of cell surface proteins. This enzyme was used to detach cell before FACS analysis of biological markers like EMA-1 (Epithelial Membrane Antigen 1) and SSEA1 (Stage Specific Embryonic antigen-1).

3.2—Process of Establishment of Duck EBx Cell Line EB66

Around 360 Fertilized duck eggs were opened, the yolk were separated from the albumen during the opening. The embryos were removed from the yolk with the aid of a small absorbent filter paper (Whatmann 3M paper), cut out beforehand in the form of a perforated ring with the aid of a punch. The diameter of the perforation is about 5 mm. These small rings were sterilized using dry heat for about 30 minutes in an oven. In practice, during the step of embryo collection, a small paper ring is deposited on the surface of the yolk and centered on the embryo which is thus surrounded by the paper ring. The latter is then cut out with the aid of small pairs of scissors and the whole removed is placed in a Petri dish, filled with PBS. The embryo thus carried away by the ring were cleaned of the excess yolk in the medium and the embryonic disk, thus free of the excess vitellin, were collected with a Pasteur pipette.

The duck embryos were placed in 50 mL tubes containing PBS 1×. The duck embryos were then mechanically dissociated, washed with PBS, and seeded on an inactivated layer of feeder STO cells into complete culture medium at 39° C., 7.5% $CO_2$. The feeder cells were seeded in 6 well plates or dishes at around $2.7\times10^4$ cell/cm$^2$. The complete culture medium is composed of serum free medium DMEM-Ham F12 supplemented with 10% fetal bovine serum, with IGF1, CNTF, at a final concentration of 1 ng/ml, and with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM, penicillin at a final concentration of 100 U/ml, streptomycin at a final concentration of 100 µg/ml and yeastolate 1×. Rapidly at the passage 4, the mixture of antibiotics is no longer added to the medium.

The duck ES cells were cultured in the DMEM-Ham F12 medium up to passage 4. After passage 4, the base medium is modified and DMEM-Ham F12 complete medium is replaced by the SFM GTM-3 medium supplemented with 10% fetal bovine serum, with IGF1, CNTF, at a final concentration of 1 ng/ml, with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM and yeastolate 1×. The duck ES cells were further cultured during 14 passages in this new medium of culture, then growth factors deprivation was performed at passage 18. IGF1 and CNTF were simultaneously removed from the medium, thus from passage 19 to passage 24, the medium of culture was GTM-3 medium supplemented with 10% FBS, with 1% non-essential amino acids, with 1% of mixture of vitamins of commercial origin, with sodium pyruvate at a final concentration of 0.1 mM, with beta-mercaptoethanol at a final concentration of 0.5 mM, glutamine at a final concentration of 2.1 mM and yeastolate 1×.

When the duck ES cells from Peking duck embryos are passaged from a culture dish to another, the seeding of culture dish was performed with around between $7 \times 10^4/\text{cm}^2$ to $12 \times 10^4/\text{cm}^2$ of duck ES cells in the complete culture medium.

Then, after passage 24, depletion of feeder cells were performed by a progressive decrease of feeder cells concentration over several passages. The dishes were originally seeded with around $2.7 \times 10^4$ feeder cells/cm², then around $1.8 \times 10^4$ feeder cells/cm² between passage 25 and 31, then around $1.4 \times 10^4$ cells/cm² between passage 32 and 35, then around $1 \times 10^4$ feeder cells/cm² between passage 36 and 41, then around $0.7 \times 10^4$ feeder cells/cm² between passage 42 and 44, and finally from passage 45 dishes were seeded only with avian cells and without feeder cells. At the end of the feeder depletion, the dishes are seeded with $9 \times 10^4$ avian cells/cm² to $12.7 \times 10^4$ avian cells/cm². The depletion of feeder cells started at passage 25 and ended at passage 45. During the depletion of feeder cells, the duck ES cells are seeded in culture dishes at a higher concentration than in step a), about around $9 \times 10^4$ cell/cm² to $12.7 \times 10^4$ cell/cm².

After several passages without feeder cells, growth parameters (Population Doubling Time (PDT) and Density) are studied to confirm cell stability and robustness and to initiate the deprivation of amino acids, vitamins, beta mercaptoethanol, sodium pyruvate and yeastolate. Cells are considered as enough robust to be submitted to such deprivation if, PDT is lower than around 40 hours and cell density higher than around $26 \times 10^4$ cells/cm².

In the case of the present duck EBx® cells development, named EB66, deprivation of vitamins, sodium pyruvate, non essential amino acids and beta mercaptoethanol were initiated at passage 52. All those additives were removed simultaneously from the medium. Thus, between passage 52 and passage 59, the medium of culture is SFM GTM-3 supplemented with glutamine, yeastolate and FBS. Following a short period of adaptation to the new conditions of culture, temperature decreasing was initiated. This decrease was performed progressively between passage 60 and passage 67. After passage 67 cells were able to grow at 37° C. After passage 67, the base medium GTM-3 was replaced by a new SFM base medium called Excell 65788. So, after passage 67 the culture medium was Excell 65788 supplemented with 10% FBS, 2.5 mM glutamine and 1× yeastolate. At passage 80, $4 \times 10^6$ cells were transferred in a Ultra Low Attachment (ULA) dish maintained under constant agitation to initiate anchorage-independent cells growth. To promote the growth as suspension, the base medium was modified and percentage of serum was decreased from 10% to 5% for the seeding in the ULA dish. Thus from passage 80 to passage 85 the medium of culture was SFM GTM-3 supplemented with 5% FBS, 2.5 mM glutamine and 1× yeastolate. Slow decrease of FBS was initiated on EB66 cell suspension after passage 85. Serum depletion was performed by a progressive decreasing starting from 2.5% serum, then 1.5% of serum concentration in SFM cell culture medium to finally reach 0% serum in SFM cell culture medium. Serum depletion started at passage 86 and ended at passage 94. At the end of serum depletion, anchorage independent dEB66 cells were able to grow at 37° C. in absence of grow factors, in absence of feeder cells, in serum free medium.

After the obtaining of EB66 duck cells that are able to grow at 37° C. in the SFM GTM-3 supplemented by 2.5 mM glutamine, some further adaptation to SFM media were made by dilution or progressive adaptation in new SFM formulations as Excell 63066, Excell 66444, Excell CHO ACF for example.

The subcloning of suspension duck EB66 cell could also realized in presence or absence of yeastolate Example 4

Duck EBx Cell Line EB26

4.1—Raw Material
Duck Eggs, Feeder Cells, Additives, Buffers and Fixators, Cryopreservative Agents, Fetal Calf Serum & Dissociating Agents (Idem as Example 3).
Duck eggs from Peking strains GL30 were used.
Medium
    Medium EX-CELL 65319, 63066 and 66444 (SAFC, customized medium)
    Medium GTM-3 (Sigma, Cat no G9916)
    DMEM (Cambrex, Cat no BE 12-614F)
Factors
    Six different recombinant factors were used:
    Recombinant Human Ciliary Neurotrophic Factor (CNTF) (Peprotech Inc, Cat no 450-13)
    Recombinant Human Insulin Like Factor I (IGF1) (Peprotech Inc, Cat no 100-11)
    Recombinant Human Interleukin 6 (IL6) (Peprotech Inc, Cat no 200-06)
    Recombinant Human soluble Interleukin 6 receptor (sIL6r) (Peprotech Inc, Cat no 200-06 R)
    Recombinant Human Stem Cell Factor (SCF) (Peprotech Inc, Cat no 300-07)
    Recombinant Human basic Fibroblast Growth Factor (bFGF) (Peprotech Inc, Cat no 100-18B)
All those factors, excepted IL6r, are produced in *E. Coli* bacteria. Soluble IL6r is expressed in transfected HEK293 cells.

4.2—Process of Establishment of Duck EBx Cell Line EB26
The duck embryos were collected as previously described with EB66. The duck embryos were placed in 50 mL tubes containing PBS 1×. The duck embryos were then mechanically dissociated, washed in PBS, and seeded on an inactivated layer of feeder STO cells into complete culture medium at 39° C., 7.5% $CO_2$. The feeder cells were seeded in 6 well plates or dishes at around $2.7 \times 10^4$ cell/cm². The complete culture medium is composed of serum free medium GTM-3 supplemented with 5% fetal bovine serum, with IGF1, CNTF, II-6, II-6R, SCF and FGF at a final concentration of 1 ng/ml, and with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM, penicillin at a final concentration of 100 U/ml, streptomycin at a final concentration of 100 µg/ml and yeastolate 1×. Rapidly after the first passages of the cells, the mixture of antibiotics is no longer added to the medium. The expression rapidly is understood to mean after the first 3 to 9 passages in general. The duck ES cells were cultured in the complete medium up to passage 9. After passage 9, the complete medium is partially depleted in factors. Thus, between passage 10 and 13, SCF, IL6, IL6r and bFGF were removed for the medium and only recombinant IGF1 and CNTF were maintained at a concentration of 1 ng/mL. A simultaneous decease of concentration of IGF1 and CNTF is secondly performed between passage 13 and 16 to finally obtain cells able to grow without recombinant factors at passage 17. The factor depletion were made by a progressive adaptation to lower concentrations of factors. When the duck ES cells from Pekin duck embryos were passaged from a culture dish to another, the seeding of culture dish was performed with around between $7\times10^4/cm^2$ to $12\times10^4/cm^2$ of duck ES cells in the complete culture medium. Preferably, the seeding is made with around $7.3\times10^4/cm^2$ ($4\times10^6$ cells/55 $cm^2$ or $4\times10^6$ cells/100 mm dish). After depletion of recombinant factors, a decrease of yeastolate were performed at passage 23 reaching the final concentration at 0.5×. Then, after passage 31, depletion of feeder cells were performed by a progressive decrease of feeder cells concentration over several passages. The dishes were originally seeded with around $2.7\times10^4$ feeder cells/$cm^2$, then around $1.8\times10^4$ feeder cells/$cm^2$ between passage 32 and 38, then around $1.4\times10^4$ cells/$cm^2$ between passage 39 and 44, then around $1\times10^4$ feeder cells/$cm^2$ between passage 45 and 47, then around $0.7\times10^4$ feeder cells/$cm^2$ between passage 48 and 50, and finally from passage 51 dishes were seeded only with avian cells and without feeder cells. At the end of the feeder depletion, the dishes are seeded with $9\times10^4$ avian cells/$cm^2$ to $12.7\times10^4$ avian cells/$cm^2$. The depletion of feeder cells started at passage 32 and ended at passage 51. During the depletion of feeder cells, the duck ES cells are seeded in culture dishes at a higher concentration than in step a), about around $9\times10^4$ cell/$cm^2$ to $12.7\times10^4$ cell/$cm^2$. After several passages without feeder cells, growth parameters (Population Doubling Time (PDT) and Density) were studied to confirm cell stability and robustness and to initiate the cell growth as suspension. Cells are considered as enough robust to be submitted to a culture in suspension if, PDT is lower than around 40 hours and cell density higher than around $26\times10^4$ cells/$cm^2$. Moreover, cells morphology should be: round, refringent, very small and the cells shall not attached to the plastic dish too much.

In the case of the EB26 cell development, culture in suspension were initiated at passage 53. $7\times10^6$ cells were transferred in a Ultra Low attachment dish and maintained under constant agitation at around 50 to 70 rpm. For the next passages, cells were seeded in T175 flasks (Sarsted, ref 831812502) at a concentration comprise between 0.4 to $0.5\times 10^6$ cells/mL. Following a short period of adaptation to the new conditions of culture, cells PDT decreased from around 160 H to 40 hours. Regarding this good evolution, at passage 59, a new set of deprivation was performed. Thus vitamins, sodium pyruvate, beta-mercaptoethanol and non essential amino acids were removed. Thus after passage 59, the culture medium was supplemented with 5% FBS, 0.5× yeastolate and 2.5 mM glutamine only. The serum depletion is performed on cell suspensions already depleted in growth factor, feeder cells, vitamins, non essential amino acids, sodium pyruvate and beta-mercaptoethanol. Serum depletion was performed by a progressive decreasing starting from 5% serum, then 2.5%, then 1.5%, of serum concentration in SFM cell culture medium to finally reach 0% serum in SFM cell culture medium. Serum depletion started at passage 61 and ended at passage 79. At the end of serum depletion, anchorage independent duck EB26 cells were able to grow at 39° C. in absence of grow factors, in absence of feeder cells, in serum free medium. EB26 cells were then adapted to growth in absence of 0.5× yeastolate at 37° C., by decreasing cell culture temperature at passage 80.

After the obtaining of EB26 cells that are able to grow at 37° C. in the SFM GTM-3 supplemented by 2.5 mM glutamine, some further adaptation were made by dilution or progressive adaptation on new SFM formulations as Excell 63066, Excell 66444, Excell CHO ACF. The subcloning of suspension duck EB26 cell could also realized in presence or absence of yeastolate.

Example 5

Duck EBx cell line EB24

5.1—Raw Material
Duck Eggs, Feeder Cells, Additives, Buffers and Fixators, Cryopreservative Agents, Fetal Calf Serum & Dissociating Agents (Idem as Example 3).
Duck eggs from Peking strains GL30 were used.
Medium
  Medium EX-CELL™ 65319, 63066 and 66444 (SAFC, customized medium)
  Medium GTM-3 (Sigma, Cat no G9916)
  DMEM F12 (Cambrex, Cat no BE04-687)
  DMEM (Cambrex, Cat no BE 12-614F)
Factors
  Six different recombinant factors were used:
  Recombinant Human Ciliary Neurotrophic Factor (CNTF) (Peprotech Inc, Cat no 450-13)
  Recombinant Human Insulin Like Factor I (IGF1) (Peprotech Inc, Cat no 100-11)
  Recombinant Human Interleukin 6 (IL6) (Peprotech Inc, Cat no 200-06)
  Recombinant Human soluble Interleukin 6 receptor (sIL6r) (Peprotech Inc, Cat no 200-06 R)
  Recombinant Human Stem Cell Factor (SCF) (Peprotech Inc, Cat no 300-07)
  Recombinant Human basic Fibroblast Growth Factor (bFGF) (Peprotech Inc, Cat no 100-18B)
  All those factors, excepted IL6r, are produced in *E. Coli* bacteria. Soluble IL6r is expressed in transfected HEK293 cells.
5.2—Process of Establishment of Duck EBx® Cell Line EB24

The duck embryos were collected as previously described with EB66. The duck embryos were placed in 50 mL tubes containing PBS 1×. The duck embryos are then mechanically dissociated and seeded on an inactivated layer of feeder STO cells into complete culture medium at 39° C., 7.5% $CO_2$. The feeder cells were seeded in 6 well plates or dishes at around $2.7\times10^4$ cell/$cm^2$. The complete culture medium is composed of serum free medium DMEM-Ham F12 supplemented with 10% fetal bovine serum, with IGF1, CNTF, Il-6, Il-6R, SCF and FGF at a final concentration of 1 ng/ml, and with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM, penicillin at a final concentration of 100 U/ml, streptomycin at a final concentration of 100 µg/ml and 1× yeastolate. Rapidly after the first passages of the cells, the mixture of antibiotics is no longer added to the medium. The expression rapidly is understood to mean after the first 3 to 9 passages in general.

The duck ES cells are cultured in the DMEM-Ham F12 complete medium up to passage 7. After passage 7, the base medium is modified and DMEM-Ham F12 complete medium is replaced by the GTM-3 complete medium supplemented with 10% fetal bovine serum, with IGF1, CNTF, Il-6, Il-6R, SCF and FGF at a final concentration of 1 ng/ml, with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM, penicillin at a final concentration of 100 U/ml, streptomycin at a final concentration of 100 µg/ml and yeastolate 1×. Thus, at passage 11, the serum concentration is decreased at 5% and SCF, IL6, IL6r and bFGF are removed for the medium. So, from passage 11, the medium is composed of 5% FBS, with IGF1 and CNTF at a final concentration of 1 ng/mL with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM, penicillin at a final concentration of 100 U/ml, streptomycin at a final concentration of 100 µg/ml and yeastolate 1×. A simultaneous withdrawal of IGF1 and CNTF is performed at passage 22. No recombinant factors are present in the GTM-3 culture medium after passage 22. Duck cells were maintained in a such medium between passage 23 and passage 28. When the duck ES cells from Pekin duck embryos are passaged from a culture dish to another, the seeding of culture dish was performed with around between $7 \times 10^4/cm^2$ to $12 \times 10^4/cm^2$ of duck ES cells in the complete culture medium. Preferably, the seeding is made with around $7.3 \times 10^4/cm^2$ ($4 \times 10^6$ cells/55 $cm^2$ or $4 \times 10^6$ cells/100 mm dish). Then, after passage 28, depletion of feeder cells is performed by a progressive decrease of feeder cells concentration over several passages. The dishes were originally seeded with around $2.7 \times 10^4$ feeder cells/$cm^2$, then around $1.8 \times 10^4$ feeder cells/$cm^2$ between passage 29 and 33, then around $1.4 \times 10^4$ cells/$cm^2$ between passage 34 and 37, then around $1 \times 10^4$ feeder cells/$cm^2$ between passage 38 and 42, then around $0.7 \times 10^4$ feeder cells/$cm^2$ between passage 43 and 46, and finally from passage 47 dishes were seeded only with avian cells and without feeder cells. At the end of the feeder depletion, the dishes are seeded with $9 \times 10^4$ avian cells/$cm^2$ to $12.7 \times 10^4$ avian cells/$cm^2$. The depletion of feeder cells started at passage 29 and ended at passage 47. During the depletion of feeder cells, the duck ES cells are seeded in culture dishes at a higher concentration than in step a), about around $9 \times 10^4$ cell/$cm^2$ to $12.7 \times 10^4$ cell/$cm^2$. After several passages without feeder cells, growth parameters (Population Doubling Time (PDT) and Density) were studied to confirm cell stability and robustness and to initiate the cell growth as suspension. Cells are considered as enough robust to be submitted to a culture in suspension if, PDT is lower than around 40 hours and cell density higher than around $26 \times 10^4$ cells/$cm^2$. Moreover, cells morphology should be: round, refringent, very small and the cells shall not attached to the plastic dish too much. In the case of the EB24 cell development, culture in suspension is initiated at passage 48. $8 \times 10^6$ cells were transferred in a Ultra Low attachment dish and maintained under constant agitation at around 50 to 70 rpm. For the next passages, cells were seeded in T175 flasks (Sarsted, ref 831812502) at a concentration comprise between 0.4 to $0.5 \times 10^6$ cells/mL. Following a short period of adaptation to the new conditions of culture, cell PDT decreased from around 248 H to 128 hours and the next step of deprivation is then performed. Thus at passage 52, vitamines, non essential amino acids, sodium pyruvate and beta mercaptethanol are removed. Regarding the good evolution of the PDT reaching 44 hours, at passage 56, from passage 57, the serum deprivation was initiated. Thus from passage 57, the culture medium GTM-3 was supplemented with 5% FBS, 1× yeastolate and 2.5 mM glutamine only. The serum depletion is performed on cell suspensions already depleted in growth factors, feeder cells, vitamins, non essential amino acids, sodium pyruvate and beta-mercaptoethanol. Serum depletion was performed by a progressive decreasing starting from 5% serum, then 2.5%, then 2%, then 1.5% of serum concentration in SFM cell culture medium to finally reach 0% serum in SFM cell culture medium. Serum depletion started at passage 57 and ended at passage 77. During this serum depletion, adaptation to growth at 37° C. was also performed. Thus at passage 65, cells growing in the culture medium supplemented with 2.5% FBS were transferred at 37° C. avoiding a progressive temperature shift. At the end of serum depletion, anchorage independent duck EB24 cells were able to grow at 37° C. in absence of grow factors, in absence of feeder cells, in serum free medium.

After the obtaining of duck EB24 cells able to grow at 37° C. in the SFM GTM-3 supplemented by 2.5 mM glutamine, some further adaptation were made by dilution or progressive adaptation in new SFM formulations as Excell 63066, Excell 66444, Excell CHO ACF. The subcloning of suspension duck EB24 were performed, an duck EB24-12 subclone were selected because of its good performance to efficiently replicate viruses.

Example 6

SPF Duck Muscovy EBx Cell Line 6.1—Raw Material

Duck Eggs:

Duck SPF eggs from Muscovy strains were obtained from Le Couvoir de Cerveloup (France). Those SPF duck eggs, are produced from a flock tested intensively to various poultry pathogens. Disease tested include: *Salmonella gallinarum-pullorum, Mycoplasma synoviae, Mycoplasma meleagridis, Mycoplasma galliepticum*, Marek's disease virus, Avian Influenza, Type 2 Paramyxovirus, Type 3 Paramyxovirus, Newcastle disease, Type 3 Adenovirus (EDS), Gumboro disease, Avian reovirus, Reticuloendotheliosis virus, Avian encephalomyelitis, infectious rhinotracheitis virus and Chlamydiosis. Muscovy duck eggs were only submitted to a disinfection with the decontaminant to avoid any risk of contamination linked to the manipulation of eggs during the transport.

Feeder Cells (See Previous Examples)

Media

Medium EX-CELL™ 66444 (SAFC, customized medium)

Medium GTM-3 (Sigma, Cat no G9916)

DMEM-HamF12 (Cambrex, Cat no BE04-687)

Additives

Glutamine (Cambrex, Cat no BE17-605E)

Pencillin/streptomycin (Cambrex, Cat no BE17-602E))

Non essential Amino Acids (Cambrex, Cat no BE13-114E)

Sodium pyruvate (Cambrex, Cat no BE13-115)

Vitamines (Cambrex, Cat no 13-607C)

Beta Mercapto Ethanol (Sigma, Cat no M7522)

Yeastolate (SAFC, Cat no 58902C)

Buffer and Fixators:

PBS 1× (Cambrex, Cat no BE17-516F)

Cryoprotective Agent

Dimethyl Sulfoxyde (DMSO) (Sigma, Cat no D2650)

Factors

Two different recombinant factors were used:

Recombinant Human Ciliary Neurotrophic Factor (CNTF) (Peprotech Inc, Cat no 450-13)

Recombinant Human Insulin Like Factor I (IGF1) (Pepro-
tech Inc, Cat no 100-11)

Those 2 factors are produced in *E. Coli* bacteria.

Fetal Bovine Serum

Non Irradiated Fetal Bovin Serum (FBS) (JRH, Cat No 12003)

The non irradiated serum used in the program was collected and produced in Australia. Animals used for collection were USDA inspected and acceptable for slaughter. It was added in the medium during avian stem cells culture. This batch was not submitted to irradiation to avoid the destruction of critical proteins or components identified as essential for the maintenance of stem cells in culture.

Irradiated Serum (JRH, Cat No 12007)

The irradiated batch used in this program was collected in Australia. This irradiated batch was added as supplement in the DMEM medium used for the culture of STO cells (feeder cells). Those cells do not require as stem cells a specific quality of serum for growth and maintenance in culture. To minimize high concentration of serum in the medium we have adapted the STO cells to grow in presence of 4% of FBS only.

Dissociating Agents:

Pronase (Roche, Cat no 165 921)

Trypzean (Sigma, cat no T3449)

6.2—Process of Establishment of Muscovy Duck EBx Cell Line

Embryos from 20 fertilized SPF eggs from Muscovy ducks were collected according to the process described in Example 3. The duck embryos were placed in 50 mL tubes containing PBS 1×. The duck embryos were then mechanically dissociated, washed with PBS, and seeded in a well of a 12 well plate coated with an inactivated layer of feeder STO cells. Duck Embryonic cells were seeded into complete culture medium and transferred at 39° C., 7.5%5% $CO_2$. The feeder cells were seeded at around $2.7 \times 10^4$ cell/cm$^2$. The complete culture medium used is composed of DMEM-Ham F12 supplemented with 10% fetal bovine serum, with IGF1, CNTF, at a final concentration of 1 ng/ml, and with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM, penicillin at a final concentration of 100 U/ml, streptomycin at a final concentration of 100 µg/ml and yeastolate 1×. At passage 2, the DMEM-HamF12 base medium is replaced by GTM-3 base medium. The mixture of antibiotics is no longer added to the medium after passage 4.

The duck ES cells were cultured in the complete GTM-3 medium up to passage 8. After passage 8, concentration of IGF1 and CNTF are reduced to 0.5 ng/mL. The duck ES cells were further cultured during 2 passages in this new medium of culture, then growth factor deprivation was performed at passage 10. IGF1 and CNTF were simultaneously removed from the medium.

Thus from passage 10 to passage 37, the medium of culture was GTM-3 medium supplemented with 10% FBS, with 1% non-essential amino acids, with 1% of mixture of vitamins of commercial origin, with sodium pyruvate at a final concentration of 0.1 mM, with beta-mercapto-ethanol at a final concentration of 0.5 mM, glutamine at a final concentration of 2.1 mM and yeastolate 1×.

When the duck ES cells isolated from Muscovy duck embryos are passaged from a culture dish to another, the seeding was performed with around $12 \times 10^4$/cm$^2$ of duck ES cells in the culture medium. Some conditioned medium can be occasionally used for cell seeding to improve cell recovery post dissociation.

Then, after passage 37, depletion of feeder cells was performed by a progressive decreasing of feeder cells concentration over several passages following the step by step process previously described.

During this phase of feeder deprivation, some cells able to grow in suspension were isolated and adapted to grow without additives and serum (FIG. 4C). Anchorage-independent Muscovy duck EBx cells express ES cells markers, such as telomerase, SSEA-1 and EMEA-1 (data not shown).

Example 7

EBx Cell Lines Characterization 7.1—Chicken Valo EBv13 Cells Characterization 7.1.1—Telomerase Activity Telomerase detection is achieved by using the Telo TAGGG Telomerase PCR ELISA developed by Roche Applied Science (Telomeric Repeat Amplification Protocol (TRAP)—Cat. No. 11 854 666 910) according to the supplier protocol. The Telo TAGGG Telomerase PCR ELISA allows amplification of Telomerase-mediated elongation products combined with non radioactive detection following an ELISA protocol. The assay is valid if absorbance value of the negative control is less than or equal to $0.25\ A_{450nm}\text{-}A_{690nm}$ and if absorbance value of the positive control is higher than or equal to $1.5\ A_{450nm}\text{-}A_{690nm}$ when using $1 \times 10^3$ cell equivalents in the assay. Samples are regarded as telomerase positive if the difference in absorbance is higher than $0.2\ A_{450nm}\text{-}A_{690nm}$ units. Two controls were used: the negative control is murine fibroblasts (FED cells) and the positive controls are FGB8 cells (Embryonic Stem cells established by Vivalis from 129 SV mouse embryos) and chicken EB14-074 cells previously established in WO 03/076601.

Results obtained are summarized on the FIG. 2. EBv13 cells do express high level of telomerase. At passage p193 and 195, the telomerase activity is equivalent to the one of chicken EB14-074 cells.

7.1.2—ES Cells Biological Markers

Embryonic stem cells are characterized by the expression of biological markers expressed on the cell membrane. The expression of EMA-1 (Epithelial Membrane Antigen-1) and SSEA-1 (Stage Specific Embryonic Antigen-1) on EBv13 cells were evaluated by FACS analysis. After 10 minutes of fixation with PFA 4% (Para-formaldehyde), cell samples and controls are rinsed and pre-incubated with monoclonal antibodies specific of EMA-1 or SSEA-1. A second antibody conjugated to FITC is used for detection of cells expressing the 2 biological markers selected. Samples were analyzed by flow cytometry using a FACS (Flow Activated Cell Sorter) from Coulter.

FACS analysis was done on mouse fibroblasts cells (FED cells) as a negative control, murine ES FGB8 cells as a positive control, chicken EB14-074 cells as a positive control EBx cells and EBv13 cells. As expected FED cells do not express biological markers whereas FGB8 and EB14-074 cells present an important staining, respectively of, 60.13% and 78.7 for EMA-1 and 94.45% and 95% for SSEA-1 (data not shown). Chicken valo EBv13 cells population do not present any staining for EMA1 (2%) and a very light one for SSEA-1 (22%).

7.1.3—Karyotype

Karyotype analysis was performed to check the cell diploidy and the avian origin of EBv13 cells. Cells in the exponential phase of growth were harvested and treated 2 hours by colcemid (0.02 µg/mL). After washing and centrifugation, an hypotonic choc is performed on cells with KCl (0.56%) during 20 minutes. Subsequently, EBv13 cells were fixed in methanol/acetic acid (3/1) and stored overnight at −20° C. The day after, metaphasis were spotted on glass, stained by a wright/giemsa solution and observed under microscope. Several series of metaphases were observed confirming the chicken origin of EBv13 cells. No evidence of polyploidy is observed.

7.1.4—Influence of Cell Culture Medium Composition on the Clumps Size of EBv13 Cells The inventors have found that the concentration of Calcium and Magnesium in the serum-free medium used for the EBx cells culture and infection have an impact on the clumps size. FIG. 10 shows the decrease in clumps size when EBv13 cells are passed from a medium with a high to a low $Ca^{2+}$ and $Mg^{2+}$ concentration.

7.2—Duck Ebx Cell Lines Characterization 7.2.1—Duck EBx Cells Morphology

Transmission Electronic Microscopy analysis of dEBx® cells were performed by Dr. A Rivoire (Lyon, France). Duck EBx® cells display a typical embryonic stem cells morphology (i.e high nucleo-cytoplasmic ratio) that resemble the phenotype of murine embryonic stem cells and VIVALIS EB14 cells described in WO2006/108846. Duck EBx® cells are small round cells (diameter ~10 μm) with a large nucleus and nucleolus, with short pseudopodia extending from the plasma membrane (FIG. 4A, FIG. 4B and FIG. 4C). They are highly metabolic active with a ribosome and mitochondria rich cytoplasm. They contain numerous intracellular vacuoles, a very developed Golgi system and a granulous reticulum endoplasmic.

7.2.2—Telomerase Expression of Duck EBx® Cells

Telomerase expression during different stages of establishment of in duck EBx® cells was investigated by using Roche telomerase detection kit (Telomerase OCR ELISA). Telomerase is found to be highly expressed in adherent duck EBx® cells, as well as during feeder deprivation, during the process of adapting duck EBx® cells to suspension and during feeder deprivation. FIG. 5 shows that duck EB24 and EB26 express high level of telomerase, just like chicken EB14 cells. Duck EB66 also express high level of telomerase all along cell passages. This high telomerase activity is stable in EB66 cells after adaptation in different SFM (FIG. 15).

7.2.3—Duck EBx® Cells Display No Endogenous Reverse Transcriptase Activity

Endogenous reverse transcriptase expression was investigated by direct F-PERT analysis (Lovatt et al., 1999, J. Virol. Methods, 82:185-200) in Clean Cells (FRANCE). Duck EBx® cell lines, EB24 (data not shown), EB66 (data not shown), EB26 and EB51, display no endogenous Reverse Transcriptase (RT) activity (FIG. 6A). RT activity were detected in chicken EB14 cells culture as well as, to a lesser extend, in chicken Embryonic fibroblast derived from Specific Pathogen Free (SPF) chicken strain.

The presence of endogenous retroviral particles, either replicative or non-replicative, in the cell culture supernatant of duck and chicken EBx® cells were investigated by an ELISA assay detecting the avian leukosis major capsid antigen P27 (FIG. 6B). All Duck EBx® cell lines (EB26, EB51, EB24, EB66 . . . ), as well as chicken EBv13 do not secrete ALV p27 antigen. In the opposite, chicken EB14 cells do express ALV P27 antigen.

7.2.4—Duck EBx Cells do not Secrete Replicative Avian Leucosis Virus (ALV)

Co-cultivation assay of duck EBx cells with quail QT6 cell line, known to be sensitive to endogenous and exogenous ALVs, were performed to detect the presence of endogenous replicative duck viruses. FIG. 7A described the principle of QT6 co-culture. The presence of replicative virus is detected by an ELISA assay detecting the avian leucosis major capsid antigen P27. The assay demonstrates that none of duck EBx cells tested secrete replicative (i.e replication competent) ALV (FIG. 7B).

7.2.5—Duck EBx Cells Express Avian and Human Influenza Virus Receptors

The detection of receptors to avian (Siaα2-3Gal) and human (Siaα2-6Gal) influenza viruses on duck EBx cells were performed by fluorescent cell sorter analysis by using digoxygenin labelled lectins (Boehringer):

*Sambuca nigra* (SNA) agglutinin lectin specifically binds to Siaα2-6Gal;

*Maackia amurensis* (MAA) agglutinin lectin specifically binds to Siaα2-3Gal.

Chicken EB14 and duck EBx cells were washed in 10 mM HEPES, 150 mM NaCl pH7.5 and resuspended in the same buffer at a $5.10^6$ final concentration. Cells were incubated 30 min on ice, then for an additional 15 to 30 minutes in presence of SNA or MAA. Lectin treated cells were washed in 10 mM HEPES, 150 mM NaCl pH7.5, prior to incubation on ice during 15 to 30 minutes with FITC-labelled anti-digoxygenin antibody. Then cells are washed in NaCl 0.9% and FACS analyzed.

Chicken EB14 and duck EBx cells express cell surface receptors comprising oligosaccharides with Siaα2-6Gal and Siaα2-3Gal residues (FIG. 8).

7.2.6—Karyotype

Karyotype analysis was performed to check the cell diploidy and the avian origin of duck EB24 and EB66 cells. Cells in the exponential phase of growth were harvested and treated 3 to 6 hours by colcemid (0.6 mg/mL). After washing and centrifugation, an hypotonic choc is performed on cells with KCl (0.56%) during 20 minutes. Subsequently, duck EB24 and EB66 cells were fixed in methanol/acetic acid (3/1) and stored overnight at −20° C. The day after, metaphasis were spotted on glass, stained by a wright/giemsa solution and observed under microscope.

Several series of metaphases were observed confirming the duck origin of EBx cells. No evidence of polyploidy were observed. FIG. 16 shows diploid karyotype of duck EBx66 cells (FIG. 16).

Example 6

Poxvirus Replication in Chicken EBv13 Cell Line

Susceptibility of EBv13 cells to infection with poxvirus was investigated using a recombinant Modified Vaccinia Ankara (MVA) encoding a GFP gene (Green Fluorescent Protein).

The following protocol were used: Three days before infection, $0.4 \times 10^6$ EBv13 cells (passage 188)/mL are seeded in T175 flasks under 40 mL of SFM Excell 65319 (SAFC) supplemented with 4 mM Glutamine. The infection is performed at a multiplicity of infection of $10^{-2}$ TCID50/cell (MVA-GFP stock is at 10e9.7 TCID/ml). One hour post infection, 60 ml of fresh medium is added to the flask. The culture and the infection were performed at 37° C., 7.5% $CO_2$ and agitated at 60 rpm. Each day post infection an aliquot of the cell suspension is collected and frozen. At the end of the kinetic, an evaluation of the productivity is performed following the TCID50 method. Briefly, the titration of infectious MVA-GFP viruses was performed on DF-1 cells. Cells were seeded in 96 flat-bottom well plates at a density of $15 \times 10^3$ cells/well in DMEM medium (Biowhittaker) supplemented with 5% foetal calf serum (FCS) (SAFC) and 2 mM L-glutamine (Biowhittaker). Twenty-four hours later, cells were infected with ten fold serially diluted samples in DMEM and incubated for one week at 37° C., 5% $CO_2$ in a humidified atmosphere. Virus infectivity was measured through microscopic observation of global cytopathic effect (CPE) and UV-exposed infected cells. Then, TCID50 titers were calculated according the Reed and Muench method (1938, A simple method of estimating fifty percent endpoints. Am. J. Hyg. 27, 493-97). All along the experiment cell proliferation and viability are monitored. Chicken Valo EBv13 cells appear to be highly sensitive to MVA-GFP infection (FIGS. 3A-3B).

Example 8

Poxvirus Replication in Duck EBx Cell Lines

Susceptibility of duck EBx cells to infection with poxvirus was investigated using a recombinant Modified Vaccinia Ankara encoding a GFP. The virus titration was performed as previously described for chicken EBv13 cells.

8.1—Cell Culture Method

Duck EBx cells were stored in cryovials in liquid nitrogen at −196° C. ($20 \times 10^6$ cells/vial). The cryovial is directly thawed into a +37° C. pre-warmed water bath. The cell suspension is put into a 50 ml sterile tube with 30 ml pre-warmed culture medium. After centrifugation (5 min at 300±20 g, at room temperature), 15 ml of fresh culture medium is added on the pellet and gently homogenised. The sample is numbered using Trypan blue. Numeration has to be $\geq 20 \times 10^6$ cells and viability has to be >70% to guarantee a good culture.

The cell suspension is plated into a T75 $cm^2$ flask and incubate at +37° C. under an 7.5% $CO_2$ atmosphere on an orbital shaker at 50 rpm. Fresh medium is then added daily. The cells are then passaged to increase cells biomass to seed a 3 L-bioreactor. $320.10^6$ cells are needed to inoculate a 3 L-bioreactor. A sample is taken after gently mixing to perform a numeration using trypan blue to determine cell density. A 150 mL cell mix is prepared in order to obtain a cell concentration of $0.4 \times 10^6$ cells·ml$^{-1}$ into the 800 ml final culture volume in the bioreactor. Prior to seed cells, the pH is set in the vessel to 7.2 (because pH will be decrease by $CO_2$ surface injection). The $pO_2$ is set to 50% $O_2$ saturation (the mass flow controller is adjusted to 100% which correspond to a maximum sparger flow rate to 50 ml·min$^{-1}$). At the beginning of the process, the pH is maintained by $CO_2$ surface injection, later, it is controlled by addition of 7.5% $NaHCO_3$. The surface aeration is started with air at a flow rate of 0.3 ml·min$^{-1}$. Cell numeration is performed on a routine basis.

After 3 days of culture, cell density should be higher than $4-5 \times 10^6$ cells·ml$^{-1}$. If the expected cell density is reached, the virus infection is performed at a MOI of $10^{-4}$. The vessel temperature is set to 33° C. The virus strain is thawed on ice. The infection mix is prepared in 10 ml of production medium. After inoculation of the infection mix into the bioreactor, viral adsorption is performed during 1 hour. The final production medium is prepared: in 1.5 L of production medium, trypsin is added in order to obtain a final concentration in the vessel of 0.3 U·ml$^{-1}$ (2.3 L on the whole). The pre-warmed final production medium is then added. Every day a sample of approximately 15 ml is collected from the bioreactor to perform cell numeration, cell morphology analysis and to observe CPE. The metabolites such as glutamate, glutamine, lactate and glucose are analyzed all along the culture with the BioProfile Basic software. Concentration of the metabolites is adjusted if necessary. For example, glutamine concentration is adjusted to 2 mM if necessary. The glucose concentration is adjusted to 2 g·L$^{-1}$ if necessary.

Virus titration is carried-out at the end of the experiment using all collected samples.

8.2—Results 8.2.1—Cell Growth Kinetics of Duck EBx® Cells in a 3 L Fedbatch Bioreactor Duck EBx® cells are routinely cultured in stirred-tank bioreactor. Duck EBx®-derived biomass is allowed to accumulate at 37° C. in a cell growth medium until a cell density of $5-6.10^6$ cells/mL was reached. Then the mixture is diluted from around 3 to 10 fold, and cell growth kinetic is followed-up over a 10 days period. In such conditions, cell density of 12 to 20 million cells/ml is routinely reached around day 5 to 8. Thus Duck EBx® cells display a range of splitting ratio that goes at least up to 10 to 15 fold.

8.2.2—Influence of Cell Culture Medium Composition on the Clumps Size During MVA-GFP Virus Infection of Duck EBx Cells The inventors have found that the concentration of Calcium and Magnesium in the serum-free medium used for the EBx cells culture and infection may have an impact on the clumps size. The presence of small clumps of duck EBx cells improves virus infection and propagation, leading to high MVA virus titers (FIG. 9A).

8.2.3—MVA Virus Production in 3 L-Bioreactor

Duck EBx®-derived biomass was allowed to accumulate during cell proliferation phase in Excell 66444 growth medium. Cells were then infected with $10^{-2}$ $TCID_{50}$/cell of MVA-GFP virus and the mixture was diluted in Excell 66444 production medium. Following addition of fresh Excell medium, cell density dropped down on day 2, and at day 4, the cell density of infected cells increased and reached 12 million cell/ml. In such conditions, the MVA-GFP productivity is high. Since at day 4 post-infection, the MVA-GFP titer is around $10^8$ TCID50/ml (FIG. 9B). A MVA-GFP yield of 205 TCID50/cell was obtained in duck EBx® cells.

Example 9

Production of Influenza Virus in Duck EBx Cell Lines 9.1—Materials & Methods 9.1.1—Influenza Virus Infectivity Assay (TCID50)

Titration of infectious influenza viruses was performed on MDCK cells. In brief, cells were seeded in 96 flat-bottom well plates at a density of $3 \times 10^3$ cells/well in UltraMDCK medium supplemented with 2.5 mM L-glutamin. Twenty-four hours later, cells were infected with ten fold serially diluted samples in UltraMDCK containing 6 µg·mL$^{-1}$ trypsin-EDTA and incubated for one week at 33° C., 5% $CO_2$ in a humidified atmosphere. Virus replication was then tested in an HA assay using chicken red blood cells and TCID50 titers were calculated according the Reed and Muench method (1938)*.

*Reed L, Muench H, 1938. A simple method of estimating fifty percent endpoints. *Am. J. Hyg.* 27, 493-97.

9.1.2—Single Radial Immuno-Diffusion Assay (SRID)

The concentration of haemagglutinin in samples derived from influenza virus infected-EB14 cells, was determined as described by Wood and colleagues*. Briefly, glass plates were coated with an agarose gel containing anti-Influenza serum (recommended concentration provided by NIBSC). After the gel has set, 10 µL of appropriate dilutions of the reference and the samples were loaded in 3 mm Ø punched wells. Following a 18-24 h incubation in a moist chamber at room temperature, plates were soaked in 0.9% NaCl and washed in distilled water. The gel was then pressed and dried.

The plates were stained on Coomassie Brillant Blue solution for 15 min and destained twice in a mixture of methanol and acetic acid until clearly defined stained zones became visible. After drying the plates, the diameter of the stained zones surrounding antigen wells were measured in two directions at right angles. Dose-response curves of antigen dilutions against the surface were constructed and the results were calculated according to standard slope-ratio assay methods. *Wood J M. Et al. "An improved single-radial-immunodiffusion technique for the assay of influenza haemagglutinin antigen: application for potency determinations of inactivated whole virus and subunit vaccines" (J. Biol. Stand., 1977, 5(3):237-47).

9.1.3—Western Blot Analysis of Influenza Hemagglutinin Protein

SDS-PAGE was performed as described by Laemmli UK (1970, Cleavage of structural proteins during the assembly of the head of bacteriophage T4. Nature 259:680-685) in 10% polyacrylamide gel. Denatured proteins (1% SDS, 70 mM β-mercaptoethanol) were transferred to polyvinylidene difluoride membrane (hybond P, Amersham) by a semidry blotting procedure (Kyhse-Andersen J (1984) Electroblotting of multiple gels: a simple apparatus without buffer tank for rapid transfer of proteins from polyacrylamide to nitrocellulose (J Biochem Biophys Methods 10:203-209). Blots were blocked for 1 h at room temperature with a mixture composed of 5% fat dry milkpowder in TBST supplemented with 1% FCS (SAFC). Then, the blots were incubated overnight in blocking solution supplemented with specific polyclonal anti-HA sheep serum (1:500 (NIBSC). The blots were washed 6 times with TBST and incubated for 1 h at room temperature with a hrp-conjugated rabbit anti-sheep IgG polyclonal antibody (1:5000 (Rockland) in blocking solution. After 6 washes with TBST, the protein-conjugate complex was finally revealed using chemiluminescence (ECL kit, Amersham) and films (Hyperfilm, Amersham).

9.2—Influenza Virus Infection of Duck EBx® Cells in 3 L-Bioreactor 9.2.1—Materials and Equipment Cell Thawing Material
  T75 cm² flasks (Sarstedt, Cat#831813502)
  Culture medium (serum free medium)
  L-Glutamine 200 mM (Biowhittaker, Cat#BE17-605E)
  Orbital agitator IKA KS260 (Fisher Bioblock, Cat#F35044)

Cell Amplification Material
  T175 cm² flasks (Sarstedt, Cat#831812502)
  Culture medium (serum free medium): Excell 65319 (JRH, Cat#65319-1000M1687) added with 2.5 mM glutamine
  L-Glutamin 200 mM (Biowhittaker, Cat#BE17-605E)
  D (+) Glucose (45%) (Sigma, Cat#G8769)

Production Material
  Production medium (serum free medium): Excell 65629 (JRH, Cat#65629) supplemented with 2.5 mM glutamine
  L-Glutamine 200 mM (Biowhittaker, Cat#BE17-605E)
  D (+) Glucose (45%) (Sigma, Cat#G8769)
  Trypzean 1× (Sigma, Cat#T3449)
  7.5% bicarbonate sodium solution (Sigma, Cat#205-633-8)
  Influenza virus strain (frozen at −80° C.)

9.2.2—Cell Culture Method
(Idem as for MVA Replication—Example 7.1)

Virus titration, haemmaglutinin assays (HAU) and HA antigen quantifications (western blot, SRID) are carry out at the end of the experiment using all collected samples.

9.3—Results

The inventors demonstrate that duck EBx cells are a reliable and efficient cell substrate for the replication of various strains A and B of influenza virus. Influenza virus production can be performed in various vessels, such as flasks and spinner (data not shown) and bioreactors. Reproducible and efficient fedbatch process of production of influenza virus in 3 L and 30 L stirred tank bioreactors were obtained by the inventors. Viral yield above 15 mg/l and up to 50 mg/l of haemagglutinin are routinely obtained in flasks and in bioreactors with strains A and B of influenza virus (FIGS. 11 and 12).

Example 10

Newcastle Disease Virus Replication in Duck EBx Cell Lines

Susceptibility of duck EBx cells to infection with Newcastle Disease virus was investigated using a NDV La Sota strain.

10.1—Methods

Duck EBx® cells were grown in Excell medium (SFAC) in T175 flasks at 37° C. under 7.5% $CO_2$ atmosphere on an orbital shaker at 60 rpm. At day 0, cells are seeded at $0.4×10^6$ cells/mL in 40 ml fresh medium. Cell culture was incubated at 37° C., 7.5% $CO_2$ under shaking (60 rpm). Cell growth kinetics were followed until cell density has reached a concentration between $4×10^6$ to $6×10^6$ cells/ml (usually at day 3 post seeding). At that point, cells are inoculated with NDV La Sota strain at two different MOI ($10^{-3}$ and $10^{-4}$ $TCID_{50}$/cells) and incubated for one additional hour at 37° C., 7.5% $CO_2$ under shaking (60 RPM). Then the cell culture was diluted with the addition of 60 mL fresh viral production medium and the incubation pursued at 37° C. and 7.5% $CO_2$ under shaking (60 rpm). The cell growth and virus production kinetics were performed over 7 days. As a source of protease, recombinant trypsin (SAFC) was added every day in the culture medium; two concentration of trypsin (0.4 and 0.75 USP/mL) were tested. Daily aliquots were removed for cell numeration, virus titration and Western blotting analysis.

The samples were separated using 10% SDS-PAGE and blotted onto PDVF membrane (Amersham) by the semi-dry technique. Immunodetection was performed using chicken polyclonal antiserum against NDV (1:2000, CHARLES RIVER laboratories), followed by Alkaline phosphatase-conjugated rabbit anti-chicken (1:5000, SIGMA). Bound secondary antibody was detected using the ECL-Chemiluminescence detection system kit (ROCHE).

10.2—Results

Duck and chicken EBx cells are sensitive to and replicate NDV La Sota strain. Titers (in TCID50/ml) of NDV produced in duck EBx® cells increase from day 0 to day 2 pi to reach an average of $10^{6.83}$ $_{TCID50}$/mL (FIG. 13 left panel).

Western blot analysis (FIG. 13 right Panel) showed NDV viral proteins (HN, Fo/F, NP & M) expression. The viral proteins composition of NDV virus produced in duck EBx® cells are similar to the one obtained with NDV virus produced in chicken EBx® cells. In addition, the kinetic of release for viruses produced in chicken and Duck EBx cells are similar.

Example 11

Measles Virus Replication in Duck EB66 Cells

Susceptibility of duck EB66 cells to infection with measles virus was investigated using a recombinant measles virus expressing green fluorescent protein.

11.1—Methods

EB66 cells were grown in Excell medium in T175 flasks at 37° C. under 7.5% $CO_2$ atmosphere on an orbital shaker at 60 rpm. At day 0, cells are seeded at $0.4 \times 10^6$ cells/mL in 40 ml fresh medium. Cell culture was incubated at 37° C., 7.5% $CO_2$ under shaking (60 rpm). Cell growth kinetics were followed until cell density has reached a concentration between $4 \times 10^6$ to $6 \times 10^6$ cells/ml (usually at day 3 post seeding). At that point, cells are inoculated with recombinant measles virus at two different MOI ($10^{-1}$ and $10^{-2}$ $TCID_{50}$/cells) and incubated for one additional hour at 37° C., 7.5% $CO_2$ under shaking (60 RPM). Then the cell culture was diluted with the addition of 60 mL fresh viral production medium and the incubation pursued at 37° C. and 7.5% $CO_2$ under shaking (60 rpm). The cell growth and virus production kinetics were performed over 7 days. Daily aliquots were removed for cell numeration and virus titration.

11.2—Results

EB66 cells are sensitive to and replicate measles virus. In non optimised conditions, titers (in TCID50/ml) of measles produced in EB66 cells reach an average of $10^7$ TCID50/mL (FIG. 14).

The invention claimed is:

1. A method of making a duck cell line comprising:
   a) isolating a duck embryo around oviposition;
   b) dissociating the embryo of step a) into cells;
   c) seeding the dissociated cells of step b) in basal medium comprising insulin like growth factor 1 (IGF-1), ciliary neurotrophic factor (CNTF), animal serum, and a layer of feeder cells;
   d) culturing the cells of step c) for at least one passage;
   e) withdrawing the IGF-1 and CNTF from the culture of step d);
   f) culturing the cells of step e) for at least one passage;
   g) progressively withdrawing the feeder cells from the culture of step f);
   h) culturing the cells of step g) for at least one passage;
   i) progressively withdrawing the animal serum from the culture medium of step h) over several passages; and
   j) adapting the cells of step i) to suspension culture conditions such that a duck cell line capable of proliferating in basal medium in the absence of exogenous growth factors, a feeder layer, and animal serum is obtained, wherein the duck cell line does not produce replication-competent endogenous retrovirus particles.

2. The process according to claim 1, wherein the withdrawal of the growth factors IGF-1 and CNTF from the culture medium in step e) is performed simultaneously.

3. The process according to claim 1, wherein said duck is a Pekin duck.

4. The process according to claim 1, wherein said duck is a Muscovy duck.

5. The process according to claim 1 wherein said duck cell line has at least one of the following characteristics:
   - an endogenous telomerase activity,
   - a diameter of around 10 µm;
   - a population doubling time of around 30 hours or less at 37° C.; and
   - expresses one or more additional markers selected from the group consisting of alkaline phosphatase, SSEA-1, EMA-1, and ENS-1.

6. The process according to claim 1, wherein said duck cell line is diploid.

7. The process according to claim 1, wherein said duck cell line does not produce replication-competent endogenous avian leucosis virus (ALV-E) and/or endogenous avian virus (EAV) retrovirus particles.

8. The process according to claim 1 wherein the genome of said duck cell line does not contain proviral sequence of avian leucosis virus (ALV-E) and/or endogenous avian virus (EAV) susceptible to produce replication competent endogenous retroviral particles.

9. The method according to claim 1, wherein the concentration of IGF-1 and CNTF in step c) each is 1 ng/ml.

10. The method according to claim 1, wherein the concentration of animal serum in step c) is of 5% to 10%.

11. The method according to claim 1, wherein the feeder cells in step c) are mitotically inactivated mouse fibroblast cells.

* * * * *